(12) United States Patent
Zhu et al.

(10) Patent No.: US 9,856,464 B2
(45) Date of Patent: Jan. 2, 2018

(54) HIGH FIDELITY RESTRICTION ENDONUCLEASES

(71) Applicant: New England Biolabs, Inc., Ipswich, MA (US)

(72) Inventors: Zhenyu Zhu, Beverly, MA (US); Aine Quimby, Newton, NH (US); Shengxi Guan, Stoneham, MA (US); Dapeng Sun, Arlington, MA (US); Yishu Huang, Shanghai (CN); Xuhui Lai, Shanghai (CN); Siu-hong Chan, Ipswich, MA (US); Xianghui Li, Shanghai (CN); Shuang-Yong Xu, Lexington, MA (US); Chunhua Zhang, Zhenjiang (CN)

(*) Notice: Subject to any disclaimer, the term of this patent is extended or adjusted under 35 U.S.C. 154(b) by 28 days.

(21) Appl. No.: 15/133,093

(22) Filed: Apr. 19, 2016

(65) Prior Publication Data

US 2016/0289660 A1    Oct. 6, 2016

Related U.S. Application Data

(60) Continuation of application No. 14/137,583, filed on Dec. 20, 2013, now abandoned, which is a division of application No. 13/022,561, filed on Feb. 7, 2011, now Pat. No. 8,637,291, which is a continuation-in-part of application No. 12/172,963, filed on Jul. 14, 2008, now Pat. No. 8,372,619.

(60) Provisional application No. 60/959,203, filed on Jul. 12, 2007, provisional application No. 61/301,666, filed on Feb. 5, 2010, provisional application No. 61/387,800, filed on Sep. 29, 2010.

(51) Int. Cl.
| | |
|---|---|
| *C12N 9/22* | (2006.01) |
| *C12Q 1/34* | (2006.01) |
| *C12N 9/16* | (2006.01) |
| *C12Q 1/68* | (2006.01) |
| *C12Q 1/44* | (2006.01) |

(52) U.S. Cl.
CPC ............ *C12N 9/22* (2013.01); *C12N 9/16* (2013.01); *C12Q 1/34* (2013.01); *C12Q 1/44* (2013.01); *C12Q 1/68* (2013.01); *C12Y 301/21004* (2013.01); *G01N 2333/916* (2013.01); *G01N 2333/922* (2013.01)

(58) Field of Classification Search
CPC ........................................................ C12N 9/22
See application file for complete search history.

(56) References Cited

FOREIGN PATENT DOCUMENTS

WO    WO2007027464    3/2007

OTHER PUBLICATIONS

Wei, et al. "The Fidelity Index provides a systematic quantitation of star activity of DNA restriction endonucleases", Nucleic Acids Research, 2008, vol. 36, No. 9 e50, pp. 1-10.
Zhu, et al. "Isolation of Bso 81 Restriction Endonuclease Variants with Altered Substrate Specificity", J. Mol. Bioi. (2003) 330, 359-372.

*Primary Examiner* — Rebecca E Prouty
(74) *Attorney, Agent, or Firm* — New England Bio Labs, Inc.; Harriet M. Strimpel

(57) ABSTRACT

Methods and compositions are provided for engineering mutant enzymes with reduced star activity where the mutant enzymes have a fidelity index (FI) in a specified buffer that is greater than the FI of the non-mutated enzyme in the same buffer.

16 Claims, 17 Drawing Sheets

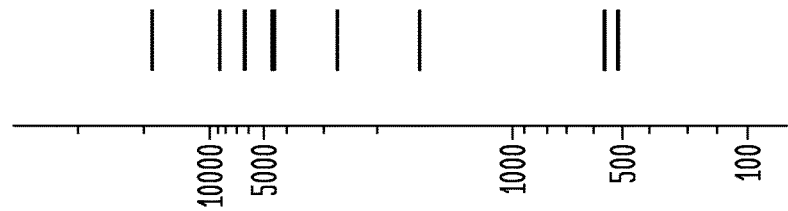
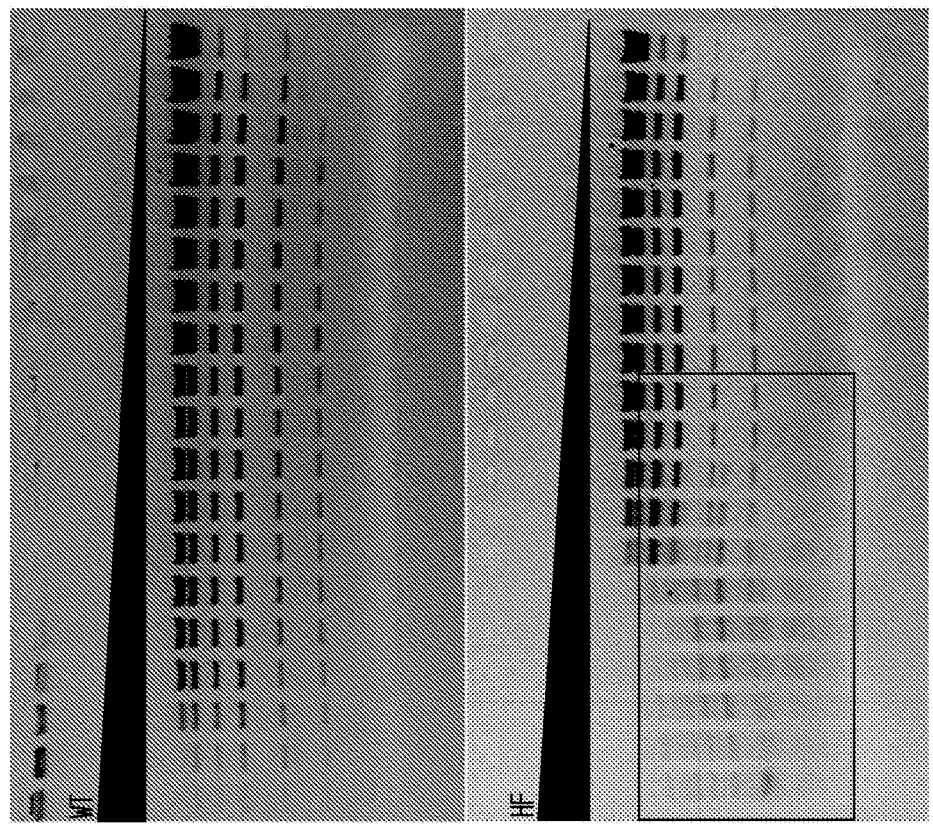
FIG. 8

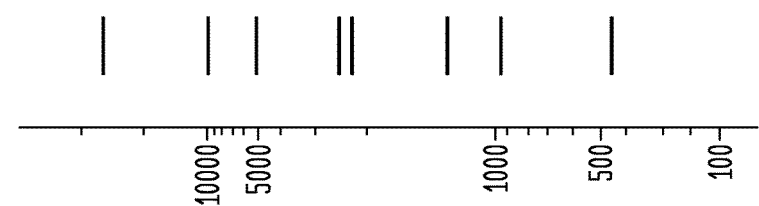
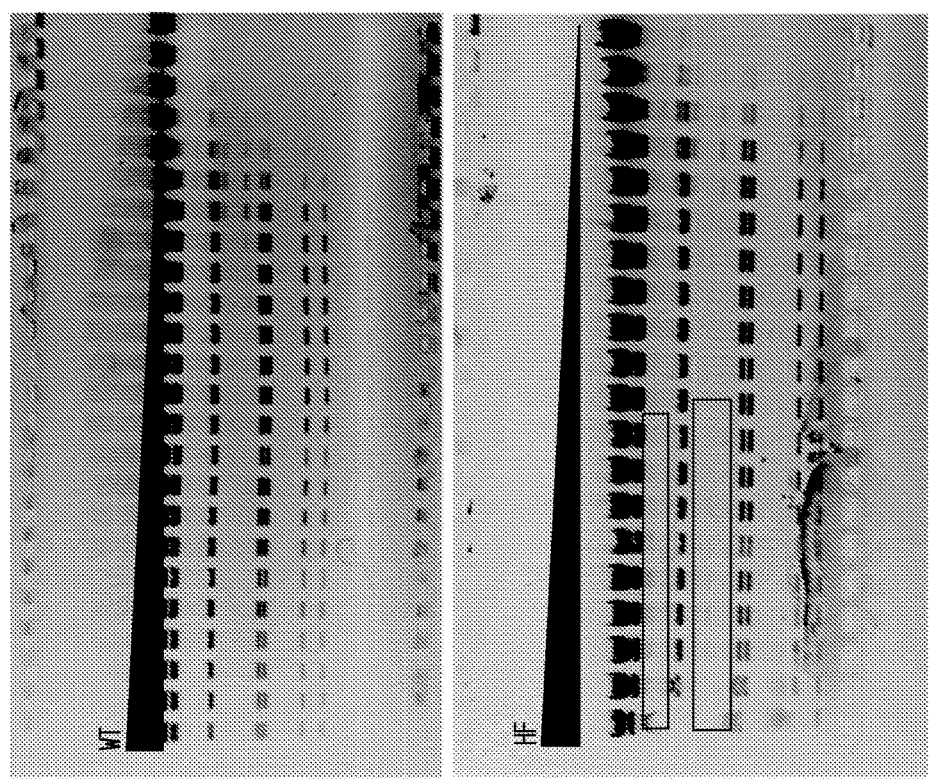
FIG. 15

SEQUENCE LISTING

```
<160> NUMBER OF SEQ ID NOS: 35

<210> SEQ ID NO 1
<211> LENGTH: 260
<212> TYPE: PRT
<213> ORGANISM: Proteus vulgaris

<400> SEQUENCE: 1

Met Lys Lys Asn Arg Tyr Glu Ser Ile Ile Glu Gly Ile Phe Leu Asp
1               5                   10                  15

Lys Tyr Val Asp Gly Asn Asp Ile Val Glu Phe Asn Arg Thr Asp Ile
            20                  25                  30

Ile Ser Lys Ser Ala Glu Leu Asp Ile Asn Leu Pro Lys Asn Ile Gly
        35                  40                  45

Asp Val Ile Tyr Ser Phe Lys Tyr Arg Ala Ser Leu Pro Val Ser Ile
    50                  55                  60

Thr Gln Lys Ala Gln Asn Gly Lys Glu Trp Val Ile Lys Asn Ile Gly
65                  70                  75                  80

Arg Ser Leu Tyr Cys Phe Gln Gln Val Asn Tyr Ser Arg Ile Leu Pro
                85                  90                  95

Asp Met Met Leu Ser Thr Ile Lys Ile Pro Asp Ser Thr Pro Thr Ile
            100                 105                 110

Val Ala Glu His Ala Phe Asn Asp Glu Gln Ala Leu Leu Thr Arg Val
        115                 120                 125

Arg Tyr Asn Arg Leu Ile Asp Ile Phe Thr Gly Ala Val Cys Tyr Ser
    130                 135                 140

Leu Gln Asn His Leu Arg Thr Thr Val Pro Ser Val Gly Gln Ile Glu
145                 150                 155                 160

Thr Asp Glu Ile Tyr Val Gly Val Asp Arg Leu Gly Arg Gln Phe Ile
                165                 170                 175

Phe Pro Val Gln Ala Lys Gly Gly Lys Asp Glu Leu Gly Ile Val Gln
            180                 185                 190

Ile Glu Gln Asp Phe Leu Leu Cys Arg His Lys Tyr Pro Asn Leu Ile
        195                 200                 205

Cys Arg Pro Ile Ala Thr Gln Phe Ile Ser Asn Asp Lys Ile Ala Ile
    210                 215                 220

Phe Glu Phe Val Leu Glu Asn Asn Glu Val Lys Lys Leu Gln Glu Lys
225                 230                 235                 240

His Tyr Leu Leu Val Gly Lys Gly Gln Ile Ser Val Asp Glu Leu Ser
                245                 250                 255

Asn Tyr Asn Phe
            260

<210> SEQ ID NO 2
<211> LENGTH: 300
<212> TYPE: PRT
<213> ORGANISM: Haemophilus influenzae

<400> SEQUENCE: 2

Met Lys Lys Ser Ala Leu Glu Lys Leu Leu Ser Leu Ile Glu Asn Leu
1               5                   10                  15
```

```
Thr Asn Gln Glu Phe Lys Gln Ala Thr Asn Ser Leu Ile Ser Phe Ile
            20                  25                  30

Tyr Lys Leu Asn Arg Asn Glu Val Ile Glu Leu Val Arg Ser Ile Gly
        35                  40                  45

Ile Leu Pro Glu Ala Ile Lys Pro Ser Ser Thr Gln Glu Lys Leu Phe
    50                  55                  60

Ser Lys Ala Gly Asp Ile Val Leu Ala Lys Ala Phe Gln Leu Leu Asn
65                  70                  75                  80

Leu Asn Ser Lys Pro Leu Glu Gln Arg Gly Asn Ala Gly Asp Val Ile
                85                  90                  95

Ala Leu Ser Lys Glu Phe Asn Tyr Gly Leu Val Ala Asp Ala Lys Ser
            100                 105                 110

Phe Arg Leu Ser Arg Thr Ala Lys Asn Gln Lys Asp Phe Lys Val Lys
        115                 120                 125

Ala Leu Ser Glu Trp Arg Glu Asp Lys Asp Tyr Ala Val Leu Thr Ala
    130                 135                 140

Pro Phe Phe Gln Tyr Pro Thr Thr Lys Ser Gln Ile Phe Lys Gln Ser
145                 150                 155                 160

Leu Asp Glu Asn Val Leu Leu Phe Ser Trp Glu His Leu Ala Ile Leu
                165                 170                 175

Leu Gln Leu Asp Leu Glu Glu Thr Asn Ile Phe Pro Phe Glu Gln Leu
            180                 185                 190

Trp Asn Phe Pro Lys Lys Gln Ser Lys Lys Thr Ser Val Ser Asp Ala
        195                 200                 205

Glu Asn Asn Phe Met Arg Asp Phe Asn Lys Tyr Phe Met Asp Leu Phe
210                 215                 220

Lys Ile Asp Lys Asp Thr Leu Asn Gln Leu Leu Gln Lys Glu Ile Asn
225                 230                 235                 240

Phe Ile Glu Glu Arg Ser Leu Ile Glu Lys Glu Tyr Trp Lys Lys Gln
                245                 250                 255

Ile Asn Ile Ile Lys Asn Phe Thr Arg Glu Glu Ala Ile Glu Ala Leu
            260                 265                 270

Leu Lys Asp Ile Asn Met Ser Ser Lys Ile Glu Thr Ile Asp Ser Phe
        275                 280                 285

Ile Lys Gly Ile Lys Ser Asn Asp Arg Leu Tyr Leu
    290                 295                 300

<210> SEQ ID NO 3
<211> LENGTH: 227
<212> TYPE: PRT
<213> ORGANISM: Deinococcus radiophilus

<400> SEQUENCE: 3

Met Glu Leu Cys His Lys Thr Val Lys Ser Arg Thr Ala Tyr Ser Lys
1               5                   10                  15

His Phe Pro His Lys Cys Gln Leu Pro Leu Gly His Ser Gly Lys Cys
                20                  25                  30

Leu Glu Phe Pro Phe Leu Val Ser Leu Ser Lys Thr His Pro Arg Ile
            35                  40                  45

Ala Ala Lys Ile Val Arg Asp Ala Thr Met Thr Thr Gly Ala Ala Trp
    50                  55                  60

Lys Ser Ser Gln Ala Gly Pro Asn Arg Met Pro Arg Tyr Val Ala Ile
65                  70                  75                  80

Leu Asp Asp Asp Ile Leu Leu Glu Lys Phe Asn Leu Asp Met Gln Ser
                85                  90                  95
```

```
Leu Pro Glu Ile Thr Arg Leu Lys Ile Arg Glu Lys Ala Ala Asp Tyr
                100                 105                 110

Asp Ser Cys Ile Asp Val Ala Arg Lys Leu Thr Trp Leu Ala Tyr Gln
            115                 120                 125

Leu His Gly Ala Pro Ile Pro Asp Ser Phe Thr Lys Asn Tyr Leu Glu
        130                 135                 140

Glu Phe Phe Gly Pro Met Val Ala Gly Ser Thr Asn Cys Glu Ile Cys
145                 150                 155                 160

Lys Leu Pro Leu Thr Ile Asp Leu Phe Ser Glu Asn Arg Val Gly Lys
                165                 170                 175

Ala Ala Val Glu Thr Ala His Lys Thr Pro Arg Leu His Asn Ala Glu
            180                 185                 190

Asn Val Gly Phe Ala His Arg Phe Cys Asn Val Ala Gln Gly Asn Lys
        195                 200                 205

Ser Leu Asp Glu Phe Tyr Leu Trp Met Glu Glu Val Leu Thr Arg Val
    210                 215                 220

Lys Met Leu
225

<210> SEQ ID NO 4
<211> LENGTH: 218
<212> TYPE: PRT
<213> ORGANISM: Klebsiella pneumoniae

<400> SEQUENCE: 4

Met Asp Val Phe Asp Lys Val Tyr Ser Asp Asn Asn Ser Tyr Asp
1               5                   10                  15

Gln Lys Thr Val Ser Gln Arg Ile Glu Ala Leu Phe Leu Asn Asn Leu
            20                  25                  30

Gly Lys Val Val Thr Arg Gln Gln Ile Ile Arg Ala Ala Thr Asp Pro
        35                  40                  45

Lys Thr Gly Lys Gln Pro Glu Asn Trp His Gln Arg Leu Ser Glu Leu
50                  55                  60

Arg Thr Asp Lys Gly Tyr Thr Ile Leu Ser Trp Arg Asp Met Lys Val
65                  70                  75                  80

Leu Ala Pro Gln Glu Tyr Ile Met Pro His Ala Thr Arg Arg Pro Lys
                85                  90                  95

Ala Ala Lys Arg Val Leu Pro Thr Lys Glu Thr Trp Glu Gln Val Leu
            100                 105                 110

Asp Arg Ala Asn Tyr Ser Cys Glu Trp Gln Glu Asp Gly Gln His Cys
        115                 120                 125

Gly Leu Val Glu Gly Asp Ile Asp Pro Ile Gly Gly Thr Val Lys
        130                 135                 140

Leu Thr Pro Asp His Met Thr Pro His Ser Ile Asp Pro Ala Thr Asp
145                 150                 155                 160

Val Asn Asp Pro Lys Met Trp Gln Ala Leu Cys Gly Arg His Gln Val
                165                 170                 175

Met Lys Lys Asn Tyr Trp Asp Ser Asn Asn Gly Lys Ile Asn Val Ile
            180                 185                 190

Gly Ile Leu Gln Ser Val Asn Glu Lys Gln Lys Asn Asp Ala Leu Glu
        195                 200                 205

Phe Leu Leu Asn Tyr Tyr Gly Leu Lys Arg
    210                 215
```

```
<210> SEQ ID NO 5
<211> LENGTH: 355
<212> TYPE: PRT
<213> ORGANISM: Salmonella typhi

<400> SEQUENCE: 5

Met Asn Phe Lys Asp Lys Asn Cys Phe Pro Asn Glu Leu Ile Ala Leu
1               5                   10                  15

Ala Lys Ile Ser Lys Asn Asp Val Leu Asp Lys Phe Gly Thr Asp Val
            20                  25                  30

Phe Lys Lys Val Val Tyr Asp Val Leu Thr Gly Lys Asn Val Arg Glu
        35                  40                  45

Phe Thr Glu Ile Leu Thr Arg Thr Arg Leu Leu Glu Ser Asn Leu Ser
50                  55                  60

Phe Phe Asp Phe Phe Val Asp Lys Met Lys Glu Gly Ile Thr Pro Lys
65                  70                  75                  80

Gln Leu Tyr Leu Tyr Ala Lys Asn Ala Leu Ser Asn Lys Ser Tyr Val
                85                  90                  95

Lys Tyr Asn Gln Pro Val Leu Glu Trp Met Val Met Thr Asn Lys
            100                 105                 110

Gln Thr Gln Asn Val Leu Arg Asp Glu His Gly Asp Gly Phe Asp Arg
        115                 120                 125

Leu Ala Leu Arg Thr Gln Glu Glu Ile Leu Lys Ile Lys Asn Gly Tyr
130                 135                 140

Glu Asp Lys Ile Gly Glu Ile Ser Ile Gly Gly Gln Lys Val Ser Leu
145                 150                 155                 160

Glu Asp Phe Cys Tyr Ile Ile Leu Ser Leu Gly Ser Gln Thr Leu Thr
                165                 170                 175

Ile Arg Gly Ser Glu Lys Ser Leu His Gly Lys Tyr Phe Glu Lys Leu
            180                 185                 190

Ile Leu Gly Ser Leu Phe Thr Ile Met Gly Phe Glu Tyr Lys Glu Lys
        195                 200                 205

Ile Glu Glu Gly Leu Asn Ala Lys Cys Phe Thr Leu Ser Thr Arg Ala
210                 215                 220

Asp Asp Arg Glu Ser Asp Ala Thr Leu Ile Phe Asn Gly Lys Ala Ile
225                 230                 235                 240

Arg Val Asp Ile Gly Phe Ile Gly Arg Gly Asn Thr Glu Ile Ser Leu
                245                 250                 255

Asp Lys Val Ser Arg Phe Arg Arg Met Asp Ile Gly Gly Val Met
            260                 265                 270

His Asn Ile Ser Thr Met Val Ile Val Asp Val Ile Gly Asp Arg Ser
        275                 280                 285

Arg Ile Val Asn Met Ala Glu Glu Ile Asp Gly Lys Val Val Ala Met
290                 295                 300

Ser Asp Pro Tyr Trp Val Ala Lys Val Ser Ser Tyr Ile Ser Ser Lys
305                 310                 315                 320

Leu Asn Val Asp Asp Leu Leu Glu Asp Lys Pro Gln Leu Lys Tyr Ile
                325                 330                 335

Gln Ser Phe Ile Ser Asp Ala Leu Glu Asn Val Asp Leu Glu Lys Tyr
            340                 345                 350

Ile Lys Leu
    355

<210> SEQ ID NO 6
<211> LENGTH: 307
```

<212> TYPE: PRT
<213> ORGANISM: Bacillus stearothermophilus

<400> SEQUENCE: 6

Met Thr Phe Asp Lys Ile Ala Val Lys Gln Ile Leu Arg Leu Leu
1               5                   10                  15

Lys Gly Glu Asp Tyr Arg Gly Glu Val Leu Asn Ile Ile Asn Ala Asp
            20                  25                  30

Phe Leu Asp Phe Ala Leu Gln Phe Phe Lys Asp Val Ala Leu Ala Lys
        35                  40                  45

Leu Gln Asn Glu Glu Leu Thr Asp Asp Trp Tyr Lys Lys Tyr Phe Ile
50                  55                  60

Gln Asn Pro Ser Leu Thr Lys Glu Lys Val Ala Ile Tyr Ser Gly Leu
65                  70                  75                  80

Asn Met Lys Thr Ile Ser Asn Thr Tyr Lys Thr Ala Lys Asn Val
                85                  90                  95

Val Val Asp Ala Ser Leu Glu His Tyr Asp Ala Phe Val Lys Thr Ile
            100                 105                 110

Gln Glu Leu Ile Glu Ile Asp Asp Ser Leu Glu Leu Met Leu Thr Ile
        115                 120                 125

Lys Tyr Asn Lys Val Ser Val Glu Leu Thr Leu Ser Glu Ser Leu Ile
130                 135                 140

Val Met Asn Val Leu Ala Val Lys Arg Ala Ala Ile Arg Gly Gly Ala
145                 150                 155                 160

Trp Ser Thr Ala Gly Lys Arg Val Glu Lys Leu Leu Met Leu Thr Leu
                165                 170                 175

Cys Lys Leu Phe Arg Val Pro Asp Lys His Tyr Lys Ser Ile Tyr Val
            180                 185                 190

Ala Gln Leu Lys Asp Glu Asn Asp Phe Ser Arg Glu Ile Asp Phe Tyr
        195                 200                 205

Leu Ile Asp Gln Asn Asn Asn Glu Leu Lys Cys Glu Val Lys Leu Met
210                 215                 220

Gly Lys Gly Asn Pro Glu Ser Ala Asp Ala Val Ile Ala Arg Asp Ser
225                 230                 235                 240

Lys Ile Phe Val Ala Asp Thr Leu Ser Glu Thr Asn Lys Lys Gln Leu
                245                 250                 255

Asp Phe Leu Lys Val Glu Trp Val Glu Leu Arg Ser Lys Gly Tyr
            260                 265                 270

Glu Lys Phe Lys Thr Ile Leu Ser Asn Arg Gly Ile Pro Tyr Glu Asp
        275                 280                 285

Ile Glu Glu Ile Thr Pro Glu Tyr Leu Glu Lys Val Ile Asp Glu Ser
290                 295                 300

Leu Gly Ile
305

<210> SEQ ID NO 7
<211> LENGTH: 272
<212> TYPE: PRT
<213> ORGANISM: Bacillus stearothermophilus

<400> SEQUENCE: 7

Met Asn Phe Phe Glu Tyr Cys Ile Ser Thr Tyr Ala Lys Ile Phe Glu
1               5                   10                  15

Glu Thr Met Asn Ala Val Gly Asp Glu Arg Val Ser Gln Lys Lys Ala
            20                  25                  30

Ile Arg Asp Thr Met Ile Ser Ala Met Arg Glu Phe Pro Asn Val Glu
        35                  40                  45

Ala Ala Glu Ile Trp Lys Ala Val Tyr Ser Ala His Met Asp Arg Lys
 50                  55                  60

Ser Gly Ile Ala Asp Pro Asp Ile Ile Gln Lys Val Ile Ser Ala Glu
65                  70                  75                  80

Asn Ser Trp Lys Lys Ser Ser Gly His Ala Phe Glu Glu Met Ile Lys
                85                  90                  95

Leu Leu Gly Asn Ser Ser Leu Glu Glu Tyr Gly Met Arg Ile Leu Leu
            100                 105                 110

Gln Lys Asp Leu Asn Met Met Ile Glu Asn Gln Glu Ile Ala Asn Glu
        115                 120                 125

Pro Arg Asp Ile Asn Trp Leu Lys Glu Gln Ile Ser Ser Asn Val Phe
130                 135                 140

Asp Leu Tyr Ile Thr Val Arg Asn Asn Asp Lys Glu Tyr Val Phe Gly
145                 150                 155                 160

Cys Ile Gln Ser Lys Thr Ser Ile Arg Asp Arg Val Thr Arg Asp Arg
                165                 170                 175

Glu Pro Ser Met Lys Ala Met Glu Ala Phe Phe Trp Ser Val Ala Ile
            180                 185                 190

Cys Leu Asp Gly Asp Phe Leu Lys Met Pro Lys Phe Ile Ala Met Val
        195                 200                 205

Asn Gly Gly Thr Ser Asn Tyr Arg Leu Asn Gly Trp His Gly Met Tyr
210                 215                 220

Val Phe Trp Asp Lys Pro Thr Ile Asp Arg Ile Tyr Pro Ile Asp Ile
225                 230                 235                 240

Asn Leu Glu Leu Phe Val Gln His Ala Arg Glu Ala Ala Glu Asp Trp
                245                 250                 255

Leu His Arg Arg Gln Trp Phe Asn Tyr Glu Trp Lys Ala Gly Gln Lys
            260                 265                 270

<210> SEQ ID NO 8
<211> LENGTH: 299
<212> TYPE: PRT
<213> ORGANISM: Bacillus globigii

<400> SEQUENCE: 8

Met Tyr Asn Leu His Arg Glu Lys Ile Phe Met Ser Tyr Asn Gln Asn
1               5                   10                  15

Lys Gln Tyr Leu Glu Asp Asn Pro Glu Ile Gln Glu Lys Ile Glu Leu
            20                  25                  30

Tyr Gly Leu Asn Leu Leu Asn Glu Val Ile Ser Asp Asn Glu Glu Glu
        35                  40                  45

Ile Arg Ala Asp Tyr Asn Glu Ala Asn Phe Leu His Pro Phe Trp Met
 50                  55                  60

Asn Tyr Pro Pro Leu Asp Arg Gly Lys Met Pro Lys Gly Asp Gln Ile
65                  70                  75                  80

Pro Trp Ile Glu Val Gly Glu Lys Ala Val Gly Ser Lys Leu Thr Arg
                85                  90                  95

Leu Val Ser Gln Arg Glu Asp Ile Thr Val Arg Glu Ile Gly Leu Pro
            100                 105                 110

Thr Gly Pro Asp Glu Arg Tyr Leu Leu Thr Ser Pro Thr Ile Tyr Ser
        115                 120                 125

Leu Thr Asn Gly Phe Thr Asp Ser Ile Met Met Phe Val Asp Ile Lys
130                 135                 140

```
Ser Val Gly Pro Arg Asp Ser Asp Tyr Asp Leu Val Leu Ser Pro Asn
145                 150                 155                 160

Gln Val Ser Gly Asn Gly Asp Trp Ala Gln Leu Glu Gly Gly Ile Gln
            165                 170                 175

Asn Asn Gln Gln Thr Ile Gln Gly Pro Arg Ser Ser Gln Ile Phe Leu
        180                 185                 190

Pro Thr Ile Pro Pro Leu Tyr Ile Leu Ser Asp Gly Thr Ile Ala Pro
    195                 200                 205

Val Val His Leu Phe Ile Lys Pro Ile Tyr Ala Met Arg Ser Leu Thr
210                 215                 220

Lys Gly Asp Thr Gly Gln Ser Leu Tyr Lys Ile Lys Leu Ala Ser Val
225                 230                 235                 240

Pro Asn Gly Leu Gly Leu Phe Cys Asn Pro Gly Tyr Ala Phe Asp Ser
                245                 250                 255

Ala Tyr Lys Phe Leu Phe Arg Pro Gly Lys Asp Asp Arg Thr Lys Ser
            260                 265                 270

Leu Leu Gln Lys Arg Val Arg Val Asp Leu Arg Val Leu Asp Lys Ile
        275                 280                 285

Gly Pro Arg Val Met Thr Ile Asp Met Asp Lys
    290                 295
```

<210> SEQ ID NO 9
<211> LENGTH: 533
<212> TYPE: PRT
<213> ORGANISM: Bacillus stearothermophilus

<400> SEQUENCE: 9

```
Met Thr Glu Tyr Asp Leu His Leu Tyr Ala Asp Ser Phe His Glu Gly
1               5                   10                  15

His Trp Cys Cys Glu Asn Leu Ala Lys Ile Ala Gln Ser Asp Gly Gly
            20                  25                  30

Lys His Gln Ile Asp Tyr Leu Gln Gly Phe Ile Pro Arg His Ser Leu
        35                  40                  45

Ile Phe Ser Asp Leu Ile Ile Asn Ile Thr Val Phe Gly Ser Tyr Lys
    50                  55                  60

Ser Trp Lys His Leu Pro Lys Gln Ile Lys Asp Leu Leu Phe Trp Gly
65                  70                  75                  80

Lys Pro Asp Phe Ile Ala Tyr Asp Pro Lys Asn Asp Lys Ile Leu Phe
                85                  90                  95

Ala Val Glu Glu Thr Gly Ala Val Pro Thr Gly Asn Gln Ala Leu Gln
            100                 105                 110

Arg Cys Glu Arg Ile Tyr Gly Ser Ala Arg Lys Gln Ile Pro Phe Trp
        115                 120                 125

Tyr Leu Leu Ser Glu Phe Gly Gln His Lys Asp Gly Gly Thr Arg Arg
    130                 135                 140

Asp Ser Ile Trp Pro Thr Ile Met Gly Leu Lys Leu Thr Gln Leu Val
145                 150                 155                 160

Lys Thr Pro Ser Ile Ile Leu His Tyr Ser Asp Ile Asn Asn Pro Glu
                165                 170                 175

Asp Tyr Asn Ser Gly Asn Gly Leu Lys Phe Leu Phe Lys Ser Leu Leu
            180                 185                 190

Gln Ile Ile Ile Asn Tyr Cys Thr Leu Lys Asn Pro Leu Lys Gly Met
        195                 200                 205

Leu Glu Leu Leu Ser Ile Gln Tyr Glu Asn Met Leu Glu Phe Ile Lys
```

-continued

```
                210                 215                 220
Ser Gln Trp Lys Glu Gln Ile Asp Phe Leu Pro Gly Glu Ile Leu
225                 230                 235                 240

Asn Thr Lys Thr Lys Glu Leu Ala Arg Met Tyr Ala Ser Leu Ala Ile
                245                 250                 255

Gly Gln Thr Val Lys Ile Pro Glu Glu Leu Phe Asn Trp Pro Arg Thr
                260                 265                 270

Asp Lys Val Asn Phe Lys Ser Pro Gln Gly Leu Ile Lys Tyr Asp Glu
                275                 280                 285

Leu Cys Tyr Gln Leu Glu Lys Ala Val Gly Ser Lys Lys Ala Tyr Cys
                290                 295                 300

Leu Ser Asn Asn Ala Gly Ala Lys Pro Gln Lys Leu Glu Ser Leu Lys
305                 310                 315                 320

Glu Trp Ile Asn Ser Gln Lys Lys Leu Phe Asp Lys Ala Pro Lys Leu
                325                 330                 335

Thr Pro Pro Ala Glu Phe Asn Met Lys Leu Asp Ala Phe Pro Val Thr
                340                 345                 350

Ser Asn Asn Asn Tyr Tyr Val Thr Thr Ser Lys Asn Ile Leu Tyr Leu
                355                 360                 365

Phe Asp Tyr Trp Lys Asp Leu Arg Ile Ala Ile Glu Thr Ala Phe Pro
                370                 375                 380

Arg Leu Lys Gly Lys Leu Pro Thr Asp Ile Asp Glu Lys Pro Ala Leu
385                 390                 395                 400

Ile Tyr Ile Cys Asn Ser Val Lys Pro Gly Arg Leu Phe Gly Asp Pro
                405                 410                 415

Phe Thr Gly Gln Leu Ser Ala Phe Ser Thr Ile Phe Gly Lys Lys Asn
                420                 425                 430

Ile Asp Met Pro Arg Ile Val Val Ala Tyr Tyr Pro His Gln Ile Tyr
                435                 440                 445

Ser Gln Ala Leu Pro Lys Asn Asn Lys Ser Asn Lys Gly Ile Thr Leu
                450                 455                 460

Lys Lys Glu Leu Thr Asp Phe Leu Ile Phe His Gly Gly Val Val Val
465                 470                 475                 480

Lys Leu Asn Glu Gly Lys Ala Tyr Pro His Gln Ile Tyr Ser Gln Ala
                485                 490                 495

Leu Pro Lys Asn Asn Lys Ser Asn Lys Gly Ile Thr Leu Lys Lys Glu
                500                 505                 510

Leu Thr Asp Phe Leu Ile Phe His Gly Gly Val Val Val Lys Leu Asn
                515                 520                 525

Glu Gly Lys Ala Tyr
                530
```

<210> SEQ ID NO 10
<211> LENGTH: 383
<212> TYPE: PRT
<213> ORGANISM: Neisseria sicca

<400> SEQUENCE: 10

```
Met Ile Asn His Ser Ile Leu Lys His His Ser Phe Thr Gly Lys Ile
1               5                   10                  15

Ile Ser Ile Leu Lys Asp Glu Phe Gly Asp Asp Ala Ile Tyr Ile Phe
                20                  25                  30

Glu Asn Ser Pro Ile Leu Gly Tyr Leu Asn Ile Lys Thr Lys Ser Ala
                35                  40                  45
```

```
Glu Arg Gly Ser Lys Ser Arg Gly Ser Phe Ala Asn His Tyr Ala Leu
 50                  55                  60

Tyr Val Ile Ile Glu Asp Tyr Ile Asn Lys Gly Tyr Leu Gly Asp Asp
 65                  70                  75                  80

Leu Asp Tyr Ser Lys Tyr Asp Gly Ala Lys Phe Thr Asp Leu Phe Arg
                 85                  90                  95

Arg Gln Arg Glu Leu Pro Phe Gly Ser Lys Leu Gln Asn His Ala Leu
                100                 105                 110

Asn Ser Arg Leu Asn Asp Glu Phe Lys Lys Phe Pro Thr Leu Gly
                115                 120                 125

Ile Val Pro Ile Ile Arg Asp Val Arg Thr Ser Arg Tyr Trp Ile Gln
130                 135                 140

Glu Asp Leu Ile Lys Val Ser Arg Asn Lys Asn Gly Ile Glu Arg
145                 150                 155                 160

Arg Glu Asn Leu Ala Pro Ser Ile Ile Arg Ile Ile Asp Glu Tyr Ile
                165                 170                 175

Ala Thr Lys Lys Glu Ser Phe Glu Leu Phe Leu Lys Thr Cys Gln Glu
                180                 185                 190

Ile Ala Asn Leu Ser Ser Ser Asp Pro His Ser Val Val Lys Phe Ile
                195                 200                 205

Gln Glu Gln Leu His Pro Ser Ser Asp Ala Arg Val Phe Glu Ile Val
                210                 215                 220

Ser Tyr Ala Val Leu Lys Glu Arg Tyr Ser Asn Gln Thr Ile Trp Ile
225                 230                 235                 240

Gly Asp Ser Arg Asp Asp Val Ala Glu Glu Ser Leu Val Leu Tyr Lys
                245                 250                 255

Thr Gly Arg Thr Asn Ala Asn Asp Gly Gly Ile Asp Phe Val Met Lys
                260                 265                 270

Pro Leu Gly Arg Phe Phe Gln Val Thr Glu Thr Ile Asp Ala Asn Lys
                275                 280                 285

Tyr Phe Leu Asp Ile Asp Lys Val Gln Arg Phe Pro Ile Thr Phe Val
                290                 295                 300

Val Lys Thr Asn Ser Ser Tyr Glu Glu Ile Glu Lys Ile Ile Lys Glu
305                 310                 315                 320

Gln Ala Lys Ala Lys Tyr Asn Ile Glu Ala Ile Val Asn Ser Tyr Met
                325                 330                 335

Asp Ser Ile Glu Glu Ile Ile Asn Val Pro Asp Leu Met Lys Tyr Phe
                340                 345                 350

Glu Glu Met Ile Tyr Ser Asp Ser Leu Lys Arg Ile Met Asp Glu Ile
                355                 360                 365

Ile Val Gln Ser Lys Val Glu Phe Asn Tyr Glu Glu Asp Val Ser
                370                 375                 380

<210> SEQ ID NO 11
<211> LENGTH: 288
<212> TYPE: PRT
<213> ORGANISM: Diplococcus pneumoniae

<400> SEQUENCE: 11

Met Lys Gln Thr Arg Asn Phe Asp Glu Trp Leu Ser Met Thr Asp
  1               5                  10                  15

Thr Val Ala Asp Trp Thr Tyr Tyr Thr Asp Phe Pro Lys Val Tyr Lys
                 20                  25                  30

Asn Val Ser Ser Ile Lys Val Ala Leu Asn Ile Met Asn Ser Leu Ile
                 35                  40                  45
```

Gly Ser Lys Asn Ile Gln Glu Asp Phe Leu Asp Leu Tyr Gln Asn Tyr
        50                  55                  60

Pro Glu Ile Leu Lys Val Pro Leu Leu Ile Ala Lys Arg Leu Arg
 65                  70                  75                  80

Asp Thr Ile Ile Val Lys Asp Pro Ile Lys Asp Phe Tyr Phe Asp Phe
                    85                  90                  95

Ser Lys Arg Asn Tyr Ser Ile Glu Glu Tyr Thr Met Phe Leu Glu Lys
                100                 105                 110

Ser Gly Ile Phe Asp Leu Leu Gln Asn His Leu Val Ser Asn Leu Val
            115                 120                 125

Asp Tyr Val Thr Gly Val Glu Val Gly Met Asp Thr Asn Gly Arg Lys
130                 135                 140

Asn Arg Thr Gly Asp Ala Met Glu Asn Ile Val Gln Ser Tyr Leu Glu
145                 150                 155                 160

Ala Glu Gly Tyr Ile Leu Gly Glu Asn Leu Phe Lys Glu Ile Glu Gln
                165                 170                 175

Asn Glu Ile Glu Glu Ile Phe Ser Val Asp Leu Ser Ala Ile Thr Asn
                180                 185                 190

Asp Gly Asn Thr Val Lys Arg Phe Asp Phe Val Ile Lys Asn Glu Gln
            195                 200                 205

Val Leu Tyr Leu Ile Glu Val Asn Phe Tyr Ser Gly Ser Gly Ser Lys
210                 215                 220

Leu Asn Glu Thr Ala Arg Ser Tyr Lys Met Ile Ala Glu Glu Thr Lys
225                 230                 235                 240

Ala Ile Pro Asn Val Glu Phe Met Trp Ile Thr Asp Gly Gln Gly Trp
                245                 250                 255

Tyr Lys Ala Lys Asn Asn Leu Arg Glu Thr Phe Asp Ile Leu Pro Phe
                260                 265                 270

Leu Tyr Asn Ile Asn Asp Leu Glu His Asn Ile Leu Lys Asn Leu Lys
            275                 280                 285

<210> SEQ ID NO 12
<211> LENGTH: 285
<212> TYPE: PRT
<213> ORGANISM: Bacillus caldolyticus

<400> SEQUENCE: 12

Met Gln Pro Asn Pro Lys Phe Ile Asn Lys Ser Ser Ala Phe Trp Ala
 1                   5                  10                  15

Tyr Ala Lys Leu Leu Ser Glu Gln Leu Gly Tyr Ser Lys Asp Gly Val
                 20                  25                  30

Val Ile Ser Tyr Ser Glu Ala Gln Ala Arg Ala Lys Leu Lys Lys Leu
            35                  40                  45

Gly Ile Asn Val Lys Glu Gly Ile Phe Lys Asp Val Leu Arg Tyr Leu
 50                  55                  60

Lys Tyr Arg Ala Glu Leu Leu Asn Lys His Lys Asp Tyr Leu Met Asp
 65                  70                  75                  80

Val Glu Glu Ala Arg Lys Tyr Phe Gln Val Ala Leu Lys Gln His Gln
                 85                  90                  95

Gln Asn Asn Tyr Thr Cys Lys Leu Pro Leu Asn Lys Gln Lys Asn Glu
                100                 105                 110

Lys Lys Asp Tyr Ala Tyr Phe Thr Cys Ile Ile Asn Ile Ile Ala Glu
            115                 120                 125

Thr Glu Leu Arg Tyr Phe Ala Asn Asn Asn Gly Leu Val Tyr Gly Lys

```
                130                 135                 140
Asp Ile Tyr Phe Asp Asp Asn Pro Met Asn Leu Ser Tyr Ile Leu Asn
145                 150                 155                 160

Phe Asn Arg Glu Leu Glu Gly Ile Met Ser Arg Arg Phe Asp Gly Ala
                165                 170                 175

Phe Pro Ser Thr Val Asn Pro Ile Leu Ile Trp Glu Ile Lys Glu Tyr
                180                 185                 190

Tyr Tyr Thr Thr Thr Phe Gly Ser Arg Ile Ala Asp Gly Val Tyr Glu
                195                 200                 205

Thr Gln Leu Asp Gly Tyr Glu Ile Lys Thr Ile Arg Glu Glu Thr Asn
                210                 215                 220

Lys Asn Ile Gln His Ile Tyr Phe Ile Asp Asp Tyr Asn Thr Trp Trp
225                 230                 235                 240

Asn Met Gly Lys Ser Tyr Leu Cys Arg Ile Ile Asp Met Leu His Met
                245                 250                 255

Gly Leu Val Asp Glu Val Ile Met Gly Lys Glu Val Phe Glu Arg Trp
                260                 265                 270

Pro Gln Ile Leu Arg Ala Val Leu Asn Gln Tyr Tyr Lys
                275                 280                 285

<210> SEQ ID NO 13
<211> LENGTH: 223
<212> TYPE: PRT
<213> ORGANISM: Bacillus globigii

<400> SEQUENCE: 13

Met Lys Ile Asp Ile Thr Asp Tyr Asn His Ala Asp Glu Ile Leu Asn
1               5                   10                  15

Pro Gln Leu Trp Lys Glu Ile Glu Glu Thr Leu Leu Lys Met Pro Leu
                20                  25                  30

His Val Lys Ala Ser Asp Gln Ala Ser Lys Val Gly Ser Leu Ile Phe
                35                  40                  45

Asp Pro Val Gly Thr Asn Gln Tyr Ile Lys Asp Glu Leu Val Pro Lys
50                  55                  60

His Trp Lys Asn Asn Ile Pro Ile Pro Lys Arg Phe Asp Phe Leu Gly
65                  70                  75                  80

Thr Asp Ile Asp Phe Gly Lys Arg Asp Thr Leu Val Glu Val Gln Phe
                85                  90                  95

Ser Asn Tyr Pro Phe Leu Leu Asn Asn Thr Val Arg Ser Glu Leu Phe
                100                 105                 110

His Lys Ser Asn Met Asp Ile Asp Glu Glu Gly Met Lys Val Ala Ile
                115                 120                 125

Ile Ile Thr Lys Gly His Met Phe Pro Ala Ser Asn Ser Ser Leu Tyr
                130                 135                 140

Tyr Glu Gln Ala Gln Asn Gln Leu Asn Ser Leu Ala Glu Tyr Asn Val
145                 150                 155                 160

Phe Asp Val Pro Ile Arg Leu Val Gly Leu Ile Glu Asp Phe Glu Thr
                165                 170                 175

Asp Ile Asp Ile Val Ser Thr Thr Tyr Ala Asp Lys Arg Tyr Ser Arg
                180                 185                 190

Thr Ile Thr Lys Arg Asp Thr Val Lys Gly Lys Val Ile Asp Thr Asn
                195                 200                 205

Thr Pro Asn Thr Arg Arg Arg Lys Arg Gly Thr Ile Val Thr Tyr
                210                 215                 220
```

<210> SEQ ID NO 14
<211> LENGTH: 288
<212> TYPE: PRT
<213> ORGANISM: Bacillus stearothermophilus

<400> SEQUENCE: 14

```
Met Ile Lys Asn Phe Arg Asp Tyr Gln Arg Val Ala Ala Lys Tyr Ile
1               5                   10                  15

Thr Phe Ile Glu Ser Glu Phe Tyr Pro Asp Tyr Leu Asp Asn Ala Arg
            20                  25                  30

Phe Leu Tyr Gly Glu Val Leu Asn Lys Phe Tyr Glu Leu Val Asn Ser
        35                  40                  45

Ser Ser Ser Ser Ile Glu Leu Leu Glu Asn Ile Ser Lys Thr Lys Asp
    50                  55                  60

Pro Val Arg Thr Gln Leu Leu Arg Ile Phe Arg Lys Tyr Val Ser Pro
65                  70                  75                  80

Asp Thr Ser Val Glu Met Leu Lys Arg Lys Gln Arg Ile Pro Asp Ile
                85                  90                  95

Ile Lys Glu Phe Gly Thr Arg Phe Arg Asp Ile Lys Ile Val Arg Gln
            100                 105                 110

Lys Ile Ala Thr Arg Asn His Pro Asp Glu Thr Ile Met Ala Leu Leu
        115                 120                 125

Tyr Glu Tyr Lys Asp Arg Gly Lys Lys Gly Tyr Glu Leu Thr Asp Ala
    130                 135                 140

Phe Phe Thr Trp Phe Glu Gln Lys Phe Pro Asn Tyr Glu Ile Ile Gly
145                 150                 155                 160

Pro Arg Gly Ala Gly Lys Asp Ile Leu Leu Asn Glu Val Leu Pro Gly
                165                 170                 175

Phe Pro Ser Lys Ile Pro Ala Asp Phe Leu Ile Tyr Arg Arg Ser Asp
            180                 185                 190

Lys Thr Pro Ile Val Val Gly Phe Ala Arg Tyr Asp Ser Asp Arg Gly
        195                 200                 205

Gly Ala Gln Glu Asp Asp Arg Thr Gly Gly Asn Arg Asp Lys Ile Thr
    210                 215                 220

Glu Ile Lys Lys Tyr Ala Ala Glu His Asn Ile Pro Leu Lys Ile Leu
225                 230                 235                 240

Phe Leu Asn Asp Gly Pro Gly Leu Leu Leu Gly Ser Met Trp Asn Asp
                245                 250                 255

Tyr Ser Ala Leu Glu Asp Tyr Gly Glu Gly Cys Val Met Val Cys Thr
            260                 265                 270

Leu Lys Met Leu Glu Glu Arg Phe Thr Ile Asp Trp Leu Glu Asn Leu
        275                 280                 285
```

<210> SEQ ID NO 15
<211> LENGTH: 364
<212> TYPE: PRT
<213> ORGANISM: Bacillus aneurinolyticus

<400> SEQUENCE: 15

```
Met Glu Gln Val Thr Ile Asn His Glu Leu Ala Leu Leu Val Leu Glu
1               5                   10                  15

Gln Ala Phe Leu Thr Ala Asn Ser Gly Asp Tyr Thr Pro Ser Ser Leu
            20                  25                  30

Phe Ala Asp Ala Ile His Thr Val Leu Phe Asn Thr His Leu Thr Phe
        35                  40                  45
```

```
Leu Tyr Ile Leu Val Asn Ala Leu Ala Leu Ala Ser Phe Pro Gln
 50                  55                  60

Ile Asn Pro Ile Cys Leu Gln Leu Leu Ser Thr Leu Ser Gly Ala Tyr
 65                  70                  75                  80

Asp Ala Arg Ser Leu Cys His Leu Val Leu Val Pro Phe Glu Arg Asn
                 85                  90                  95

Asn Leu Asn Gly Ala Leu Gly Asn Ser Asn Glu Pro Phe Leu Asn Leu
            100                 105                 110

Pro Ala Arg Phe Thr Glu Leu Ser Pro Leu Asn Ala Val Arg Leu Gly
        115                 120                 125

Arg Asp Ser Met Leu Leu Asn Leu Leu Cys Asp Phe Leu Pro Gln Ile
130                 135                 140

Asn Ser Gln Asn Glu Ala Phe His Ser Leu Thr Asp Ala Leu Phe Tyr
145                 150                 155                 160

Ala Leu Gln Leu Ala Leu Asn Leu Gln Gln Leu Phe Asn Phe Thr Ser
                165                 170                 175

Ile Leu Thr Pro Thr Tyr Thr Asp Ile Glu Ile Phe Ile Leu Glu Leu
            180                 185                 190

Leu Glu Glu Ser Tyr Gly Gly Glu Cys Leu Ala Leu Ala Ile Gly Thr
        195                 200                 205

Leu Leu Leu Leu Leu Ser Glu Thr Ile Ile Gly Glu Asn Arg Val Glu
210                 215                 220

Val His Val Val Asn Gln Ser Gly Ala Ser Ser Leu Glu Val Asn Asp
225                 230                 235                 240

Ile Asp Val Tyr His Glu Asp Glu Ile Leu Tyr Thr Ile Glu Ala Leu
                245                 250                 255

Asp Leu His Tyr Ser Gln Gln Asp Val Glu His Ala Val Arg Leu Thr
            260                 265                 270

Ala Glu Ala Gly Cys Asp Arg Leu Thr Phe Ile Thr Gly Pro Arg Ala
        275                 280                 285

Leu Phe Asp Gly Ser His Thr Pro Leu Val Leu Ser Ala Ser Leu Leu
290                 295                 300

Gly Val Tyr Leu Thr Phe Thr Ser Tyr Glu Ala Phe Thr Leu Asn Ile
305                 310                 315                 320

Leu Ser Leu Ile Leu Pro Leu Thr Ala Asn Asp Phe Phe Leu Leu Leu
                325                 330                 335

Met His Thr Cys Asp Glu Ala Arg Val Leu Glu Thr Leu Asn His
            340                 345                 350

Val Ile Leu Thr Ala Arg Asn His Gln Leu Ile Glu
        355                 360

<210> SEQ ID NO 16
<211> LENGTH: 272
<212> TYPE: PRT
<213> ORGANISM: Pyrococcus species

<400> SEQUENCE: 16

Met Val Arg Asn Leu Val Ile Asp Ile Thr Lys Lys Pro Thr Gln Asn
 1               5                  10                  15

Ile Pro Pro Thr Asn Glu Ile Ile Glu Glu Ala Ile Thr Glu Leu Asn
                20                  25                  30

Val Asp Glu Leu Leu Asp Arg Leu Phe Glu Lys Asp Glu Ser Gly Glu
            35                  40                  45

Val Ile Thr Pro Ser Arg Ile Ala Lys Met Leu Glu Glu Lys Ala Phe
        50                  55                  60
```

```
Glu Ile Tyr Lys Glu Tyr Glu Lys Gln Val Arg Ala Tyr Leu Ser
 65                  70                  75                  80

Ala Gly Tyr Ser Arg Glu Lys Leu Glu Gln Ser Phe Gln Gln Ala Arg
                 85                  90                  95

Phe Ser Arg Gly Gly Lys Ala Phe Glu Ile Ile Phe Thr Lys Leu Leu
            100                 105                 110

Asn Lys Phe Gly Ile Arg Tyr Glu His Asp Arg Val Ile Lys Ile Tyr
            115                 120                 125

Asp Tyr Ile Thr Glu Gly Lys Pro Asp Phe Ile Ile Pro Ser Val
        130                 135                 140

Arg Ala Phe Leu Asn Asp Pro Ser Ser Ala Ile Leu Ile Thr Val Lys
145                 150                 155                 160

Arg Lys Val Arg Glu Arg Trp Arg Glu Ala Val Gly Glu Ala Gln Ile
                165                 170                 175

Leu Arg Asn Lys Phe Gly Asp Glu Ile Asn Phe Trp Phe Val Gly Phe
            180                 185                 190

Asp Glu Glu Phe Thr Ile Tyr Ser Ala Ile Ala Met Leu Asp Asn Gly
            195                 200                 205

Ile Asp Arg Val Tyr Val Ile Asp Gly Arg Tyr Asp Ser Leu Ile Glu
    210                 215                 220

Glu Ile Lys Arg Ile Ser Asp Pro Asn Phe Asn Glu Asp Lys Tyr Ile
225                 230                 235                 240

Gln Lys Ile Arg Arg Phe Ser Asp Ile Phe Asp Asp Ile Ile Gln Phe
                245                 250                 255

Leu Asn Lys His Gly Asn Lys Lys Arg Gly Lys Gln Leu Thr Leu Val
            260                 265                 270

<210> SEQ ID NO 17
<211> LENGTH: 188
<212> TYPE: PRT
<213> ORGANISM: Sphaerotilus natans

<400> SEQUENCE: 17

Met Ser Ile Asp Pro Asn Lys Leu Asn Ser Ala Leu Tyr Ala Ile Leu
  1               5                  10                  15

Gly Gly Tyr Arg Gly Lys Phe Ser Asn Lys Val Tyr Asn Gly Glu Asn
                 20                  25                  30

Asp Glu Phe Asp Ile Leu Met Glu Ile Phe Gly Ile Ser Pro Leu Leu
             35                  40                  45

Lys Arg Glu Ser Arg Gln Tyr Trp Gly Arg Glu Leu Gly Met Cys Trp
 50                  55                  60

Pro Arg Leu Val Val Glu Ile Cys Lys Gln Thr Arg Asn Asp Phe Gly
 65                  70                  75                  80

Ser Ala Leu Gln Ile Asp Gly Gly Pro Cys Asp Leu Ile Val Gly
                 85                  90                  95

Gly Leu Ala Ile Glu Thr Lys Tyr Arg Ile Gly Ser Gly Asp Ala Gly
            100                 105                 110

Thr Leu Lys Lys Phe Gln Ala Tyr Gly Ser Leu Leu Ser Ser Met Gly
            115                 120                 125

Tyr Glu Pro Val Leu Leu Ile Val Arg Glu Asp Asn Leu Gly Ala Ala
            130                 135                 140

Ile Thr Ala Cys His Ala Gly Gly Trp Thr Val Ile Thr Gly Gln Arg
145                 150                 155                 160

Thr Phe Asp Tyr Leu Arg Asp Leu Thr Gly Ile Asn Ile Lys Glu Leu
```

```
                    165                 170                 175
Leu Leu Gln Arg Ala Gly Lys Phe Pro Val Val Arg
                180                 185

<210> SEQ ID NO 18
<211> LENGTH: 465
<212> TYPE: PRT
<213> ORGANISM: Bacillus stearothermophilus

<400> SEQUENCE: 18

Met Ala Arg Glu Glu Arg Glu Trp His Pro Lys Phe Ile Glu Tyr Met
1               5                   10                  15

Asp Phe Ile Ile Gln His Pro Asn Tyr Lys Gly Leu Pro Ile Thr Lys
                20                  25                  30

Lys Ser Asp Gly Ser Trp Ser Phe Gly Thr Lys Lys Thr Gln Ile
            35                  40                  45

Gly Lys Ala Arg Ile Ala Trp Cys Glu Asn Lys Ala Lys Glu Leu Gly
        50                  55                  60

Phe Pro Ile Glu Pro Gly Val Tyr Ala Asn Val Met Arg Glu Ile His
65                  70                  75                  80

Pro Thr Lys Trp Lys Val Cys Gln Thr Cys Gly His Ser Met Ser Ile
                85                  90                  95

Tyr Tyr His Tyr Pro Ser Ala Asn Phe Leu Lys Ala Leu Lys Lys Glu
                100                 105                 110

Phe Gly Val Glu Tyr Thr Glu Val Asp His Ile Ala Asp Ile Trp Asp
            115                 120                 125

Asp Leu Leu Ser Arg Gly Phe Ser Asn Asn Lys Ile Ala Ser Phe Leu
        130                 135                 140

Ile Lys Lys Gly Glu Leu Asp Leu Asn Ala Lys Thr Ser Ser Lys Asp
145                 150                 155                 160

Glu Val Ile Tyr Glu Leu Glu Ser Val Cys Arg Asn Lys Gly Lys Lys
                165                 170                 175

Ile Leu Ser Pro Gly Ala Met Ser Asn Phe Pro Asp Arg Phe Asp Gly
            180                 185                 190

Phe His Thr Tyr Asn Arg Cys Cys Arg Ala Ser Gln Asp Lys Gly Arg
        195                 200                 205

Ser Lys Glu Asn Leu Lys Ser Tyr Thr Lys Asp Arg Arg Ala Tyr Glu
    210                 215                 220

Tyr Trp Ser Asp Gly Asn Ile His Ala Ala Asn Gln Phe Met Gly Ser
225                 230                 235                 240

Pro Phe Phe Asn Asn Ile Ser Ala Asp His Ile Gly Pro Ile Ser Leu
                245                 250                 255

Gly Phe Val His Asp Pro Arg Tyr Leu Gln Pro Met Ser Gly Gly Asp
            260                 265                 270

Asn Ser Ser Lys Arg Asp Arg Leu Gln Leu Asp Ile Glu Lys Ile
        275                 280                 285

Ile Glu Thr Glu Lys Arg Thr Asn Val Tyr Pro Met Ser Trp Tyr Ser
    290                 295                 300

Lys Leu Ile Trp Glu Tyr Ile Lys Lys Asn Tyr Ser Thr His Lys Ser
305                 310                 315                 320

Leu Ile Ser Gly Val Tyr Arg Asp Ala Leu Lys Gln Asn Met Ser Asn
                325                 330                 335

Phe Met Tyr Ile Leu Trp Tyr Leu Glu His Cys Asn Gln Asp Gly
            340                 345                 350
```

```
Glu His Phe Leu Glu Ala Leu Leu Lys Pro Asn Tyr Asp Tyr Phe
        355                 360                 365

Gln Tyr Ser Tyr Thr Phe Asn Glu Leu Gly Ile Val Ser Ile Asn
    370                 375                 380

Pro Arg His Phe Thr Asp Arg Asn Gln Tyr Glu Thr Glu Arg Tyr Lys
385                 390                 395                 400

Arg Ile Ala Phe Glu Ser Val Tyr Asp Tyr Asn Glu Lys Glu Asn Arg
                405                 410                 415

Asn Ile Lys Ala Asn Leu Ile Asp Asn Glu Gln Arg Met Leu Asn Lys
                420                 425                 430

Leu Cys Gln Glu Ile Ser Ser Gly Val Pro Val Glu Gln Cys Lys Lys
            435                 440                 445

Leu Leu Ile Glu Leu Met Glu Val Ile Gln Lys Arg Ile Ile Ser Thr
        450                 455                 460

Leu
465

<210> SEQ ID NO 19
<211> LENGTH: 383
<212> TYPE: PRT
<213> ORGANISM: Bacillus stearothermophilus

<400> SEQUENCE: 19

Met Ala Ile Thr Leu Cys Asp Ile Asn Gly Cys Arg Leu Glu Arg Gly
1               5                   10                  15

His Thr Gly Lys His Asn Lys Phe Pro Glu Phe Val Trp Thr Ser Gln
            20                  25                  30

Phe Asn Lys Lys Asp Ile Asp Lys Val Asn Lys Ala Gly Tyr Ala Thr
        35                  40                  45

Pro Arg Gly Gly Asp Lys Gly Ala Tyr Gln Asn His Val Tyr Arg Asn
    50                  55                  60

Asn Lys Val Ile Ile Pro Phe Glu Arg Leu Glu Asn Val Asn Leu Asn
65                  70                  75                  80

Asn Tyr Gln Asp Gly Tyr Val Ile Arg Leu Phe Pro Asn Gln Tyr Phe
                85                  90                  95

Glu Ser Ala Gly Val Val Lys Pro Glu Phe Leu Gln Pro Asn Ser Phe
            100                 105                 110

Val Lys Val Gly Asp Asn Ala Phe Ile Leu Tyr Arg Thr His Ser Ser
        115                 120                 125

Phe Glu Glu Leu Pro Pro Leu Pro Asp Trp Glu Val Arg His Leu Lys
    130                 135                 140

Lys Asn Gly Asn Ile Val Thr Arg Arg Ser Lys Asp Val Ile Asp Ala
145                 150                 155                 160

Gly His Tyr Val Leu Arg Leu Ser Ser Ile Ser Asn Lys Lys Glu Arg
                165                 170                 175

Lys Glu Gly Pro Pro Gln Gly Ile Phe Ala Pro Glu Tyr Ala Asn Ala
            180                 185                 190

Glu Thr Asn Tyr Leu Ser Lys Ala Phe Leu Ala Trp Leu Ile Ile Lys
        195                 200                 205

Thr Gln Asn Ser Pro Tyr Asn Glu Glu Gln Phe Gln His Leu Arg Ala
    210                 215                 220

Ile Leu Ile Ser His Asn Leu Ile Asn Ile Ser Gln Leu Glu Glu Lys
225                 230                 235                 240

Ala Ile Leu Lys Asn Gly Ile Thr Cys Cys Pro Leu Cys Glu Gln Ile
                245                 250                 255
```

```
Ile Phe Tyr Glu Gln Leu His Glu Met Val Ser Phe Glu Gly Ala Ser
            260                 265                 270

Gly Leu Ala Asn Ser Gln Glu Val Glu Gly Ala Thr Arg Ser Thr
        275                 280                 285

Ser Val Asn Leu Phe His Met Val Pro Leu Val Tyr Glu Thr Leu Glu
290                 295                 300

His Lys Pro Asp Gln Ile Ala Trp Gly His Ala Ile Cys Asn Thr Arg
305                 310                 315                 320

Leu Gly Gln Arg Glu Cys Leu Pro Leu Ser Arg Leu Lys Gln Glu Gly
                325                 330                 335

Thr Pro Val Gly Leu Leu Asp Glu Asp Ser Asn Leu Glu Val Leu Gly
            340                 345                 350

Trp Ile Ser Lys Asp Lys Gln Phe Ile Arg Thr Glu Asn Gly Glu Val
        355                 360                 365

Trp Ile Lys Ile Thr Asp Ile Glu Phe Asn Asp Asp Phe Glu Glu
    370                 375                 380

<210> SEQ ID NO 20
<211> LENGTH: 269
<212> TYPE: PRT
<213> ORGANISM: Streptomyces fimbriatus

<400> SEQUENCE: 20

Met His Gln Asp Tyr Arg Glu Leu Ser Leu Asp Glu Leu Glu Ser Val
1               5                   10                  15

Glu Lys Gln Thr Leu Arg Thr Ile Val Gln Ala Leu Gly Gln Tyr Ser
            20                  25                  30

Lys Glu Ala Lys Ser Ile Phe Glu Thr Thr Ala Ala Asp Ser Ser Gly
        35                  40                  45

Glu Val Ile Val Leu Ala Glu Asp Ile Thr Gln Tyr Ala Leu Glu Val
    50                  55                  60

Ala Glu Thr Tyr Pro Ile Asn Arg Arg Phe Ala Gly Phe Ile Asp Tyr
65                  70                  75                  80

Lys Arg Val Arg Trp Leu Pro Ser Pro His Gly Leu Leu Pro Gln Val
                85                  90                  95

Leu Leu Val Asp Ala Lys Ala Ser Thr Glu Lys Asn Arg Asp Thr Leu
            100                 105                 110

Gln Arg Ser Gln Leu Pro Met Asp Ala Glu Phe Arg Asn Thr Ser Ser
        115                 120                 125

Gly Glu Val Val Thr Met Glu Ala Gly Val Ile Pro His Leu Met Leu
    130                 135                 140

Gln Ser Ala Asn Asp Gly Val Leu Pro Ala Val Thr Thr Ser Ile Phe
145                 150                 155                 160

Val His Phe Tyr Tyr Arg Glu Leu Lys Asp Val Glu Gly Arg Tyr Arg
                165                 170                 175

Glu Leu Lys Ser Ile Tyr Val Leu Ser Leu Pro His Ala Arg Leu Lys
            180                 185                 190

Gln Arg Tyr Asn Pro Asp Pro Asp Thr Ser Phe Phe Gly Ala Gly Lys
        195                 200                 205

His Ser Pro Ala Arg Gly Glu Val Ala Arg Ile Arg Val Tyr Phe Asp
    210                 215                 220

Arg Leu Lys Glu Ala Cys Pro Trp Arg Leu Gln Glu Leu His Tyr Ser
225                 230                 235                 240

Ala Asp Ser Glu Tyr Thr Gln Pro Arg Trp Arg Asp Leu Asn Asp Ala
```

```
                        245                 250                 255
Gly His Glu Val Thr Lys Glu Phe Leu Phe Leu Glu Arg
            260                 265

<210> SEQ ID NO 21
<211> LENGTH: 231
<212> TYPE: PRT
<213> ORGANISM: Pseudomonas mendocina

<400> SEQUENCE: 21

Met Thr Thr Asn Ser Pro Ser Asp Val Gly Met Ile Asp Glu Cys Leu
1               5                   10                  15

Ser Ile Val Arg Thr Ser Leu Ala Arg Cys Phe Gln Gln Gln Ala Pro
            20                  25                  30

Ser Ile Gln Ala Ser Trp Pro Leu Ser Gly Arg Ala Val Ser Glu Ile
        35                  40                  45

Gly Gly Arg Leu Val Glu Ser Phe Val Leu Ala Arg Leu Pro His Glu
    50                  55                  60

Leu Ser Thr Thr Pro Phe Asp Gly Gln Ile Leu Cys Glu Ile Pro Glu
65                  70                  75                  80

Ser Gly Arg Ala Met Glu Asp Ile Ala Val Thr Phe Ile Gly Pro His
                85                  90                  95

Gly Arg Ala Arg Leu Leu Ile Asp Val Lys Gly His Asn Glu Tyr Arg
            100                 105                 110

Thr Gly Ser Arg Pro Asn Leu Ala Ser Ile Arg Lys Cys Leu Glu Leu
        115                 120                 125

Tyr Arg Ser Ser His Thr Val Asp Glu Leu Val Val Phe Phe Cys
    130                 135                 140

Arg Tyr Arg Pro Ser Val His Pro Asp His His Ala Gln Ala Val Glu
145                 150                 155                 160

Tyr His Val Leu Pro Glu Ser Phe Asn Glu Gln Gly Leu Phe Leu Leu
                165                 170                 175

Arg Ala Leu Ser Glu Ser Asn Leu Asp Pro Ala Asn Ile Gly Ser Gly
            180                 185                 190

Gly Gln Leu Leu Leu Ala Arg Glu Asn Asn Ile Arg Leu Val Asn Arg
        195                 200                 205

Ser Arg Ser Glu Phe Val Gln Leu Leu Glu Gly Leu Gln Ser Arg Leu
    210                 215                 220

Gln Arg Gly Arg Ser Thr Val
225                 230

<210> SEQ ID NO 22
<211> LENGTH: 247
<212> TYPE: PRT
<213> ORGANISM: Serratia marcescens

<400> SEQUENCE: 22

Met Ser Arg Asp Asp Gln Leu Phe Thr Leu Trp Gly Lys Leu Asn Asp
1               5                   10                  15

Arg Gln Lys Asp Asn Phe Leu Lys Trp Met Lys Ala Phe Asp Val Glu
            20                  25                  30

Lys Thr Tyr Gln Lys Thr Ser Gly Asp Ile Phe Asn Asp Phe Phe
        35                  40                  45

Asp Ile Phe Gly Asp Arg Leu Ile Thr His His Phe Ser Ser Thr Gln
    50                  55                  60

Ala Leu Thr Lys Thr Leu Phe Glu His Ala Phe Asn Asp Ser Leu Asn
```

```
                65                  70                  75                  80
Glu Ser Gly Val Ile Ser Ser Leu Ala Glu Ser Arg Thr Asn Pro Gly
                    85                  90                  95
His Asp Ile Thr Ile Asp Ser Ile Lys Val Ala Leu Lys Thr Glu Ala
                100                 105                 110
Ala Lys Asn Ile Ser Lys Ser Tyr Ile His Val Ser Lys Trp Met Glu
            115                 120                 125
Leu Gly Lys Gly Glu Trp Ile Leu Glu Leu Leu Glu Arg Phe Leu
130                 135                 140
Glu His Leu Glu Asn Tyr Glu Arg Ile Phe Thr Leu Arg Tyr Phe Lys
145                 150                 155                 160
Ile Ser Glu Tyr Lys Phe Ser Tyr Gln Leu Val Glu Ile Pro Lys Ser
                165                 170                 175
Leu Leu Leu Glu Ala Lys Asn Ala Lys Leu Glu Ile Met Ser Gly Ser
                180                 185                 190
Lys Gln Ser Pro Lys Pro Gly Tyr Gly Tyr Val Leu Asp Glu Asn Glu
            195                 200                 205
Asn Lys Lys Phe Ser Leu Tyr Phe Asp Gly Gly Ala Glu Arg Lys Leu
210                 215                 220
Gln Ile Lys His Leu Asn Leu Glu His Cys Ile Val His Gly Val Trp
225                 230                 235                 240
Asp Phe Ile Leu Pro Pro
                245

<210> SEQ ID NO 23
<211> LENGTH: 345
<212> TYPE: PRT
<213> ORGANISM: Acetobacter aceti

<400> SEQUENCE: 23

Met Asn Pro Asp Glu Val Phe Ser Asp Phe Gln Arg Gly Phe Phe Gly
1               5                   10                  15
Arg Lys Phe Thr Ala Gly Leu Leu Val Ser Phe Ile Asp Leu Met Ser
            20                  25                  30
Glu Leu Glu Thr Pro Lys Leu Gly Ile Ala Asp Phe Asp Gly Phe Leu
        35                  40                  45
Lys Leu Phe Pro Arg Gln Leu Lys Thr Ser Ala Gly Lys Arg Ala Asn
    50                  55                  60
Thr Leu Ile Val Glu Lys Glu Asp Gly Lys Thr Ile Ser Leu Arg Lys
65                  70                  75                  80
Phe Tyr Asn Ser Ile Glu Lys Phe Tyr Arg Ala Glu His Lys Arg Phe
                85                  90                  95
Asp Tyr Pro Ser Ala Ala Pro His Ala Thr Gln Ala Trp Ala Asp Tyr
            100                 105                 110
Lys Thr Trp Leu Asp Ala Leu Val Thr Phe Ser Glu Glu Gln Leu Gly
        115                 120                 125
Glu Leu Arg Gly Arg Val Asn Gln Phe Val Leu Asp Thr Leu Lys Ser
    130                 135                 140
Gln Glu Phe Asp Pro Thr Ser Val Lys Val Glu Pro Pro Leu Phe Arg
145                 150                 155                 160
Ile Leu Leu Glu Lys Phe Glu Met Thr Ala Gln Lys Gly Glu Pro Thr
                165                 170                 175
Gly Ala Ser Phe Gln Gly Ile Val Phe Gly Phe Leu Arg Ala Asp Asn
            180                 185                 190
```

```
Pro His Leu Gln Ile Glu Ile Asp Lys Val Arg Thr Gly Ser Lys Arg
            195                 200                 205

Leu Gln Arg Ile Gly Asp Val Asp Gly Trp Glu Gly Glu Arg Leu Ala
        210                 215                 220

Ile Ser Ala Glu Val Lys Gln Tyr Glu Ile Asn Thr Glu Ser Ile Asp
225                 230                 235                 240

Asp Leu Ala Asp Phe Ala Asn Arg Thr Gly Gln Arg Gly Ala Leu Gly
                245                 250                 255

Val Ile Ala Ala Leu Ser Phe Ser Glu Ala Lys Pro Leu Leu Glu
            260                 265                 270

Asn Met Gly Leu Ile Ala Leu Asp Lys Glu Gly Met Leu Lys Ile Val
        275                 280                 285

Glu Leu Trp Asp Pro Val Lys Gln Arg Thr Ala Val Ser Ser Phe Ile
290                 295                 300

Tyr Tyr Ala Thr His Val Glu Lys Asn Ser Ser Leu Ser Ala Arg Leu
305                 310                 315                 320

Asn Ile Phe Leu Glu Ala Ser Ala Ser Glu Trp Ala Glu Gln Arg Gln
                325                 330                 335

Ala Ala Ile Leu Pro Gln Ser Glu Ser
            340                 345

<210> SEQ ID NO 24
<211> LENGTH: 237
<212> TYPE: PRT
<213> ORGANISM: Arthrobacter protophormiae

<400> SEQUENCE: 24

Met Ala Gln Lys Ala Arg Leu Arg Gln Asn Arg Tyr Gly Thr Val Ile
1               5                   10                  15

Asn Thr Thr Ser Ser Lys Gln Glu Leu Gln Leu Gly Asp Ala Leu Val
                20                  25                  30

Asp Ala Thr Glu Arg Leu Thr Ala Lys Phe Gly Ile Ala Phe Thr His
            35                  40                  45

Glu Lys Lys Val Met Leu Ala Asp Ile Val Thr Ser Leu Arg Arg Ser
50                  55                  60

Phe Pro Thr Val Ser Phe Asp Asp Pro Leu Pro Asn Thr Tyr Met Ser
65                  70                  75                  80

Pro Asp Gly Gly Ile Leu Ser Ile Met Ala Ala Asp Gly Glu Arg Thr
                85                  90                  95

Phe Pro Val Leu Ile Thr Glu Val Lys Asn Gln Gly Thr Asn Asp Leu
            100                 105                 110

Arg Ala Gln Glu Gly Leu Lys Lys Gln Ala Met Gly Asn Ala Ile Glu
        115                 120                 125

Arg Leu Gly Lys Asn Val Ile Gly Phe Arg Ala Met Met Leu Glu Asp
    130                 135                 140

Gly Ile Ile Pro Phe Val Cys Phe Gly Tyr Gly Trp Asp Phe His Glu
145                 150                 155                 160

Gly Ser Ser Ile Leu Asp Arg Val Lys Thr Ile Ala Met Phe Gly Glu
                165                 170                 175

Leu Asn Gln Val Asn Val Ile Pro Glu Gly Glu Gly Leu Phe Asn
            180                 185                 190

Arg Gly Ser Phe Phe Arg Met Glu Pro Trp Ser Leu Glu Glu Met
        195                 200                 205

Ser Asp Val Met Phe Asp Val Gly Ser Arg Ala Ile His Tyr Tyr Phe
210                 215                 220
```

```
Ala Lys Phe Gly Asp Ser Ala Phe Lys Met Ile Gly Ser
225                 230                 235

<210> SEQ ID NO 25
<211> LENGTH: 530
<212> TYPE: PRT
<213> ORGANISM: Bacillus stearothermophilus

<400> SEQUENCE: 25

Met Ala Lys Tyr Gly Arg Gly Lys Phe Leu Pro His Gln Asn Tyr Ile
1               5                   10                  15

Asp Tyr Met His Phe Ile Val Asn His Lys Asn Tyr Ser Gly Met Pro
            20                  25                  30

Asn Ala Ile Gly Glu Asp Gly Arg Ile Asn Trp Gln Val Ser Ser Gly
        35                  40                  45

Lys Thr Thr Ser Phe Tyr Glu Tyr Tyr Gln Ala Arg Phe Glu Trp Trp
    50                  55                  60

Glu Lys Lys Ala Asp Glu Leu Asn Leu Pro Gly Thr Gly Asn Ser Asn
65                  70                  75                  80

Lys Arg Phe Ser Leu Ala Ala Arg Leu Ile His Pro Thr Gly Gln Arg
                85                  90                  95

Pro Cys Arg Leu Cys Gly Lys Tyr Gln Tyr Val Gly Tyr Met Tyr Val
            100                 105                 110

Ser His Asn Leu Tyr Lys Arg Trp Ser Lys Ile Thr Gly Arg Glu Asp
        115                 120                 125

Leu Phe Phe Lys Lys Gln Asn Ile Ile Glu Ala Ala Asn Ile Phe Lys
    130                 135                 140

Ser Ile Met Gly Glu Gln Ala Leu Ile Asn Glu Leu Thr Thr Ile Phe
145                 150                 155                 160

Pro Glu Arg Lys Asp Tyr Phe Asn Arg Leu Pro Asn Ile Glu Asp Phe
                165                 170                 175

Phe Val Ser Ser Ser His Ile Lys Asn Asn Gly Asn Tyr Ile Ser Pro
            180                 185                 190

Gly Phe Met Ala Asn Pro Pro Asp Arg Leu Asp Gly Phe His Asp Tyr
        195                 200                 205

Gly Ile Cys Cys Arg Lys Glu Lys Asp Pro Gly Arg His Asp Asp Asn
    210                 215                 220

Met Arg Leu Tyr Asn His Asp Arg Arg Ala Phe Met Trp Trp Ser Glu
225                 230                 235                 240

Gly Asp Trp Ala Leu Ala Asp Ala Leu Tyr Asn Lys Ala Gly Ala Gly
                245                 250                 255

Lys Cys Ala Asp Pro Asp Cys Gln Lys Glu Val Glu Lys Ile Ser Pro
            260                 265                 270

Asp His Val Gly Pro Ile Ser Cys Gly Phe Lys Gln Ile Pro Phe Phe
        275                 280                 285

Lys Pro Leu Cys Ala Ser Cys Asn Ser Ala Lys Asn Arg Arg Phe Ser
    290                 295                 300

Tyr Gln Asp Val Lys Glu Leu Leu Lys Tyr Glu Asn Tyr Thr Gly Asp
305                 310                 315                 320

Ser Val Ala Ser Trp Gln Val Arg Ala Leu Trp Asp Asn Cys Lys His
                325                 330                 335

Leu Val Lys Asn Asp Asp Asp Ser Lys Leu Leu Ser Asn Leu Met Arg
            340                 345                 350

Ser Leu Gln Asp Tyr Tyr Leu Arg Ser Leu Tyr Lys Leu Phe Ser Asn
```

```
              355                 360                 365
Gly Phe Ala His Leu Leu Ser Tyr Phe Leu Thr Pro Glu Tyr Ala His
 370                 375                 380

Tyr Lys Ile Thr Phe Glu Gly Leu Asn Thr Ser Thr Leu Glu Tyr Glu
385                 390                 395                 400

Arg Tyr Tyr Lys Thr Phe Lys Lys Thr Lys Ser Thr Ser Ser Leu Ala
                405                 410                 415

Ala Arg Ile Val Arg Ile Ala Phe Glu Glu Leu Glu Ile Tyr Asn Ser
            420                 425                 430

Lys Asp Ile Asn Glu Arg Lys Leu Ile Lys Phe Asp Thr Ser Ser Trp
        435                 440                 445

Glu Lys Asp Phe Glu Asn Ile Ile Ser Tyr Ala Thr Lys Asn Leu Ser
    450                 455                 460

Leu Asp Glu Glu Ala Ser Lys Trp Asn Lys Val Leu Thr Asp Lys Asn
465                 470                 475                 480

Leu Ser Ser Thr Glu Lys Asp Lys Lys Ile Ser Ser Leu Leu Glu Asp
                485                 490                 495

Lys Asn Tyr Glu Val Tyr Lys Lys Gln Phe Tyr Ile Leu Lys Asp Leu
            500                 505                 510

Leu Val Glu His Phe Asn Lys Ile Gly Glu Gln Ile Ala Lys Asp Tyr
        515                 520                 525

Met Lys
    530

<210> SEQ ID NO 26
<211> LENGTH: 246
<212> TYPE: PRT
<213> ORGANISM: Bacillus megaterium

<400> SEQUENCE: 26

Met Leu Lys Ile Glu Asp Ile Val Glu Ile Arg Lys Ala Ile Gly Arg
1               5                   10                  15

Pro Gly Tyr Glu Ile Val Phe Ser Lys Asp Lys Val Ile Trp Leu Thr
            20                  25                  30

Lys Arg Arg Thr Ile Ile Ser Leu Leu Leu Ile Lys Tyr Gly Ile
        35                  40                  45

Ser Ser Glu Ala Asp Leu Ala Arg Gly Ser Asn Arg Leu Leu Glu Val
    50                  55                  60

Lys Gly Ile Leu Lys Gly Lys Tyr Asn Glu Thr Trp Ile Asn Asp His
65                  70                  75                  80

Tyr Ala Asp Ala Asn Lys Pro Phe Ser Glu Leu Trp Asn Glu Glu Gly
                85                  90                  95

Phe Thr Trp Ile His Pro Ala Gln Glu Lys Leu Asn Gly Asn Gln Gln
            100                 105                 110

Tyr Val Leu Lys Pro Glu Asp His Asp Lys Leu Phe Ile Leu Ile Lys
        115                 120                 125

Lys Ala Phe Arg Thr Ser Leu Ser Ile Lys Glu Gln Asp Glu Val Met
    130                 135                 140

Lys Lys Gln Asn Gly Lys Cys Asn Leu Cys Gly Ser Ser Leu Leu Pro
145                 150                 155                 160

Lys Ser Lys Ile Gln Lys Asn Thr Tyr Ala Lys Asp Arg Val Arg Gly
                165                 170                 175

Val Phe Asp His Arg Ile Pro Val Glu Lys Gly Gly Asp Ser Thr Ile
            180                 185                 190
```

Asp Asn Tyr Gln Ala Leu Cys Phe Tyr Cys Asn Lys Ser Lys Trp Gln
            195                 200                 205

Ile Cys Asn Ile Cys His Leu Asp Asp Cys Asp Thr Asn Cys Val Leu
    210                 215                 220

Ala Thr Pro Glu Asn Asn Asn Ile Ile Ser Pro Thr Lys Glu Asp Ile
225                 230                 235                 240

Ser Asp Arg Leu Asn Arg
            245

<210> SEQ ID NO 27
<211> LENGTH: 236
<212> TYPE: PRT
<213> ORGANISM: Bacillus stearothermophilus

<400> SEQUENCE: 27

Met Met Asp Ile Lys Thr Phe Ile Lys Lys Leu Glu Glu Ile Lys Ala
1               5                   10                  15

Lys Gly Tyr Ile Arg Thr Leu Arg Arg Gly Asp Thr Gly Val Gly His
            20                  25                  30

Thr Leu Glu Gln Glu Leu Gly Leu Thr Glu Asn Asn Ile Ser Leu Pro
        35                  40                  45

Asp Leu Gly Val Ala Glu Leu Lys Ala Ala Arg Arg Asn Thr Ser Ser
    50                  55                  60

Met Leu Thr Leu Phe Thr Lys Glu Pro Leu Ser Asp Lys Gly Arg Lys
65                  70                  75                  80

Arg Asp Arg Tyr Leu Leu Glu Thr Phe Ala Tyr Asp Ser Asp Lys Glu
                85                  90                  95

Asp Arg Ile Lys Glu Leu Tyr Thr Thr Ile Ser Ala Leu Asp Tyr Asn
            100                 105                 110

Ala Gln Gly Phe Lys Leu Glu Val Thr Asn Lys Glu Ile Arg Leu Ile
        115                 120                 125

His Lys Asp Ile Pro Leu Asp Val Tyr Trp Thr Ala Glu Leu Leu Gln
    130                 135                 140

Lys Thr Phe Glu Asp Lys Leu Pro Ala Leu Val Tyr Val Tyr Ala Asp
145                 150                 155                 160

His Ile Gly Glu Asp Ala Asp Glu His Phe His Tyr Thr Glu Ala Arg
                165                 170                 175

Leu Leu Lys Gly Phe Asp Phe Lys Gly Phe Met Lys Ala Val Gln Asp
            180                 185                 190

Gly Tyr Ile Lys Val Asp Leu Arg Met His Met Lys Asn Asn Gly Arg
        195                 200                 205

Pro Arg Asn His Gly Thr Ala Phe Arg Ile Leu Arg Ser His Leu Pro
    210                 215                 220

Ile Cys Phe Lys Glu Gln Gln Ile Leu Val Lys Pro
225                 230                 235

<210> SEQ ID NO 28
<211> LENGTH: 276
<212> TYPE: PRT
<213> ORGANISM: Micrococcus luteus

<400> SEQUENCE: 28

Met Ser Ala Pro Glu Val Asp Ser Ala Arg Asp Ala Arg Tyr Val Glu
1               5                   10                  15

Ile Leu Leu Ala Pro Leu Arg Lys Cys Gly Thr Tyr Leu Pro Lys Met
            20                  25                  30

Gly Gly Ser Gly Glu Val Asp Leu Ala Gly Phe Thr Ala Ala Tyr Gly
            35                  40                  45

Ala Asp Pro Leu Tyr His Trp Met Gly Leu Asp Ser Pro Leu Met Phe
 50                  55                  60

Ala Ala His Lys Ala Ala Gly Met Thr Ser Ile Tyr Arg Gln Leu
 65                  70                  75                  80

Gly Ile Gly Ser Glu Arg Leu Phe Arg Gln Val Leu Arg Asp Glu Leu
                 85                  90                  95

Asn Leu Thr Ala Asp Gln Val Lys Trp Ser Tyr Lys Met Leu Pro Glu
            100                 105                 110

Leu Asp Ala Glu His Ala Asn Glu Ser Val Lys Ala Arg Val Leu Ser
        115                 120                 125

Leu Asp Gly Arg Val Glu Leu Glu Asp Leu Glu Asp Gln Gln Ala Arg
    130                 135                 140

Glu Arg Val Glu Ala Trp Ile Glu Val Gln Arg Arg Leu Asn Ile
145                 150                 155                 160

Thr Ala Pro Leu Lys Gly Ala Val Phe Glu Val Arg Gln Gly Tyr Lys
                165                 170                 175

Ser Ala Asp Ser Lys Arg Gln Asn Ala Asp Leu Ala Asn Ala Ala Gln
            180                 185                 190

Ala Leu Gly His Gln Tyr Leu Pro Val Leu Val Ile Met Ser Thr Gln
        195                 200                 205

Ile Asn Glu Val Val His Ala Arg Tyr Thr Thr Gly Asn Trp Ser Val
    210                 215                 220

Leu Met Gly Thr Val Gly Ala Ser Asp Pro Val Gly Ser Thr Tyr Asp
225                 230                 235                 240

Phe Leu Asp Gln Val Val Gly Tyr Asp Leu Ala Ala Phe Phe Glu Arg
                245                 250                 255

Asn Lys Ala Ala Leu Arg Ala Gly Thr Glu Gly Ile Leu Thr Asp Leu
            260                 265                 270

Leu Glu Ala Arg
        275

<210> SEQ ID NO 29
<211> LENGTH: 353
<212> TYPE: PRT
<213> ORGANISM: Bacillus aneurinolyticus

<400> SEQUENCE: 29

Met Ala Gln Leu Lys Tyr Asn Lys Asp Ile Asp Glu Leu Glu Arg Asn
1               5                  10                  15

Ala Ala Lys Trp Trp Pro Asp Phe Leu Ala Lys Lys Glu Ser Ser Thr
                20                  25                  30

Ser Ile Ile Pro Lys Leu Val Glu Ser Gln Asp Ala Phe Ile Ser Leu
            35                  40                  45

Leu Asn Leu Ser Lys Asn Asn Pro Phe Asp Ile Phe Gln Leu Ile Asp
        50                  55                  60

Ala Ser Lys Phe Pro Pro Asn Leu Phe Leu Lys His Leu Val Val Leu
65                  70                  75                  80

Thr Asp Phe Gly Gly Glu Pro Leu Asn Arg Leu Asn Gln Asn Phe Asp
                85                  90                  95

Ser Leu Phe Pro Met Ile Pro Tyr Gly Asn Pro Leu His Asn Lys Ser
            100                 105                 110

Val Arg Lys Phe Glu Phe Phe Trp Asn Glu Lys Lys Tyr Glu Tyr Val
        115                 120                 125

```
Phe Gln Glu Leu Pro Val Thr Ser Leu Thr Asn Ser Lys Leu Lys Ile
            130                 135                 140

Asp Gly Ala Ser Ile Ser Lys Thr Val Pro Leu Ser Asp Leu Tyr Lys
145                 150                 155                 160

Asp Val Ile Val Leu Leu Met Phe Gly Ala Asn Ala Val Asn Ser Glu
                165                 170                 175

Val Ser Glu Val Leu Arg Lys Cys Glu Val Gly Asn Leu Ile Gly Lys
                180                 185                 190

Thr Asp Glu Leu Lys Lys Phe Ile Lys Glu Arg Tyr Ile Phe Val Ser
            195                 200                 205

Arg Ile Thr Gly Gly Ala Glu Ala Asn Thr Leu Gly Gln Val Ala Gln
210                 215                 220

Thr His Val Ile Asp Phe Leu Arg Thr Arg Leu Gly Lys Gly Tyr Asp
225                 230                 235                 240

Ile Lys Ser Asn Gly His Ile Glu Gly Val Thr His Asn Asp Gly Gln
                245                 250                 255

Thr Leu Thr Thr Phe Asp Val Val Ile Lys Lys Gly Ser Lys Ser Val
            260                 265                 270

Ala Ile Glu Ile Ser Phe Gln Val Thr Thr Asn Ser Thr Ile Glu Arg
            275                 280                 285

Lys Ala Gly Gln Ala Lys Ala Arg Tyr Asp Met Val Ser Asp Thr Gly
290                 295                 300

Asn Tyr Ile Ala Tyr Ile Ile Asp Gly Ala Gly Asn Phe Gln Arg Lys
305                 310                 315                 320

Asn Ala Ile Thr Thr Ile Cys Asn Asn Ser His Cys Thr Val Ala Tyr
                325                 330                 335

Thr Glu Glu Glu Leu Asn Val Leu Leu Lys Phe Ile Leu Glu Lys Leu
            340                 345                 350

Glu

<210> SEQ ID NO 30
<211> LENGTH: 285
<212> TYPE: PRT
<213> ORGANISM: Kluyvera ascorbata

<400> SEQUENCE: 30

Met Ser Val Ile Pro Cys Lys Lys Asp Leu Gln Leu Lys Lys Leu Ile
1               5                   10                  15

Glu Ser Tyr Ala Glu Ala Leu Lys Val Glu Ala His Lys Leu Gly Glu
            20                  25                  30

His Gly Leu Thr Glu Ala Glu Phe Tyr Asp Ser Gly Leu Phe Arg Gly
        35                  40                  45

Ala Ile Glu Arg Ile Arg Gly Gln Phe Ser Ala Thr Met Arg Glu Lys
    50                  55                  60

Arg Asn Phe Val Lys His Val Leu Asn Tyr Met Gln Asp Asn Asp Tyr
65                  70                  75                  80

Ile Ala Asp Trp Glu Ser Ala Gly Glu Ser Asn Arg His Asp Tyr Met
                85                  90                  95

Val Thr Leu Asn Ser Gly Arg Lys Ala Ala Ile Glu Leu Lys Gly Cys
            100                 105                 110

Leu Asp Gly Asn Asn Thr Asn Ile Phe Asp Arg Pro Gln Ala Glu
        115                 120                 125

Glu Phe Val Ile Trp Ser Val Cys Thr Asn Pro Gly Ala Asp Pro Gln
130                 135                 140
```

His Asn Val Trp Ser Gly Leu His Thr Arg Leu Ser Ala Glu Ile Ile
145                 150                 155                 160

Ser Arg Glu Gln Arg Ile Asp Gly Met Val Ile Trp Asp Trp Ala Cys
            165                 170                 175

Gly Thr Val Gly Arg Pro Cys Pro Lys Ile Ala Thr Glu Pro Glu Arg
            180                 185                 190

Ala Val Thr Phe Gly Pro Phe Lys Leu Pro Pro Cys Leu Tyr Leu
            195                 200                 205

Leu Pro Ser Thr Ile Pro Ser Pro Arg Asn Asn Pro Ser Pro Arg Ala
210                 215                 220

Gln Gln Ile Glu Asp Val Gln Leu Ile Lys Ala Phe His Asp Cys Phe
225                 230                 235                 240

Gly Cys Arg Ser Glu Glu Val Asn Phe Val Asn Phe Asp Val Gly Tyr
            245                 250                 255

His Gly Lys Asp Thr Val Arg Lys Thr Thr Ile Ile Arg Asn Gly Met
            260                 265                 270

Val Glu Arg Glu Ser Glu Met Thr Ala Ile Arg Arg Ser
            275                 280                 285

<210> SEQ ID NO 31
<211> LENGTH: 219
<212> TYPE: PRT
<213> ORGANISM: Nocardia rubra

<400> SEQUENCE: 31

Met Gly Phe Leu Glu Asp Trp Asp Leu Ser Tyr Asp Glu Ile Asn Glu
1               5                   10                  15

Leu Leu Thr Asp Asn Pro Ser Leu Arg Ser Phe Val Met Gly Tyr Ala
            20                  25                  30

Ala Glu Ile Lys Cys Arg Asn Met Phe Phe Val Asp His Pro His Ile
            35                  40                  45

Thr Asn Ile Tyr Lys Pro Asp Asp His Asp Arg Thr Glu Lys Gly Asp
        50                  55                  60

Trp Ile Ile Asn Tyr Lys Gly His Arg Ile Gly Val Glu Val Lys Ser
65                  70                  75                  80

Leu Gln Thr Asn Ser Leu Arg Leu Arg Arg Asp Gly Ser Val Arg Pro
                85                  90                  95

Asn Tyr Gln Cys Asp Ala Ser Asp Ala Arg Thr Val Ile Phe Ala Asp
            100                 105                 110

Gly Ser Glu Val His Thr Thr Ala Leu Leu Val Gly Phe Asp Val
            115                 120                 125

Val Ala Val Asn Ile His Ala Phe Glu Asn Lys Trp Asp Phe Ala Phe
130                 135                 140

Ala Lys Asn Glu Asp Leu Ile Thr Met Glu Gly Ala Thr Arg Gly Ala
145                 150                 155                 160

Ala Lys Asp Tyr Thr Glu Leu Gln Lys Arg Asn Leu Ile Lys Thr Leu
            165                 170                 175

Gln Pro Met Pro Met Asp Val Pro Ala Pro Tyr Thr Arg Asp Pro Phe
            180                 185                 190

Lys Leu Phe Asp Glu Ile Ile Glu Arg Met Lys Gly Glu Gln Pro
            195                 200                 205

Gln Leu Lys Ala Lys Ile Ile Glu Asp Glu Glu
210                 215

```
<210> SEQ ID NO 32
<211> LENGTH: 244
<212> TYPE: PRT
<213> ORGANISM: Nostoc species

<400> SEQUENCE: 32

Met Ser Lys Glu Gln Asn Leu Val Gln Thr Ile Gln Ser Gln Phe Arg
1               5                   10                  15

Gln Asp Ser Thr Gln Leu Gln Val Phe Lys Leu Leu Ser Asp Gln Gln
            20                  25                  30

Trp His Cys Arg Glu Cys Glu Gly Lys Lys Ile Gly Ser Asn Gln Tyr
        35                  40                  45

Ala Gly Gly Gly Ile Gln Gly Leu Gln Arg Gly Thr Arg Ser Arg
50                  55                  60

Pro Gly Leu Val Ile Glu Thr Thr Lys Asn Tyr Cys Gln Thr Cys Gln
65                  70                  75                  80

Gln Thr Arg Leu Gly Asp Arg Trp Thr Gly Glu Ile Lys Ser Ala Asn
                85                  90                  95

Ser Ala Ser Asn Ile Pro Ala Ser Leu Val Glu Lys Ile Leu Gln Val
            100                 105                 110

Tyr Ser Tyr Thr Asp Val Ile Glu Gln Arg Gln Arg Glu Lys His Glu
        115                 120                 125

Leu Val Ile Asp His Arg Phe Pro Met Glu Arg Trp Gly Ala Ser Glu
130                 135                 140

Pro Pro His Leu Thr Ser Met Asn Asp Asn Glu Ile Lys Arg Lys Phe
145                 150                 155                 160

Gln Leu Leu Lys Lys Asp Thr Ser Gly Asn His Asn Leu Leu Lys Ser
                165                 170                 175

Arg Ser Cys Glu Arg Cys Ile Lys Thr Gly Lys Arg Gly Ala Pro Phe
            180                 185                 190

Gly Ile His Phe Trp Tyr Gln Gly Asp Glu Asn Trp Pro Ser Val His
        195                 200                 205

Gln Arg Gly Asp Glu Ala Glu Gly Cys Val Gly Cys Gly Trp Tyr
210                 215                 220

Asn Phe Glu Ala Trp Arg Asn Ala Leu Asn Gln Lys Leu Ser Gln Ser
225                 230                 235                 240

Asp Gln His Lys

<210> SEQ ID NO 33
<211> LENGTH: 293
<212> TYPE: PRT
<213> ORGANISM: Bacillus stearothermophilus

<400> SEQUENCE: 33

Met Met Thr Glu Leu Lys Asn Ser Asn Cys Ile Glu Glu Tyr Gln Glu
1               5                   10                  15

Asn Gly Lys Thr Lys Val Arg Ile Lys Pro Phe Asn Ala Leu Ile Glu
            20                  25                  30

Leu Tyr Asp Asn Gln Ile Pro Thr Gly Asn Ile Lys Glu Asn Leu Asp
        35                  40                  45

Lys Leu Gln Asn Tyr Val Met Lys Val Ala Asp Ala Lys Gly Leu Thr
50                  55                  60

Lys Pro Ala Ser Ala Ala Phe Ser Asn Thr Arg Gly Thr Trp Phe Glu
65                  70                  75                  80

Val Met Ile Ala Ile Gln Ser Trp Asn Tyr Arg Ile Lys Arg Gly Tyr
                85                  90                  95
```

```
Asn Asp Tyr Leu Ile Ile Lys Met Pro Asn Val Lys Thr Phe Asp Phe
            100                 105                 110

Arg Lys Ile Phe Asp Asp Glu Thr Arg Glu Lys Leu Tyr Gln Leu Glu
            115                 120                 125

Lys Ser Leu Leu Thr His Lys Gln Gln Val Arg Leu Ile Thr Ser Asn
        130                 135                 140

Pro Asp Leu Leu Ile Ile Arg Gln Lys Asp Leu Ile Lys Asp Glu Tyr
145                 150                 155                 160

Asn Gln Pro Ile Asp Lys Phe Thr His Glu Asn Val Asp Thr Ala Leu
                165                 170                 175

Thr Leu Phe Lys His Leu Glu Arg Lys Cys Lys Trp Asp Ser Leu Val
            180                 185                 190

Ala Gly Ile Gly Leu Lys Thr Ser Leu Arg Pro Asp Arg Arg Leu Gln
            195                 200                 205

Leu Val His Glu Gly Asn Ile Leu Lys Ser Leu Phe Ala His Leu Lys
        210                 215                 220

Met Arg Tyr Trp Asn Pro Lys Ala Glu Phe Lys Tyr Tyr Gly Ala Ser
225                 230                 235                 240

Ser Glu Pro Val Ser Gln Ala Asp Asp Ala Leu Gln Thr Ala Ala
                245                 250                 255

Thr His Thr Ile Val Asn Val Asn Ser Thr Pro Glu Arg Ala Val Asp
            260                 265                 270

Asp Val Phe Ser Leu Thr Ser Phe Glu Asp Ile Asp Lys Met Leu Asp
            275                 280                 285

Gln Ile Ile Lys Lys
        290

<210> SEQ ID NO 34
<211> LENGTH: 300
<212> TYPE: PRT
<213> ORGANISM: Bacillus species

<400> SEQUENCE: 34

Met Ile Glu Thr Val Leu Glu Lys Val Thr Asn Lys Asn Asn Phe Val
1               5                   10                  15

Thr Leu Gln Asn Tyr Thr Asp Phe Ala Leu Tyr Phe Leu Glu Tyr Ile
            20                  25                  30

Gln Lys Asn Lys Gln Ala Thr Ile Val Ser Gln Asn Glu His Val Tyr
        35                  40                  45

Asn Phe Tyr Gln Tyr Asn Ser Glu Ala Asn Tyr Gln Val Thr Arg Pro
    50                  55                  60

Phe Asn Ser Lys Ile Leu Tyr Ser His Gln Asp Phe Leu Asp Asn Leu
65                  70                  75                  80

Gly Glu Phe Asn Lys Ile Leu Lys Asp Leu Lys Ser Asp Arg Asn His
                85                  90                  95

Ala Lys Ile Leu Asp Arg Ser Ile Ile Asn Arg Thr Ile Tyr Thr Val
            100                 105                 110

Gln Gln Thr Ile Gly Phe Ala Leu Asp Gly Leu Asp Ala Asn Arg Thr
        115                 120                 125

Asn Val Ala Arg Lys Leu Asn Gly Asp Tyr Phe Glu Gln Leu Ile Leu
    130                 135                 140

Leu Leu Leu Arg Glu Ile Gly Ala Pro Ala Asn Asn Gly Val Val Lys
145                 150                 155                 160

Val Pro Val Asn Met Glu Asp Lys Gln Leu Phe Asn Met Ser Tyr Gln
```

```
                        165                 170                 175
His Asp Leu Ile Leu Lys Asp Lys Lys Gly Glu Val Lys Leu Ile Gly
                180                 185                 190

Ser Val Lys Thr Thr Ser Lys Asp Arg Ile Gly Lys Ile Phe Val Asp
            195                 200                 205

Lys Phe Leu Tyr Ser Lys Leu Thr Glu Thr Thr Val Pro His Ile Ala
        210                 215                 220

Ile Phe Leu His Asp Val Gln Arg Lys Arg Asn Lys Asp Pro Gln Lys
225                 230                 235                 240

Phe Gly Ile Asn Gly Thr Phe Leu Ala Gly His Phe Lys Gly Tyr Thr
                245                 250                 255

Val Lys Leu Asn Pro Leu Asp Gly Val Tyr Tyr Phe Asp Pro Arg Pro
            260                 265                 270

Gln Met Gln Thr Asp Val Leu Leu Ser Glu His Ile Gln Thr Phe Asp
        275                 280                 285

His Leu Leu Cys Asp Asp Ile Trp Ser Tyr Val Asp
    290                 295                 300

<210> SEQ ID NO 35
<211> LENGTH: 213
<212> TYPE: PRT
<213> ORGANISM: Bacillus amyloliquefaciens

<400> SEQUENCE: 35

Met Glu Val Glu Lys Glu Phe Ile Thr Asp Glu Ala Lys Glu Leu Leu
1               5                   10                  15

Ser Lys Asp Lys Leu Ile Gln Gln Ala Tyr Asn Glu Val Lys Thr Ser
            20                  25                  30

Ile Cys Ser Pro Ile Trp Pro Ala Thr Ser Lys Thr Phe Thr Ile Asn
        35                  40                  45

Asn Thr Glu Lys Asn Cys Asn Gly Val Val Pro Ile Lys Glu Leu Cys
    50                  55                  60

Tyr Thr Leu Leu Glu Asp Thr Tyr Asn Trp Tyr Arg Glu Lys Pro Leu
65                  70                  75                  80

Asp Ile Leu Lys Leu Glu Lys Lys Gly Gly Pro Ile Asp Val Tyr
                85                  90                  95

Lys Glu Phe Ile Glu Asn Ser Gly Leu Lys Arg Val Gly Met Glu Phe
            100                 105                 110

Glu Thr Gly Asn Ile Ser Ser Ala His Arg Ser Met Asn Lys Leu Leu
        115                 120                 125

Leu Gly Leu Lys His Gly Glu Ile Asp Leu Ala Ile Ile Leu Met Pro
    130                 135                 140

Ile Lys Gln Leu Ala Tyr Tyr Leu Thr Asp Arg Val Thr Asn Phe Glu
145                 150                 155                 160

Glu Leu Glu Pro Tyr Phe Glu Leu Thr Glu Gly Gln Pro Phe Ile Phe
                165                 170                 175

Ile Gly Phe Asn Ala Glu Ala Tyr Asn Ser Asn Val Pro Leu Ile Pro
            180                 185                 190

Lys Gly Ser Asp Gly Met Ser Lys Arg Ser Ile Lys Lys Trp Lys Asp
        195                 200                 205

Lys Val Glu Asn Lys
    210
```

HIGH FIDELITY RESTRICTION ENDONUCLEASES

CROSS REFERENCE

This application is a continuation of U.S. patent application Ser. No. 14/137,583, filed Dec. 20, 2013, now abandoned, which is a divisional of U.S. patent application Ser. No. 13/022,561, filed Feb. 7, 2011, now U.S. Pat. No. 8,637,291, which is a continuation-in-part of U.S. patent application Ser. No. 12/172,963 filed Jul. 14, 2008, now U.S. Pat. No. 8,372,619, which claims priority from U.S. provisional application Ser. No. 60/959,203 filed Jul. 12, 2007, herein incorporated by reference. This application also claims priority from U.S. provisional applications Ser. No. 61/301,666 filed Feb. 5, 2010, and Ser. No. 61/387,800 filed Sep. 29, 2010, herein incorporated by reference.

BACKGROUND

Restriction endonucleases are enzymes that cleave double-stranded DNAs in a sequence-specific manner (Roberts, R. J. *Proc Natl Acad Sci USA* 102: 5905-5908 (2005); Roberts, et al. *Nucleic Acids Res* 31:1805-1812 (2003); Roberts, et al. *Nucleic Acids Res* 33:D230-232 (2005); Alves, et al. *Restriction Endonucleases*, "Protein Engineering of Restriction Enzymes," ed. Pingoud, Springer-Verlag Berlin Heidelberg, New York, 393-407 (2004)). They are ubiquitously present among prokaryotic organisms (Raleigh, et al., *Bacterial Genomes Physical Structure and Analysis*, Ch. 8, eds. De Bruijn, et al., Chapman & Hall, New York, 78-92 (1998)) in which they form part of restriction-modification systems, which mainly consist of an endonuclease and a methyltransferase. The cognate methyltransferase methylates the same specific sequence that its paired endonuclease recognizes and renders the modified DNA resistant to cleavage by the endonuclease so that the host DNA can be properly protected. However, when there is an invasion of foreign DNA, in particular bacteriophage DNA, the foreign DNA will be degraded before it can be completely methylated. The major biological function of the restriction modification system is to protect the host from bacteriophage infection (Arber *Science* 205:361-365 (1979)). Other functions have also been suggested, such as involvement in recombination and transposition (Carlson, et al. *Mol Microbiol*, 27:671-676 (1998); Heitman, *Genet Eng (NY)* 15:57-108 (1993); McKane, et al. *Genetics* 139:35-43 (1995)).

The specificity of the approximately 3,000 known restriction endonucleases for their greater than 250 different target sequences could be considered their most interesting characteristic. After the discovery of the sequence-specific nature of the first restriction endonuclease (Danna, et al., *Proc Natl Acad Sci USA* 68:2913-2917 (1971); Kelly, et al., *J Mol Biol* 51:393-409 (1970)), it did not take long for scientists to find that certain restriction endonucleases cleave sequences which are similar but not identical to their defined recognition sequences under non-optimal conditions (Polisky, et al., *Proc Natl Acad Sci USA*, 72:3310-3314 (1975); Nasri, et al., *Nucleic Acids Res* 14:811-821 (1986)). This relaxed specificity is referred to as star activity of the restriction endonuclease.

Star activity is a problem in molecular biology reactions. Star activity introduces undesirable cuts in a cloning vector or other DNA. In cases such as forensic applications, where a certain DNA substrate needs to be cleaved by a restriction endonuclease to generate a unique fingerprint, star activity will alter a cleavage pattern profile, thereby complicating analysis. Avoiding star activity is also critical in applications such as strand-displacement amplification (Walker, et al., *Proc Natl Acad Sci USA*, 89:392-396 (1992)) and serial analysis of gene expression (Velculescu, et al., *Science* 270:484-487 (1995)).

SUMMARY

In an embodiment of the invention, a method is provided of identifying a fidelity index (FI) of a restriction endonuclease and variants thereof that includes selecting a reaction buffer and a DNA containing the binding and cleavage site of the restriction endonuclease; permitting the serially diluted restriction endonuclease or variants thereof to cleave the DNA substrate; and determining an FI for each of the restriction endonucleases and the one or more variants thereof.

In an embodiment, the method further comprises comparing the FI for the restriction endonuclease and the variants thereof to obtain an improvement factor of, for example, greater than 2 for the variant.

In an embodiment of the invention, a buffer is selected that includes potassium acetate, Tris acetate and magnesium acetate; or magnesium chloride.

Additional embodiments include:

(a) A composition, comprising: an enzyme comprising SEQ ID No. 1 in which one or more amino acids have been mutated, wherein the position of one or more mutations is selected from the group consisting of S36, K77, P154, E163, Y165 and K185.

(b) A composition, comprising: an enzyme comprising SEQ ID No. 2 in which one or more amino acids have been mutated, wherein the position of one or more mutations is selected from the group consisting of K198 and Q148.

(c) A composition, comprising: an enzyme comprising SEQ ID No. 3 in which one or more amino acids have been mutated, wherein the position of one or more mutations is selected from the group consisting of S15, H20, E34, M58, Q95, R106, K108, T181, R187 and R199.

(d) A composition, comprising: an enzyme comprising SEQ ID No. 4 in which one or more amino acids have been mutated, wherein the position of one or more mutations is selected from D16, D148 and E132.

(e) A composition, comprising: an enzyme comprising SEQ ID No. 5 in which one or more amino acids have been mutated, wherein the position of one or more mutations is selected from the group consisting of K75, N146 and D256.

(f) A composition, comprising: an enzyme comprising SEQ ID No. 6 in which one or more amino acids have been mutated, wherein the position of one or more mutations is selected from the group consisting of E198 and D200.

(g) A composition, comprising: an enzyme comprising SEQ ID No. 7 in which one or more amino acids have been mutated, wherein the position of one or more mutations is selected from the group consisting of K229, E025, R034 and Q261.

(h) A composition, comprising: an enzyme comprising SEQ ID No. 8 in which the position of the mutation is K225.

(i) A composition, comprising: an enzyme comprising SEQ ID No. 9 in which one or more amino acids have been mutated, wherein the position of one or more mutations is selected from the group consisting of H137, D177, K363, K408, R411, Q215, Q226 and Q230.

(j) A composition, comprising: an enzyme comprising SEQ ID No. 10 wherein the position of the mutation is F376.

(k) A composition, comprising: an enzyme comprising SEQ ID No. 11 in which one or more amino acids have been mutated, wherein the position of one or more mutations is selected from the group consisting of R78, T140, E152, R199 and F217.

(l) A composition, comprising: an enzyme comprising SEQ. ID No. 12 in which one or more amino acid have been mutated, wherein the position of one or more mutations is selected from the group consisting of G26, P105, T195, Q210, Y147, Y193, K114, T197, S245, D252 and Y027.

(m) A composition, comprising: an enzyme comprising SEQ ID No. 13 in which one or more amino acids have been mutated, wherein the position of one or more mutations is selected from the group consisting of H10, N208, K48, K74, R75, Y56, K58 and M117.

(n) A composition, comprising: an enzyme comprising SEQ ID No. 14 in which one or more amino acids have been mutated, wherein the position of one or more mutations is selected from the group consisting of K014, Q069, E099, R105, R117, G135 and Y035.

(o) A composition, comprising: an enzyme comprising SEQ ID No. 15 in which one or more amino acids have been mutated, wherein the position of one or more mutations are selected from the group consisting of N106, Q169, E314 and R126.

(p) A composition, comprising: an enzyme comprising SEQ ID No. 16 in which one or more amino acids have been mutated, wherein the position of one or more mutations is selected from the group consisting of T20, P52, Y67, K68, R75, E86, Q90, S91, Q93, H121 and G172.

(q) A composition, comprising: an enzyme comprising SEQ ID No. 17 in which one or more amino acids have been mutated, wherein the position of one or more mutations selected from the group consisting of E059, P065, S108, N172, K174, Q179, G182 and Y055.

(r) A composition, comprising: an enzyme comprising SEQ ID No. 18 in which one or more amino acids have been mutated, wherein the position of one or more mutations is selected from the group consisting of N212 and L213.

(s) A composition, comprising: an enzyme comprising SEQ ID No. 19 having a mutation at position N65.

(t) A composition, comprising: an enzyme comprising SEQ ID No. 20 in which one or more amino acids have been mutated, wherein the position of one or more mutations is selected from the group consisting of E007, D011, E049, R073, R114, G137, S210 and R213.

(u) A composition, comprising: an enzyme comprising SEQ ID No. 21 in which one or more amino acids have been mutated, wherein the position of one or more mutations is selected from the group consisting of P079, E086, H096 and E218.

(v) A composition, comprising: an enzyme comprising SEQ ID No. 22 in which one or more amino acids have been mutated, wherein the position of one or more mutations is selected from the group consisting of E32, S081, G132, F60 and S61.

(w) A composition, comprising: an enzyme comprising SEQ ID No. 23 in which one or more amino acids have been mutated, wherein the position of one or more mutations is selected from the group consisting of G013, G016, K018, P052, R053, K070, E071, D072, G073, S84, E086, R090, K094, R095, P099, P103, K113, N135, S151, P157, G173, T204, S206, K207, E233, N235, E237, S238, D241, K295, S301 and S302.

(x) A composition, comprising: an enzyme comprising SEQ ID No. 24 in which one or more amino acids have been mutated, wherein the position of one or more mutations is selected from the group consisting of S64, S80, S162, T77/T96 and N178.

(y) A composition, comprising: an enzyme comprising SEQ ID No. 25 in which the position R232 is mutated.

(z) A composition, comprising: an enzyme comprising SEQ ID No. 26 in which one or more amino acids have been mutated, wherein the position of one or more mutations is selected from the group consisting of S50, Y81, N93 and W207.

(aa) A composition, comprising: an enzyme comprising SEQ ID No. 27 having a mutation at G26.

(bb) A composition, comprising: an enzyme comprising SEQ ID No. 28 having a mutation at E112/R132.

(cc) A composition, comprising: an enzyme comprising SEQ ID No. 29 in which one or more amino acids have been mutated, wherein the position of one or more mutations is selected from the group consisting of N016, S33, P36, H76, P87, N89, R90, T138, K141, K143, Q221, Q224, N253, Q292, R296, T152, G326 and T324.

(dd) A composition, comprising: an enzyme comprising SEQ ID No. 30 in which one or more amino acids have been mutated, wherein the position of one or more mutations is selected from the group consisting of K024, P214, E146, N251 and Y095.

(ee) A composition, comprising: an enzyme comprising SEQ ID No. 31 in which one or more amino acids have been mutated, wherein the position of one or more mutations is selected from the group consisting of G075, Q099, G155, P022 and R90.

(ff) A composition, comprising: an enzyme comprising SEQ ID No. 32 in which one or more amino acids have been mutated, wherein the position of one or more mutations is selected from the group consisting of S097 and E125.

(gg) A composition, comprising: an enzyme comprising SEQ ID No. 33 in which one or more amino acids have been mutated, wherein the position of one or more mutations is selected from the group consisting of K021, 1031 and T120.

(hh) A composition, comprising: an enzyme comprising SEQ ID No. 34 in which one or more amino acids have been mutated, wherein the position of one or more mutations is selected from the group consisting of K7, T10, N11, N14, Q232 and T199.

(ii) A composition, comprising: an enzyme comprising SEQ ID No. 35 in which one or more amino acid have been mutated, wherein the position of one or more mutations is selected from the group consisting of P92, P144, G197 and M198.

Any of the above compositions may be further characterized in that the mutated enzyme has an FI in a predetermined buffer that is greater than the enzyme without the mutations in the predetermined buffer.

BRIEF DESCRIPTION OF THE DRAWINGS

In FIG. 1A, the asterisk (*) sign denotes the lane on the left (lane 2) in which star activity is no longer detected. The number (#) sign denotes the lane on the right (lane 8) in which partial digestion occurs. The starting concentration of the PvuI-WT was calculated to be 77 units.

In FIG. 1B, complete digestion was observed until lane 15, after which star activity was observed. The window of dilution allowing for complete digestion expanded from 6 dilutions to 15 dilutions in the series. The starting concentration of the PvuI-HF was calculated to be at least 9600 units.

In FIG. 2A, the asterisk (*) sign denotes the lane on the left (lane 9) in which star activity is no longer detected. The number (#) sign denotes the lane on the right (lane 15) in which partial digestion occurs. The starting concentration of the HindIII-WT was calculated to be 9,600 units.

In FIG. 2B, complete digestion was observed until lane 13, after which star activity is observed. The window of dilution allowing for complete digestion expanded from 6 dilutions to 13 dilutions in the series. The starting concentration of the HindIII-HF was calculated to be at least 2,400 units.

In FIG. 3A, the asterisk (*) sign denotes the lane on the left (lane 12) in which star activity is no longer detected. The number (#) sign denotes the lane on the right (lane 12) in which partial digestion occurs. Neither star activity nor partially digested DNA was observed. The starting concentration of the DraIII-WT was calculated to be 1,200 units.

In FIG. 3B, complete digestion was observed until lane 12, after which star activity is observed. The starting concentration of the DraIII-HF was calculated to be at least 1,200 units.

In FIG. 4A, the * sign denotes the lane on the left (lane 9) in which star activity is no longer detected. The #sign denotes the lane on the right (lane 13) in which partial digestion occurs. In FIG. 1A, the starting concentration of the KpnI-WT was calculated to be 2,000 units.

In FIG. 4B, complete digestion was observed throughout with no star activity or partial digestion. The starting concentration of the KpnI-HF was calculated to be greater than 12,000 units.

In FIG. 5A, the * sign shows the beginning of the star activity on its left (lane 6), the #sign shows the beginning of partial activity on its right (lane 12). The starting amount of Sty-WT was calculated to be 1,000 units.

In FIG. 5B, star activity was observed in the first 2 lanes and partial digestion from lane 14 or 15. The starting amount of StyI-HF was calculated to be 4,000 units.

FIG. 8 shows a comparison of BclI-HF and BclI-WT in NEB4 on lambda (dam⁻). The BclI-HF has an FI of at least 2,000, while the BclI-WT has an FI of 32, providing an improvement factor of at least 64. The right panel is the theoretical digestion pattern.

FIG. 15 shows a comparison of MluI-HF and MluI-WT on lambda DNA. The MluI-HF has an FI of at least 32,000 in NEB4, while the MluI-WT has an FI of 32, providing an improvement factor of at least 1,000. The right panel is the theoretical digestion pattern.

DETAILED DESCRIPTION OF EMBODIMENTS

Figure 1A:
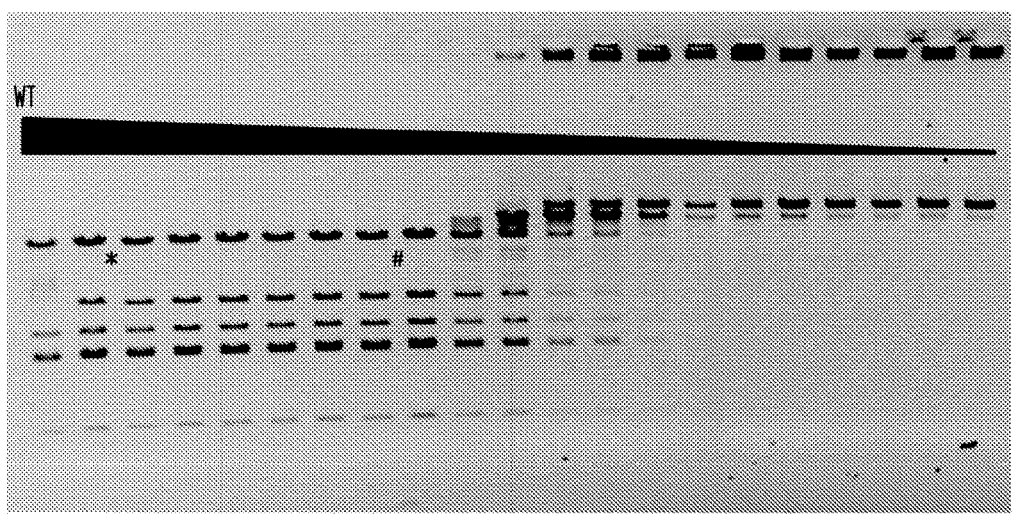
FIGS. 1A and 1B show the comparison of PvuI-HF and PvuI-WT activity.

The generation of mutants of restriction endonucleases with improved specificity for a single sequence is not straightforward. Numerous problems were encountered. These include the following: a mutated enzyme had reduced or no activity, did not have reduced star activity or actually had increased star activity. Alternatively, a mutated enzyme could not be cloned and therefore could not be analyzed.

Failure to produce a mutant resulted from any of a variety of possible causes including any of the following. It could be due to failed inverted PCR. It is also possible that the mutation which generated new specific activity was toxic to a host cell even if it expressed the cognate methylase under conditions that were normally protective for expression of the non-mutated restriction endonuclease. In these circumstances, no viable mutant clone would be obtained. Alternatively, the mutant might have a preference for a particular buffer such that when tested in another buffer, no activity would be detected. Another difficulty encountered, was that although generally a crude lyzate of each mutation was tested, in some case, the enzyme had to be purified to detect activity where activity was not detected in the lysate scoring the assay negative.

It was surprising to note that in several examples, a change of a proline to an alanine resulted in variants with a desired FI of at least greater than 250 and yielding an improvement factor of at least two fold. This was exemplified in variants of PvuI, BamHI, NruI and SpeI.

Other challenges in producing high fidelity mutants include the size of the DNA encoding some restriction endonucleases. This DNA may be difficult to amplify by PCR given the large size of the template. Moreover, the PCR products in some circumstances did not readily transform into a new host. Even if a host cell transformation was successful, transformed cells did not always produce colonies and hence could not be readily detected. In some cases, even if the colonies were obtained from transformation, they could be not cultured in any condition.

Reasons for reduction in the specific activity of mutants may result from any of the following: the mutation interferes with the folding of the protein which significantly lowered the expression level or the mutation affects the specific enzyme activity.

For example, this was observed for StyI mutants: N34A, F35A, D58A, F65A, K66A, K67A, F100A, N148A, E213A, F250A, T251A, D258A, D262A, N283A, R293A, F294A, R295A, R296A, D298A, D299A, M304A, M310A, D318A, S337A, S346A and F371A.

Loss of enzyme activity may result from causes that include any of the following: the mutation deleted the residues which are important in catalysis; or the mutations changed residues that are important in folding, thus, the misfolded mutant protein is inactive.

For example, this was observed for StyI mutants M33A, D37A, F41A, D55A, D71A, N77A, R79A, E80A, F81A, T82A, E83A, F97A, F101A, E136A, W137A, M138A, M140A, K144A, Q145A, R151A, R255A, R259A, S261A, T264A, F278A, R281A, T284A, M297A, H305A, N306A, D314A, D338A and E382A.

Generating high fidelity mutants requires painstaking work. Multiple mutants are selected and tested and only a relatively small number show high fidelity. It was not possible to predict by extrapolation which mutants are likely to show improved properties.

Examples of assays performed to identify high fidelity variants of restriction endonucleases are shown in FIGS. 1-17. The figures show the results in a single buffer for both wild type and high fidelity variants. All the figures show amounts and types of cleavage of DNA after a series of two fold dilutions from left to right on the gel with the concentration of enzyme decreasing in the direction of the triangle. Table 1 details the results for the 33 exemplified enzymes. The restriction endonuclease reaction buffers (buffers 1-4) used in the examples are defined for example in the NEB catalog (2009/10). Other buffers may be selected according to the preference of the user.

The assays yield an FI that is the ratio of the highest restriction enzyme concentration not to show apparent star activity as determined by the presence of bands associated with star activity to the restriction enzyme concentration that completely digests 1 µg of standard DNA substrate in 50 µl reaction for 1 hour at a defined temperature in a standard NEB buffers. In FIGS. 6-17, a box is placed in the figures to show star activity bands. In embodiments of the invention, the FI is for example preferably at least 250 for example greater than 500 for example greater than 1000, for example, greater than 5000.

A fidelity improvement value is calculated as a ratio of the FI of the variant divided by the FI of the non-mutant enzyme. In an embodiment of the invention, the improvement value is for example preferably at least 2, for example, at least 4, for example, at least 8, for example, at least 16.

In one embodiment, the FI refers to the ratio of the highest restriction enzyme amount not to show apparent star activity to the amount that completely digests 1 µg of standard DNA substrate in 50 µl reaction for 1 hour at specific temperature in standard NEB buffers.

TABLE 1

Summary of properties of HF enzymes

| Enzyme | Sub | FI1' | FI2' | FI3' | FI4' | Example | SEQ ID No. |
|---|---|---|---|---|---|---|---|
| PvuI-HF | pXba | ≥2000(1/8) | ≥16000(1) | ≥4000(1/4) | ≥16000(1) | 1 | 1 |
| HindIII-HF | λ | ≥260000(1/2) | ≥260000(1/2) | ≥250(1/2000) | ≥520000(1) | 2 | 2 |
| DraIII-HF | λ | ≥120(1/16) | ≥1000(1/2) | ≥32(1/64) | ≥2000(1) | 3 | 3 |
| KpnI-HF | pXba | ≥1000000(1) | ≥1000000(1) | ≥30000(1/500) | ≥1000000(1) | 4 | 4 |
| StyI-HF | λ | ≥4000(1/2) | 2000(1) | ≥16(1/250) | 4000(1/2) | 5 | 5 |
| BsaJI-HF | pBR322 | ≥1000(1/4) | ≥4000(1) | ≥4000(1) | ≥4000(1) | 6 | 6 |
| BsaWI-HF | pXba | 8(1/64) | 120(1) | ≥120(1)) | ≥4000(1) | 7 | 7 |
| BglI-HF | λ | ≥4000(1/2) | ≥8000(1) | ≥500(1/16) | ≥8000(1) | 8 | 8 |
| BsrDI-HF | pBR322 | ≥120(1/8) | ≥500(1) | ≥64(1/16) | ≥1000(1) | 9 | 9 |
| NsiI-HF | pXba | ≥250(1/32) | ≥1000(1/8) | ≥500(1/16) | ≥8000(1) | 10 | 10 |
| DpnII-HF | λ(—) | 4000(1/4) | 2000(1/4) | 64(1/128) | 8000(1) | 11 | 11 |
| BclI-HF | λ(—) | ≥250(1/32) | ≥500(1/4) | ≥32(1/64) | ≥2000(1) | 12 | 12 |
| BglII-HF | pXba | ≥8000(1/8) | ≥128000(1) | 2000(1/2) | ≥32000(1/4) | 13 | 13 |
| BstEII-HF | λ | ≥64(1/32) | ≥1000(1/2) | ≥32(1/64) | ≥2000(1) | 14 | 14 |
| BanII-HF | λ(—) | ≥4000(1) | ≥2000(1/2) | ≥500(1/8) | ≥2000(1/2) | 15 | 15 |
| PspGI-HF | pBC4 | ≥1000(1/4) | ≥4000(1) | ≥4000(1) | ≥4000(1) | 16 | 16 |
| SpeI-HF | T7 | ≥4000(1/2) | ≥250(1/8) | ≥120(1/2) | ≥1000(1) | 17 | 17 |
| BsmAI-HF | FX174 | ≥4000(1) | ≥2000(1/2) | ≥500(1/8) | ≥4000(1) | 18 | 18 |
| BstXI-HF | λ | ≥500(1/2) | ≥1000(1) | ≥500(1/2) | ≥1000(1) | 19 | 19 |
| SfiI-HF | pBC4 | 250(1/2) | ≥1000(1/8) | ≥32(1/250) | ≥8000(1) | 20 | 20 |
| PmeI-HF | pXba | ≥2000(1/8) | ≥500(1/16) | ≥32(1/250) | ≥8000(1) | 21 | 21 |
| SmaI-HF | pXba | ≥2000(1/500) | ≥32000(1/32) | ≥32(1/32000) | ≥256000(1) | 22 | 22 |

TABLE 1-continued

Summary of properties of HF enzymes

| Enzyme | Sub | FI1' | FI2' | FI3' | FI4' | Example | SEQ ID No. |
|---|---|---|---|---|---|---|---|
| AatII-HF | pXba | NC | NC | NC | ≥1000(1) | 23 | 23 |
| ApoI-HF | pXba | ≥2000(½) | ≥4000(1) | ≥1000(¼) | ≥2000(½) | 24 | 24 |
| BsmBI-HF | λ | 32(½) | 120(½) | ≥120(½) | 250(1) | 25 | 25 |
| BmtI-HF | pXba | 25600(¼) | 25600(¼) | 2000(¹⁄₅₀₀) | 1000000(1) | 26 | 26 |
| BstNI-HF | pBR322 | ≥120(½) | ≥500(1) | ≥120(¼) | 500(1) | 27 | 27 |
| MluI-HF | λ | ≥16000(½) | ≥32000(1) | ≥2000(¹⁄₁₆) | ≥32000(1) | 28 | 28 |
| BanI-HF | λ | ≥1000(½) | ≥250(⅛) | ≥250(⅛) | ≥2000(1) | 29 | 29 |
| KasI-HF | pBR322 | ≥8000(½) | ≥16000(1) | ≥2000(⅛) | ≥16000(1) | 30 | 30 |
| NruI-HF | λ | ≥64(¹⁄₂₅₀) | ≥1000(¹⁄₁₆) | ≥100(¹⁄₁₆) | ≥16000(1) | 31 | 31 |
| NspI-HF | pUC19 | ≥4000(1) | 500(1) | ≥250(⅛) | 500(1) | 32 | 32 |
| BsrFI-HF | pBR322 | ≥500(1) | ≥64(⅛) | >100 | ≥500(1) | 33 | 33 |

Diluent (Dil) A, B and C and Buffers 1-4 are defined in the NEB catalog 2009/10 page 87.

EXAMPLES

Example 1: Engineering of High Fidelity (HF) PvuI

1. Expression of PvuI

PvuI was expressed in *E. coli* transformed with pUC19-PvuIR and pACYC184-PvuIM, each containing PvuI endonuclease and methylase genes. The cells were grown at 30° C. overnight in LB with Amp and Cam.

2. Mutagenesis of PvuI-HF

All residues Cys, Asp, Glu, Gly, His, Lys, Asn, Pro, Gln, Arg, Ser, Thr were changed to Ala at positions 7, 8, 11, 12, 16, 17, 20, 21, 22, 23, 26, 28, 29, 30, 31, 34, 35, 36, 38, 40, 42, 44, 45, 46, 48, 49, 53, 55, 57, 59, 61, 63, 65, 66, 67, 69, 70, 71, 72, 73, 77, 78, 80, 81, 82, 87, 88, 90, 92, 93, 96, 97, 101, 102, 104, 106, 107, 108, 109, 110, 111, 115, 116, 119, 120, 121, 122, 126, 127, 129, 131, 132, 135, 138, 139, 144, 146, 147, 148, 150, 151, 152, 154, 155, 157, 158, 160, 161, 162, 163, 167, 169, 170, 172, 173, 174, 178, 180, 182, 183, 184, 185, 186, 187, 189, 192, 194, 195, 196, 201, 202, 203, 205, 206, 210, 211, 214, 215, 218, 219, 220, 221, 226, 230, 231, 232, 233, 235, 236, 238, 239, 240, 241, 246, 247, 248, 249, 251, 253, 254; while Tyr was changed to Phe at positions 18, 52, 56, 84, 91, 130, 143, 165, 204, 242.

The mutagenesis methods were inverse PCR with paired primers followed by DpnI-digestion. The treated product was then transformed into *E. coli* strain ER2683.

3. Selection of PvuI-HF

Selection of PvuI-HF was achieved using comparison of activity in NEB3 and NEB4 (New England Biolabs, Inc., Ipswich, Mass. (NEB) using pXba DNA as substrate. PvuI-WT has more activity in NEB3. The one with more activity in NEB4 was selected. 6 mutants were found to have more activity in NEB4: S36A, K77A, P154A, E163A, Y165F and K185A. P154A had much higher activity than WT in NEB4. Normally, the one with highest activity in NEB4 was the one with improved star activity. PvuI(P154A) was designated as PvuI-HF. This is the first time that an effective mutation was a Proline to Alanine mutation.

4. Purification of PvuI-HF

Two liters of cell ER2683(pUC19-PvuI(P154A), pACYC184-PvuIM)) were grown in LB with 100 μg/ml Amp and 33 μg/ml at 30° C. for overnight. The cells were harvested and sonicated in 20 ml 10 mM Tris-HCl, pH7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany) and stored in glycerol at −20° C.

5. Comparison of PvuI-HF and PvuI-WT

Figure 1B:
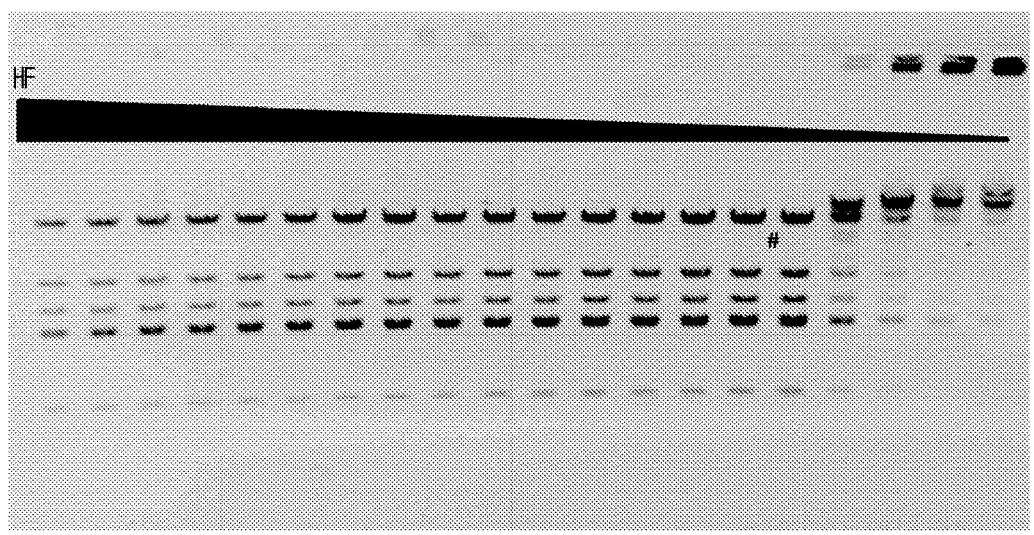

The FIs of PvuI-HF and PvuI-WT have been determined separately on pXba DNA in four NEB buffers with diluent B. The comparison is shown in FIG. 1, and the result is listed in Table 2 (below).

TABLE 2

Comparison of PvuI-HF and PvuI-WT

| | PvuI-HF | | PvuI-WT | | Improvement |
|---|---|---|---|---|---|
| Buffer | Activity | FI | Activity | FI | Factor |
| NEB1 | 12.5% | ≥2000 | 6.3% | 32 | ≥64 |
| NEB2 | 100% | ≥16000 | 25% | 32 | ≥500 |
| NEB3 | 25% | ≥4000 | 100% | 32 | ≥125 |
| NEB4 | 100% | ≥16000 | 12.5% | 32 | ≥500 |

PvuI-HF performed best in NEB2 and NEB4, in which the FI was ≥16,000; WT PvuI performed best in NEB3, in which the FI was 32. So the overall improvement factor was ≥16,000/32=≥500.

Example 2: Engineering of HF HindIII

Figure 2A:
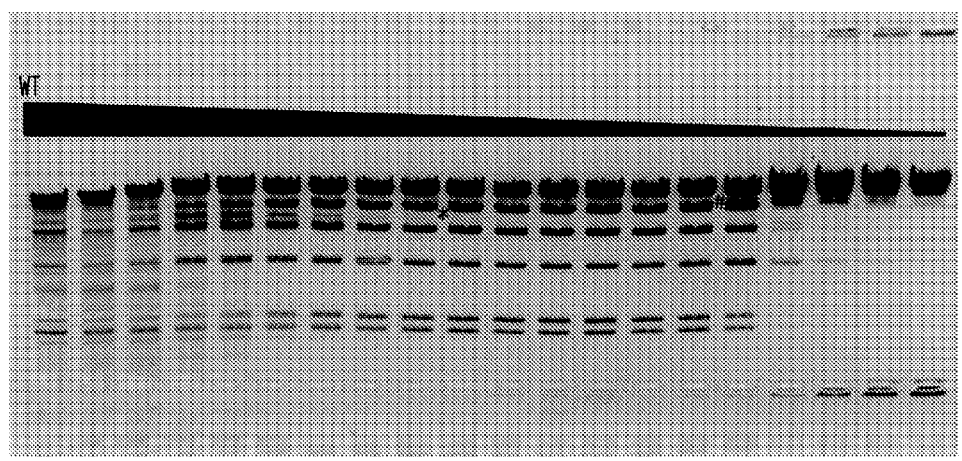
FIGS. 2A and 2B show the comparison of HindIII-HF and HindIII-WT activity.
Figure 2B:
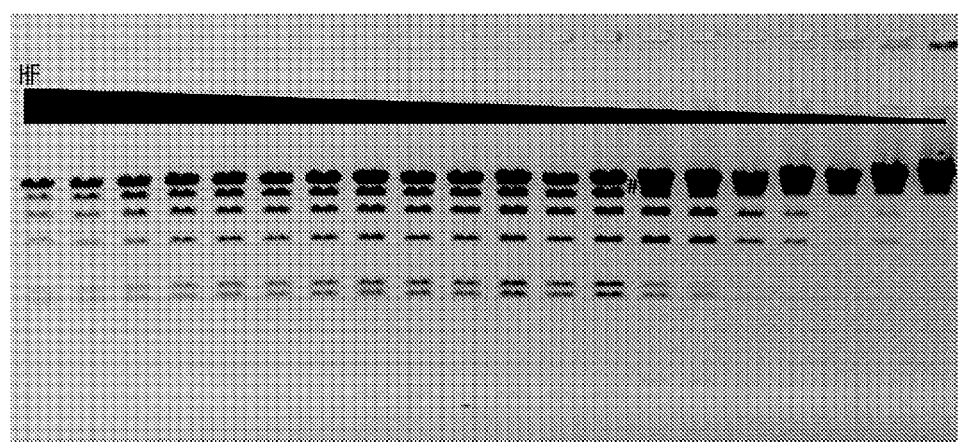

HindIII recognizes and digests at A/AGCTT as described in Example 21 of International Publication No. WO 2009/009797. A mutant HindIII(K198A) was selected as the HF version of the HindIII. Further characterization of this mutant revealed that though the performance of HindIII (K198A) on one hour scale was excellent, it did not perform well in the overnight digestion. While searching for more mutants, HindIII(Q148A) was also found to be partially good. A further step toward greater improvement was to change the Alanine to all other amino acid residues. Among those, HindIII(Q148I) was found to be excellent in both one hour and overnight reaction, and designated to be HindIII-HF (FIG. 2).

The HindIII-HF was expressed in ER3081 (pUC19-HindIIIR(Q148I)M). The growth and purification methods were performed according to WO/2009/009797.

The following table (Table 3) compares the FIs of HindIII-HF and HindIII-WT.

TABLE 3

Comparison of HindIII-HF and HindIII-WT

| Buffer | HindIII-HF | | HindIII-WT | | Improvement Factor |
|---|---|---|---|---|---|
| | Activity | FI | Activity | FI | |
| NEB1 | 50% | ≥260000 | 25% | 32 | ≥8000 |
| NEB2 | 50% | ≥260000 | 100% | 250 | ≥1000 |
| NEB3 | 0.05% | ≥250 | 25% | 4000 | ≥1/32 |
| NEB4 | 100% | ≥520000 | 50% | 32 | ≥16000 |

The HindIII-HF had the best activity in NEB4; the FI of HindIII-HF in NEB4 was ≥520000; the WT HindIII had the best activity in NEB2. The FI of HindIII-WT in NEB2 was 250. So the overall improvement factor was ≥2,000.

Example 3: Engineering of HF DraIII

1. Expression of DraIII

DraIII recognizes and digests at CACNNN/GTG. DraIII was expressed in *E. coli* ER3081 with pAGR3-DraIIIR ( ) and pACYC-DraIIIM ( ). The cells were grown at 37° C. overnight in LB with Amp and Cam.

2. Mutagenesis of DraIII

The length of DraIII protein is 227 amino acids. Total 132 amino acid sites of DraIII protein were initially designed to be mutated into Ala (or Phe). Cys, Asp, Glu, Phe, His, Lys, Met, Asn, Gln, Arg, Ser, Thr, Gly and Trp were mutated to Ala. Try was mutated to Phe. These were: 7, 9, 10, 11, 12, 14, 15, 16, 17, 18, 20, 21, 22, 23, 28, 29, 31, 32, 34, 35, 37, 40, 42, 43, 44, 45, 47, 51, 54, 55, 57, 58, 59, 60, 64, 65, 66, 67, 68, 72, 73, 74, 76, 77, 82, 83, 84, 88, 89, 90, 91, 93, 94, 95, 96, 99, 101, 102, 104, 106, 107, 108, 111, 112, 113, 114, 115, 117, 120, 121, 123, 124, 127, 128, 130, 136, 137, 138, 139, 140, 141, 142, 144, 145, 146, 147, 150, 154, 155, 156, 157, 158, 160, 161, 165, 167, 169, 170, 171, 172, 173, 175, 176, 180, 181, 183, 184, 185, 187, 189, 190, 192, 193, 196, 198, 199, 200, 201, 202, 205, 207, 208, 209, 211, 212, 213, 214, 216, 217, 218, 219, 22, and 223.

The point mutagenesis of the selected mutations was done by inverse PCR. The PCR reaction in a reaction volume of 100 μl, contained 2 μl of each PCR primer, 1 μl pAGR3-DraIIIR, 400 μM dNTP, 4 units of Deep Vent™ DNA polymerase (NEB), and 10 ul 10× Thermopol buffer with additional water.

The PCR reaction conditions were 94° C. for 5 min, followed by 25 cycles of 94° C. 30 sec, 55° C. 60 sec, 72° C. 4 min and a final extension time at 72° C. for 7 mins. The PCR product was digested by 20 units of DpnI for 1 hour. The digested product was transformed into *E. coli* ER3081 (pACYC-DraIIIM).

3. Selection of DraIII-HF

Four colonies of each mutation were grown up in LB with Amp and Cam at 37° C. overnight. The standard cognate and star activity assays of DraIII were performed using pXba as substrate in NEB4 buffer and 10% glycerol.

The mutants S15A, H20A, E34A, M58A, Q95A, R106A, K108A, T181A, R187A, R199A, N202D, T181G, T181N, T181Q, T181C, T181V, T181L, T181I, T181M, D55A, D55S, D55C, D55G, D55N, T12A, H20A, E34A, H45A, T57A, M58A, T60A, S66A, R76A, F90A, M94A, T101A, C115A, F169A, N172A, R173A, H189A, N193A and Q95A/K104A were picked out in screening assays. After several rounds of comparison in different conditions and substrates, DraIII(T181A) was found to be a preferred mutant, retaining high cleavage high activity, but displaying substantially reduced star activity. DraIII (T181A) was labeled DraIII-HF.

4. Comparison of DraIII-HF and DraIII-WT

Figure 3A:
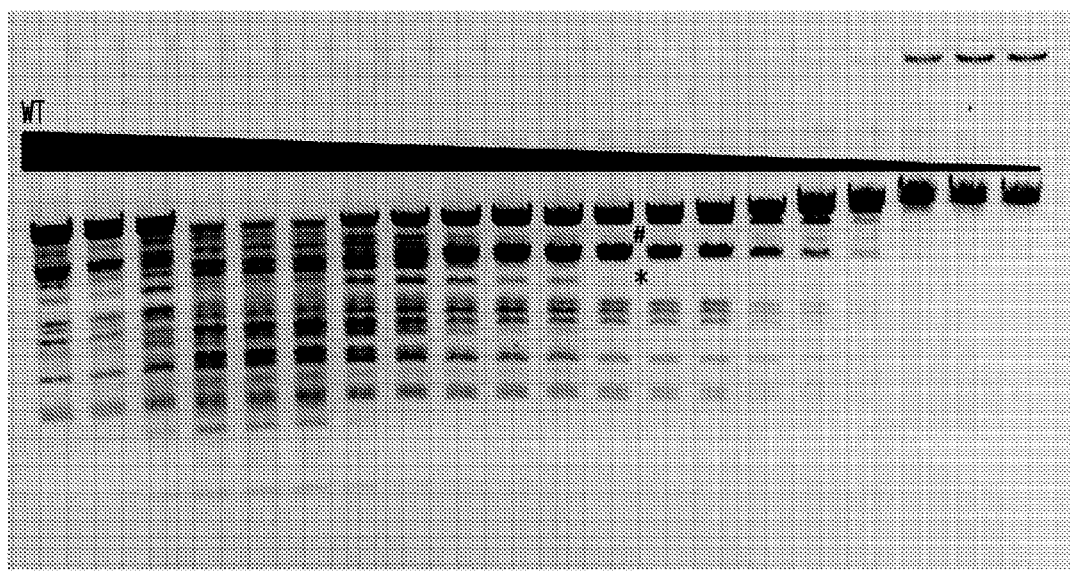
FIGS. 3A and 3B show the comparison of DraIII-HF and DraIII-WT activity.
Figure 3B:
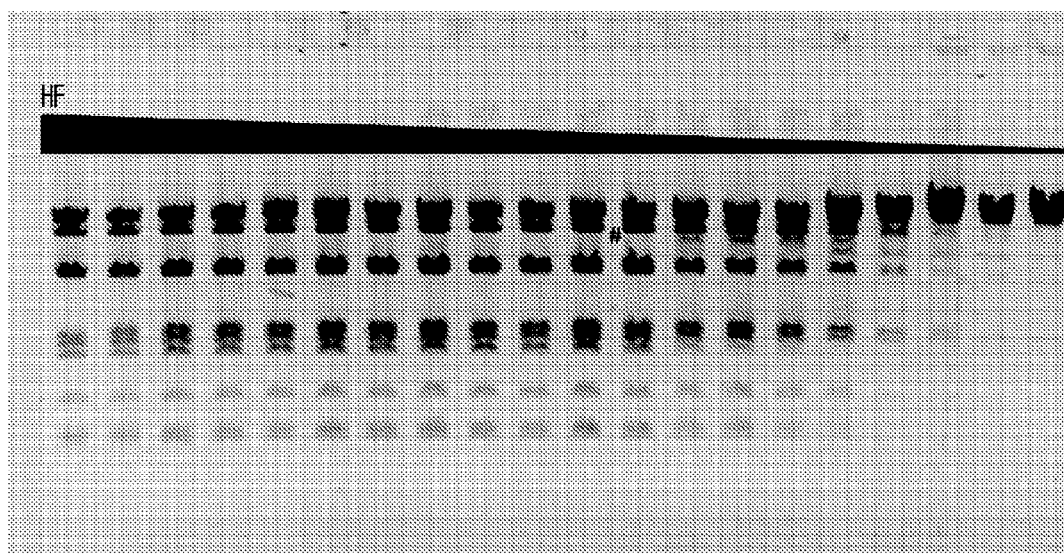
Figure 4A:
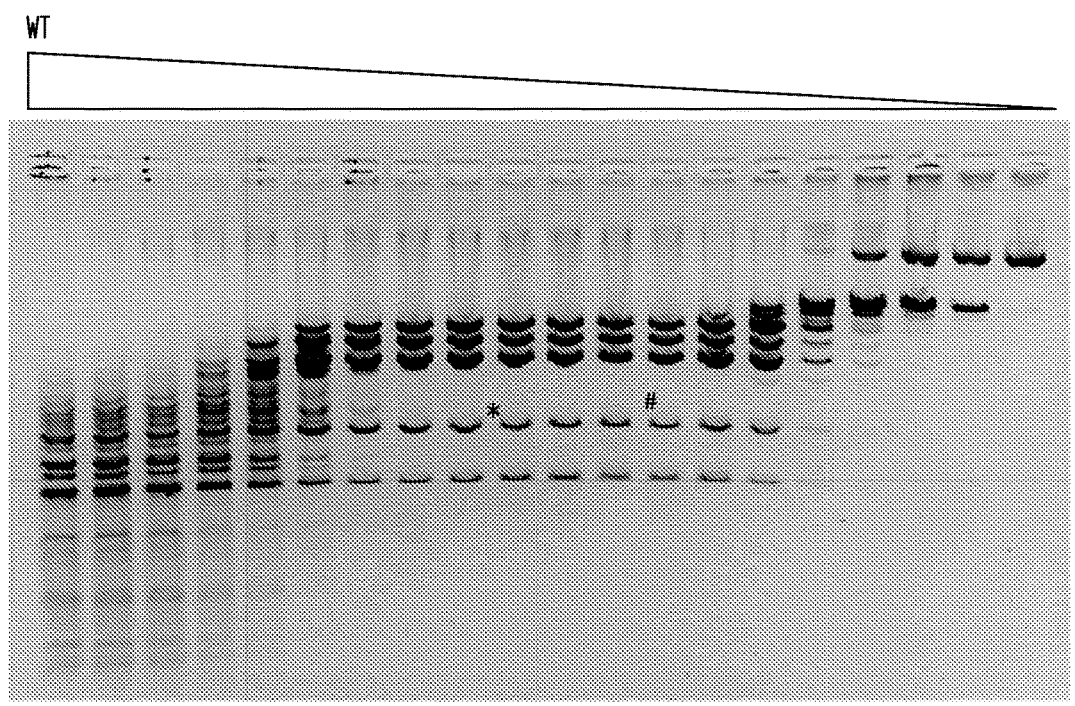
FIGS. 4A and 4B show the comparison of KpnI-HF and KpnI-WT activity.
Figure 4B:
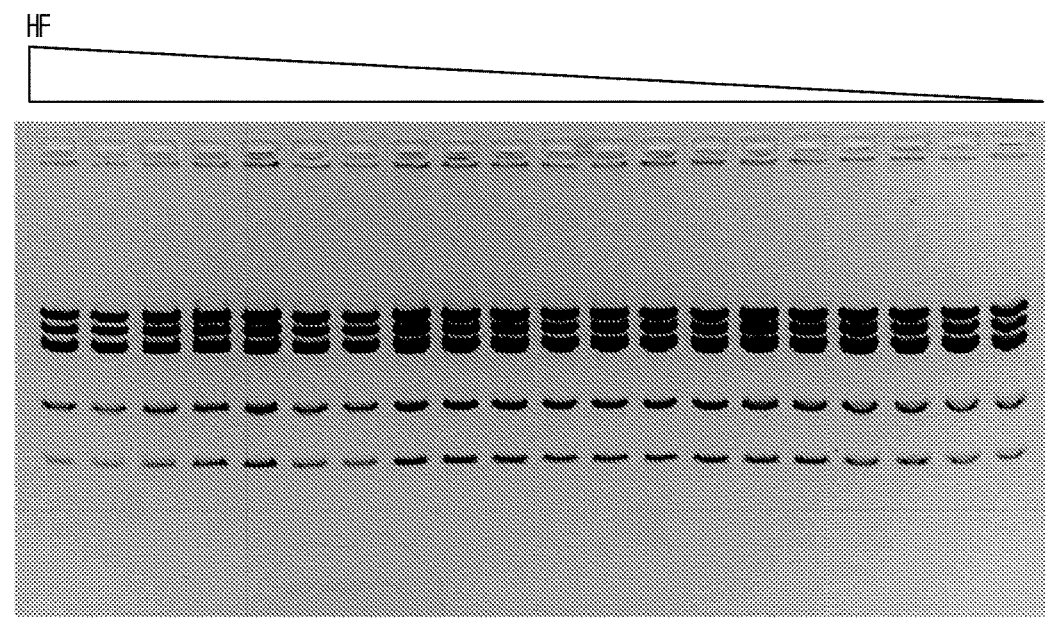

The DraIII-WT and DraIII-HF (T181A) proteins were purified using Heparin and Source 15S Column. The assay condition for detailed comparison was as follows: NEB4 (or NEB1, 2, 3), 37° C., 1 h; 2 μl purified protein in 20 μl reaction system; lambda DNA as substrate. The comparison is shown in FIGS. 3A and 3B, and the result is listed in Table 4.

TABLE 4

Comparison of DraIII-HF and DraIII-WT

| Substrate | DraIII-HF (T181A) | | DraIII-WT | | Improvement factor |
|---|---|---|---|---|---|
| | Activity | FI | Activity | FI | |
| Buffer1 | 6.25% | ≥120 | 16% | 16 | ≥8 |
| Buffer2 | 50% | ≥1000 | 100% | 2 | ≥500 |
| Buffer3 | 1.56% | ≥32 | 50% | 2 | ≥16 |
| Buffer4 | 100% | ≥64000 | 50% | 0.5 | ≥128000 |

DraIII-HF has most activity in NEB4, in which the FI was at least 64,000; the DraIII-WT has most activity in NEB2, in which the FI is 2. The overall FI improvement factor was at least 32,000 fold.

Example 4

Engineering of HF KpnI

KpnI recognizes and digests at GGTAC/C as described in Example 26 of International Publication No. WO 2009/009797. A triple mutant KpnI(D16N/E132A/D148E) was selected as the high fidelity version of the KpnI. While D148E and E132A were introduced by site-directed mutagenesis, the D16N was introduced by PCR. Further characterization of the mutations in this triple mutant revealed that the removal of the E132A will further improve the restriction enzyme, especially in the aspect of the enzyme specific activity. The triple mutant KpnI(D16N/E132A/D148E) has a specific activity of 200,000 units/mg protein, while KpnI (D16N/D148E) has a specific activity of 1,800,000 units/mg protein. The double mutant is 9 times more active than the previous triple mutant, so the double mutant KpnI(D16N/D148E) was designated as the KpnI-HF.

The KpnI-HF was expressed in ER2523(pAGR3-KpnI (D16N/D148E), pSYX20-KpnIM). The growth and purification methods were performed according to WO/2009/009797.

The following table (Table 5) compares the FIs of KpnI-HF and KpnI WT.

TABLE 5

Comparison of KpnI-HF and KpnI-WT

| Buffer | KpnI-HF | | KpnI-WT | | Improvement factor |
|---|---|---|---|---|---|
| | Relative Activity | FI | Relative Activity | FI | |
| NEB1 | 100% | ≥1,000,000 | 100% | 16 | 62,500 |
| NEB2 | 100% | ≥1,000,000 | 25% | 16 | 62,500 |
| NEB3 | 0.2% | ≥30,000 | 6% | 8 | 3,750 |
| NEB4 | 100% | ≥1,000,000 | 50% | 4 | 250,000 |

The KpnI WT had the best activity in NEB1, the FI of KpnI-WT in NEB1 was 16; the KpnI-HF had the best activity in NEB1, NEB2 and NEB4. The FI of KpnI-HF in these three buffers were all highest at ≥1,000,000. The overall improvement factor was ≥62,500.

Example 5: Engineering of HF StyI

1. Expression of StyI

StyI recognizes and digests at C/CWWGG. StyI was expressed in *E. coli* (ER2833) with pACYC-StyIM and placzz1-StyIR. The cells were grown at 37° C. overnight in LB with Amp and Cam.

2. Mutagenesis of StyI

The point mutagenesis of the selected mutations was done by inverse PCR. 237 amino acid mutations were made in StyI as follows: Cys, Asp, Glu, Phe, His, Lys, Met, Asn, Gln, Arg, Ser, Thr, Trp were mutated to Ala. Tyr was mutated to Phe. These were at the positions: 7, 9, 10, 11, 12, 14, 16, 22, 23, 24, 25, 26, 28, 30, 31, 32, 33, 34, 35, 36, 37, 38, 39, 40, 42, 43, 49, 51, 52, 53, 54, 57, 58, 59, 61, 62, 64, 65, 66, 69, 70, 73, 75, 76, 78, 79, 80, 81, 82, 85, 91, 92, 93, 95, 96, 97, 98, 99, 100, 102, 103, 104, 105, 106, 109, 111, 112, 114, 116, 118, 119, 122, 123, 124, 125, 126, 128, 129, 130, 131, 135, 136, 137, 139, 140, 141, 142, 143, 144, 145, 146, 147, 150, 151, 152, 153, 155, 157, 158, 159, 163, 164, 165, 166, 167, 170, 172, 173, 175, 176, 177, 178, 181, 183, 187, 188, 192, 193, 194, 195, 196, 200, 203, 204, 205, 207, 209, 211, 212, 213, 214, 216, 218, 219, 220, 221, 222, 227, 229, 230, 232, 234, 235, 236, 237, 238, 239, 241, 242, 245, 247, 248, 249, 250, 252, 253, 254, 256, 257, 258, 259, 260, 261, 263, 266, 267, 269, 272, 274, 277, 280, 282, 283, 284, 286, 288, 289, 291, 292, 293, 294, 295, 296, 297, 298, 303, 304, 305, 307, 308, 309, 313, 317, 318, 319, 320, 323, 324, 326, 327, 329, 331, 335, 336, 337, 339, 340, 343, 345, 346, 347, 349, 350, 351, 353, 355, 356, 359, 360, 361, 363, 365, 366, 368, 369, 370, 372, 373, 376, 377, 379, 381, and 382.

The method of primer design and PCR can be performed as described in published PCT application WO 2009/0029376 (Example 1). The PCR product was digested with DpnI and transformed into competent ER2833 (pACYC-StyIM).

3. Selection of StyI-HF

Four colonies of each mutation were grown up in LB with Amp and Cam at 37° C. overnight. The cognate activity assay and star activity assays of StyI were performed using lambda in NEB4 and ExoI buffer and 20% glycerol respectively.

The mutants K75A, N146A and D256A were picked out in screening assays. After several rounds of comparison in different conditions and substrates, K75A was found to be the preferred mutant, retaining high cleavage high activity, but displaying substantially reduced star activity. StyI (K75A) was labeled StyI-HF.

4. Comparison of StyI-HF and StyI-WT

Figure 5A:
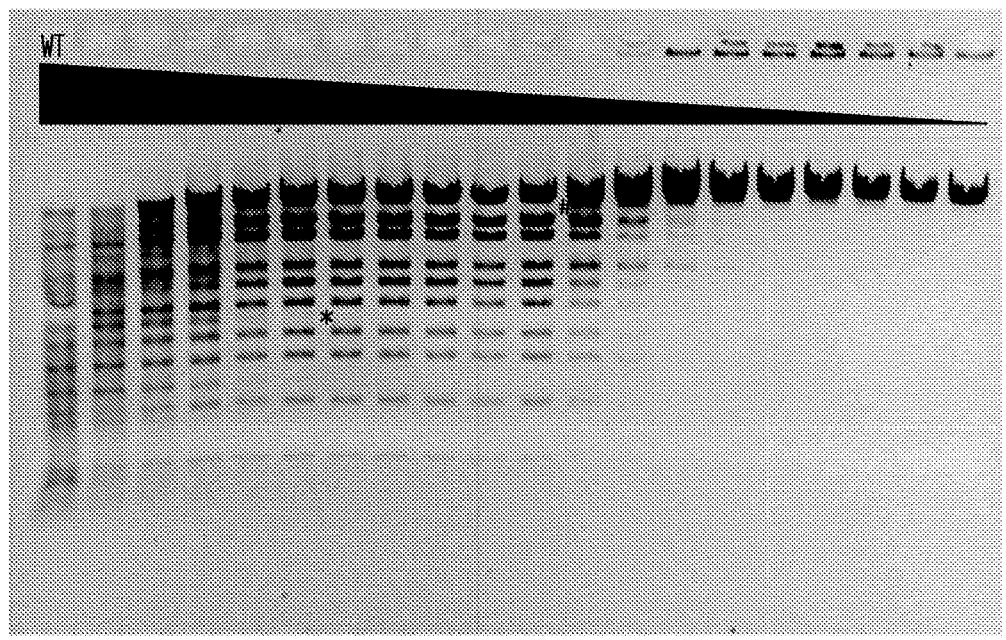
FIGS. 5A-5B shows the comparison of StyI-HF and StyI-WT.
Figure 5B:
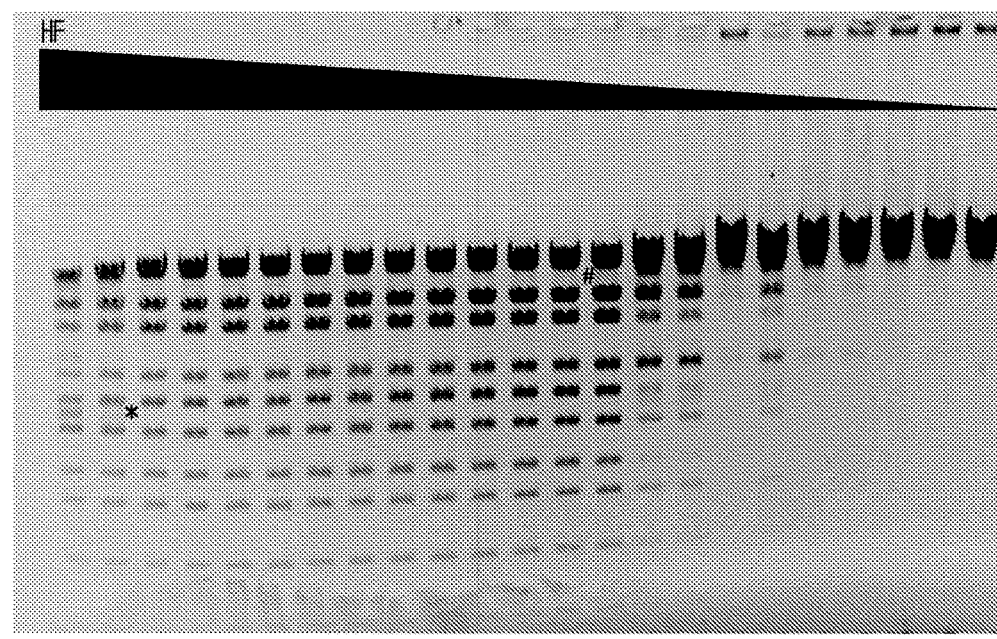

The comparison of StyI-HF and StyI-WT in NEB4 is shown in FIGS. 5A and 5B, and the result is listed in Table 6.

TABLE 6

Comparison of StyI-HF and StyI-WT

| Buffer | StyI-HF | | StyI-WT | | Improvement factor |
| --- | --- | --- | --- | --- | --- |
| | Relative Activity | FI | Relative Activity | FI | |
| NEB1 | 50% | ≥4000 | 25% | 32 | ≥125 |
| NEB2 | 100% | 2000 | 100% | 16 | 125 |
| NEB3 | 0.4% | ≥16 | 50% | 32 | ≥0.5 |
| NEB4 | 50% | 4000 | 25% | 16 | 250 |

StyI-WT and StyI-HF had the most activity in NEB2. The FI for StyI-WT was 16 and for StyI-HF was 2000. The overall FI improvement factor was 125.

Example 6: Engineering HF BsaJI

1. Expression of BsaJI

BsaJI was expressed in *E. coli* transformed with pRRS-BsaJIR+M, which contains BsaJI endonuclease and methylase gene in same plasmid.

The cells were grown at 37° C. overnight in LB with Amp and Cam.

2. Mutagenesis of BsaJI-HF

All residues Cys, Asp, Glu, Gly, His, Lys, Asn, Pro, Gln, Arg, Ser, Thr, Phe, Trp, were changed to Ala at positions 9, 10, 14, 17, 18, 19, 20, 22, 23, 24, 27, 30, 32, 35, 39, 42, 43, 48, 50, 51, 52, 53, 55, 56, 57, 60, 61, 65, 66, 67, 68, 70, 71, 72, 73, 78, 79, 81, 83, 84, 86, 87, 88, 90, 91, 92, 94, 95, 99, 101, 103, 104, 106, 110, 111, 113, 114, 117, 119, 120, 121, 123, 127, 129, 131, 132, 134, 136, 138, 140, 141, 142, 147, 152, 153, 157, 158, 159, 162, 163, 165, 166, 167, 169, 170, 175, 178, 181, 183, 184, 185, 186, 187, 188, 189, 194, 196, 197, 198, 199, 200, 202, 203, 204, 206, 211, 212, 213, 214, 215, 216, 218, 220, 222, 225, 226, 227, 228, 229, 230, 231, 233, 238, 239, 240, 241, 246, 247, 249, 250, 251, 252, 253, 254, 255, 257, 260, 262, 265, 267, 268, 269, 270, 271, 273, 274, 276, 277, 280, 281, 282, 283, 285, 287, 288, 290, 291, 293, 294, 295, 298 and 299; while Tyr is changed to Phe at the positions of 21, 59, 62, 77, 89, 105, 130, 191, 208, 272, 286 and 296.

The mutagenesis methods were inverse PCR with paired primers followed by DpnI digestion. The treated product was then transformed into *E. coli* strain ER3081.

3. Selection of BsaJI-HF

Selection of BsaJI-HF was achieved using comparison of activity in NEB3 and NEB4 using pBR322 DNA as substrate. E198A and D200A have highest activity. D200A has much lower star activity than WT in NEB4. BsaJI (D200A) is designated as BsaJI-HF.

4. Purification of BsaJI-HF

Two liters of cell ER3081 (pRRS-BsaJIR(D200A)+M) were grown in LB with 100 μg/ml Amp, 33 μg/ml Cam and 0.5 mM IPTG at 37° C. for overnight. The cells were harvested and sonicated in 50 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated by Amicon® Ultra 30 KDa (Millipore, U.S.A; now Merck, Germany). The concentrated BsaJI-HF was then added same volume of glycerol and stored at −20° C.

5. Comparison of BsaJI-HF and BsaJI-WT

The FIs of BsaJI-HF and WT BsaJI have been determined separately on pBR322 DNA in four NEB buffers with diluent A. The result is listed in Table 7.

TABLE 7

Comparison of BsaJI-HF and BsaJI-WT

| Buffer | BsaJI-HF Activity | FI | BsaJI-WT Activity | FI | Improvement Factor |
|---|---|---|---|---|---|
| NEB1 | 25% | ≥1000 | 100% | 64 | ≥15 |
| NEB2 | 100% | ≥4000 | 100% | 64 | ≥60 |
| NEB3 | 100% | ≥4000 | 25% | 16 | ≥250 |
| NEB4 | 100% | ≥4000 | 100% | 64 | ≥60 |

BsaJI-HF performed best in NEB2, 3 and 4, in which the FI was ≥4000; WT BsaJI performed best in NEB1, 2 and 4, in which the FI was 64. So the improvement factor in NEB4 was ≥4000/64≥64.

Example 7: Engineering of HF BsaWI

1. Expression of BsaWI

BsaWI was expressed in *E. coli* transformed with pLacZZ1-BsaWIR and pACYC-MspIM, each contains BsaWI endonuclease and methylase gene. The cells were grown at 30° C. overnight in LB with Amp and Cam and induced at 30° C. with 0.5 mM of IPTG for 18 hours.

2. Mutagenesis of BsaWI-HF

All residues Cys, Asp, Glu, Gly, His, Lys, Asn, Pro, Gln, Arg, Ser, Thr were changed to Ala at positions 9, 10, 13, 16, 17, 18, 20, 23, 24, 25, 26, 28, 29, 30, 31, 34, 35, 36, 39, 42, 43, 45, 46, 48, 51, 54, 58, 60, 62, 63, 64, 65, 66, 69, 70, 71, 74, 75, 78, 80, 81, 82, 84, 85, 86, 88, 89, 92, 93, 96, 99, 100, 101, 102, 104, 105, 107, 109, 113, 114, 115, 117, 121, 112, 123, 124, 127, 128, 129, 130, 131, 133, 136, 137, 138, 140, 141, 142, 145, 149, 151, 152, 153, 154, 155, 156, 160, 163, 164, 165, 166, 167, 169, 170, 171, 173, 174, 175, 176, 177, 178, 179, 181, 184, 189, 195, 196, 197, 200, 202, 203, 209, 210, 211, 212, 213, 214, 216, 218, 219, 221, 222, 228, 229, 230, 231, 233, 234, 237, 239, 241, 243, 247, 248, 250, 251, 254, 255, 258, 259, 260, 261, 264, and 266; while Tyr is changed to Phe at the positions of 11, 57, 106, 147, 157, 215, 224, 236, and 265.

The mutagenesis methods were inverse PCR with paired primers followed by DpnI digestion. The treated product was then transformed into *E. coli* strain ER3081.

3. Selection of BsaWI-HF

Selection of BsaWI-HF was achieved using comparison of activity in NEB3 and NEB4 using lambda DNA as substrate. The following mutants showed changes: K229A, E025A, R034A and Q261A. WT BsaWI can complete digestion in both buffers when grown in small culture; Q261A was noticed to only give a stable partial pattern. This could be due to the fact that the mutant grew poorly in small culture. When grown in large culture and purified, the partial pattern was eliminated and the substrate was instead digested completely, and the results also proved to be a high-fidelity mutant when tested upon the substrate pXba.

4. Purification of BsaWI-HF

Two liters of cell ER3081(pLacZZ1-BwaWI(Q261A), pACYC-MspIM)) were grown in LB with 100 μg/ml Amp and 33 μg/ml at 30° C. for overnight. After 8 hours, the culture was induced with 0.5 mM IPTG. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BsaWI-HF was then added an equal volume of glycerol and stored at −20° C.

5. Comparison of BsaWI-HF and BsaWI-WT

The FIs of BsaWI-HF and BsaWI-WT have been determined separately on pXba DNA in four NEB buffers with diluent A. The result is listed in Table 8 (below).

TABLE 8

Comparison of BsaWI-HF and BsaWI-WT

| Buffer | BsaWI-HF Activity | FI | BsaWI-WT Activity | FI | Improvement Factor |
|---|---|---|---|---|---|
| NEB1 | 1.6% | 8 | 12.5% | 4 | 2 |
| NEB2 | 100% | 120 | 50% | 8 | ≥15 |
| NEB3 | 3.1% | ≥250 | 3.1% | 64 | ≥4 |
| NEB4 | 100% | ≥4000 | 100% | 16 | ≥250 |

BsaWI-HF is most active in NEB2 and NEB4, in which the best FI is ≥4000; BsaWI-WT is most active in NEB4, in which the FI is 16. The overall improvement factor is ≥4000/16=~250.

Example 8: Engineering of High Fidelity BglI

1. Expression of BglI

BglI was expressed in *E. coli* transformed with pUC19-BglIR and pSYX20-BglIM, each contains BglI endonuclease and methylase gene. The cells were grown at 37° C. overnight in LB with Amp and Kan.

2. Mutagenesis of BglI-HF

All residues Cys, Asp, Glu, Gly, His, Lys, Asn, Pro, Gln, Arg, Ser, Thr were changed to Ala at positions 7, 8, 12, 14, 15, 16, 17, 18, 19, 22, 23, 24, 25, 27, 28, 29, 31, 34, 36, 39, 40, 43, 44, 45, 46 47, 48, 50, 52, 54, 5, 57, 60, 61, 65, 67, 68, 70, 71, 72, 73, 75, 76, 77, 78, 79, 81, 84, 86, 87, 88, 91, 92, 94, 95, 96, 99, 100, 101, 102, 103, 105, 107, 108, 110, 112, 113, 114, 115, 116, 117, 118, 122, 123, 124, 125, 128, 130, 131, 132, 134, 135, 136, 152, 158, 159, 160, 161, 163, 164, 165, 166, 167, 170, 172, 173, 174, 176, 177, 178, 179, 180 181, 183, 184, 185, 186, 187, 188, 189, 193, 194, 196, 197, 202, 203, 204, 205, 208, 211, 215, 216, 221, 222, 224, 225, 226, 227, 228, 229, 230, 231, 234, 236, 239, 241, 242, 243, 245, 249, 250, 251, 255, 256, 259, 263, 264, 265, 266, 267, 268, 269, 270, 271, 272, 275, 276, 277, 279, 281283, 286, 287, 289, 290, and 291; while Tyr is changed to Phe at the positions of 19, 13, 33, 53, 66, 119, 127, 153, 199, 218, 233, 252, and 258.

The mutagenesis methods were inverse PCR with paired primers followed by DpnI digestion. The treated product was then transformed into *E. coli* strain ER2566.

3. Selection of BglI-HF

Selection of BglI-HF was achieved using comparison of activity in NEB4 using lambda DNA as substrate. BglI-WT has low activity in NEB4, so any mutants with similar or more activity than WT in NEB4 were selected, then they were checked against glycerol for comparison of star activity levels. Only one mutant, K225A, showed similar activity to WT in NEB4 while also decreasing star activity when tested in glycerol. BglI(K225A) is designated as BglI-HF.

4. Purification of BglI-HF

Two liters of cell ER2566(pUC19-BglI(K225A), pSYX20-BglIM) were grown in LB with 100 μg/ml Amp and 33 μg/ml Kan at 37° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BglI-HF was then added to an equal volume of glycerol and stored at −20° C.

5. Comparison of BgiII-HF and BgiII-WT

Figure 6:
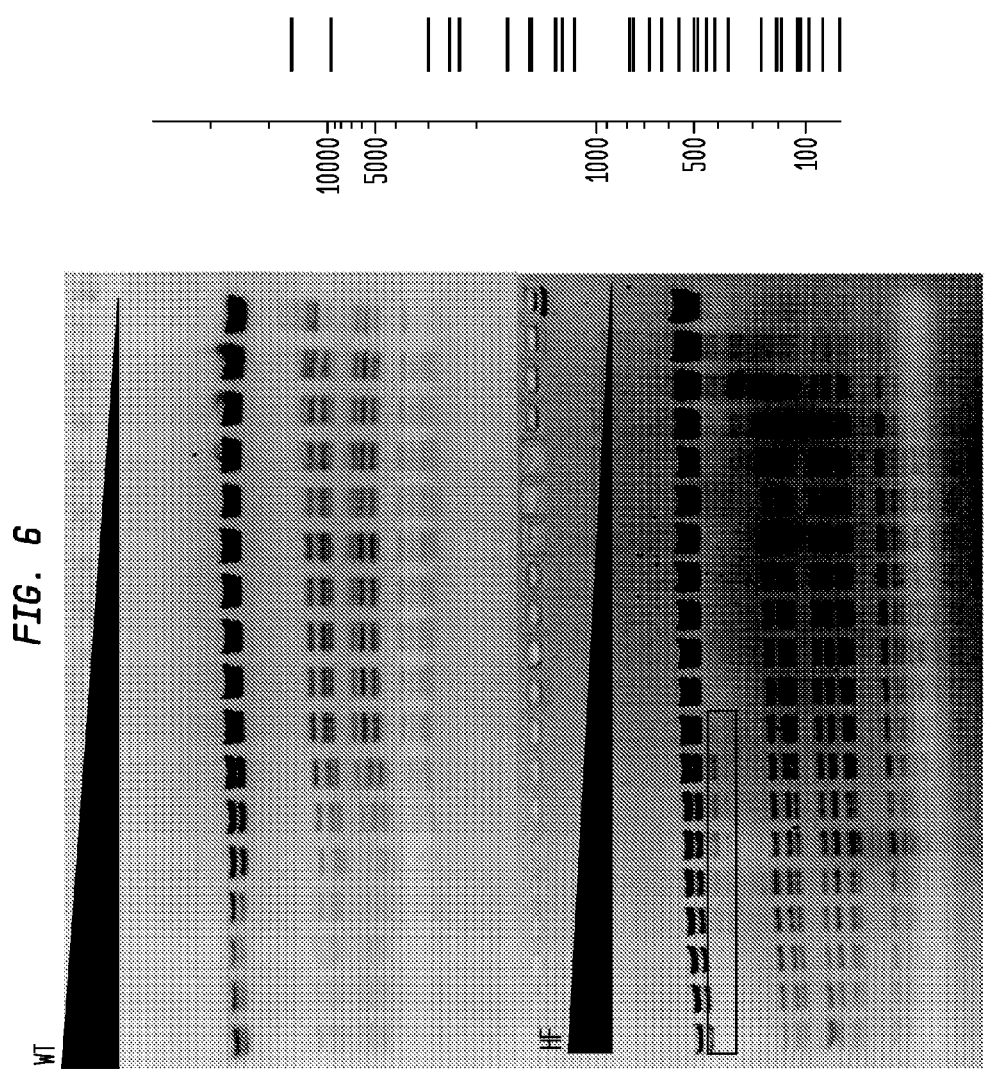
FIG. 6 shows a comparison of BglI-HF and BglI-WT on pXba. The BglI-HF has an FI of at least 8,000 while the BglI-WT has an FI of 32, providing an improvement factor of at least 250. The right panel is the theoretical digestion pattern.

The FIs of BglI-HF and WT BglI have been determined separately on lambda DNA in four NEB buffers with diluent B. The comparison is shown in FIG. 6, and the result is listed in Table 9 (below).

TABLE 9

Comparison of BglI-HF and BglI-WT

| Buffer | BglI-HF Activity | BglI-HF FI | BglI-WT Activity | BglI-WT FI | Improvement Factor |
|---|---|---|---|---|---|
| NEB1 | 50% | ≥4000 | 25.0% | 64 | ≥62 |
| NEB2 | 100% | ≥8000 | 100% | 64 | ≥125 |
| NEB3 | 6.3% | ≥500 | 100% | 250 | ≥2 |
| NEB4 | 100% | ≥8000 | 50% | 32 | ≥250 |

BglI-HF was most active in NEB2 and NEB4, in which the FI was ≥8000; BglI-WT is most active in NEB3, in which the FI was 250. The overall improvement factor was ≥8000/250=≥32.

Example 9: Engineering of HF BsrDI

1. Expression of BsrDI

BsrDI enzyme contains two subunits: BsrDIA and BsrDIB.

To obtain a pure BsrDIA subunit, the IMPACT (Intein-Mediated Purification with an Affinity Chitin-Binding Tag) system (NEB cat: E6901) was used for the one-step purification of BsrDIA. Briefly, the BsrDIA gene was sub-cloned into the pTXB1 vector, which was then transformed into a competent strain containing the T7 RNA polymerase, controlled by the lac operon (NEB #ER2566). After screening and sequencing, the corrected strain was selected. Cells were grown in LB media with Ampicillin (100 μg/ml) at 37° C. until the OD$_{600}$ reached 0.5. Then, IPTG was added to reach a final concentration of 0.4 mM for the induction of BsrDIA for 3 hours. Cell culture was then pelleted, resuspended in ice-cold Column Buffer (20 mM Tris-HCl, pH 8.5, 500 mM NaCl) and lysed via sonication. The resulting cell lysate was then centrifuged to remove cellular debris. Next, the supernatant was loaded onto an equilibrated Chitin Column. After washing with the loading buffer, the column was incubated with cleavage buffer (20 mM Tris-HCl, pH 8.5, 500 mM NaCl and 50 mM DTT) at 4° C. overnight. Finally, the BtsI.A protein was eluted with dialysis against the storage buffer (10 mM Tris-HCl pH 7.4, 0.1 mM EDTA, 1 mM DTT, 50 mM KCl and 50% glycerol).

BsrDIB subunit was expressed in *E. coli* transformed with pUC19-BsrDIBR and pLG-BsrDIM1M2, each contains BsrDI endonuclease and methylase gene. The cells were grown at 37° C. overnight in LB with Amp and Kam.

2. Mutagenesis of BsrDI-HF

All residues of BsrDIB including Cys, Asp, Glu, Gly, His, Lys, Asn, Pro, Gln, Arg, Ser, Thr were changed to Ala at positions 7, 11, 12, 14, 15, 17, 21, 22, 25, 28, 29, 30, 33, 34, 35, 37, 40, 45, 46, 47, 51, 52, 56, 58, 62, 64, 65, 67, 68, 71, 72, 74, 75, 81, 83, 90, 91, 92, 93, 99, 100, 101, 106, 108, 109, 112, 113, 115, 116, 120, 122, 123, 124, 132, 133, 136, 137, 138, 139, 142, 143, 144, 145, 146, 150, 155, 157, 158, 161, 162, 164, 168, 170, 171, 173, 174, 176, 177, 179, 180, 182, 185, 189, 190, 193, 197, 200, 202, 203, 206, 210, 213, 215, 217, 218, 221, 224, 225, 226, 228, 229, 230, 232, 237, 238, 241, 242, 243, 244, 245, 246, 249, 253, 258, 259, 261, 264, 265, 268, 271, 272, 273, 274, 276, 278, 279, 281, 285, 287, 288, 292, 294, 295, 299, 300, 301, 306, 307, 308, 312, 314, 315, 317, 318, 320, 321, 324, 325, 326, 327, 328, 331, 332, 335, 337, 341, 343, 345, 347, 352, 353, 354, 355, 356, 360, 361, 362, 363, 364, 370, 373, 374, 376, 380, 381, 385, 387, 389, 392, 393, 395, 396, 397, 405, 406, 408, 411, 415, 418, 420, 422, 425, 426, 430, 431, 432, 434, 437, 445, 446, 449, 450, 454, 455, 456, 457, 458, 459, 460, 463, 465, 466, 467, 469, 470, 475, 481; while Tyr is changed to Phe at the positions of 9, 38, 63, 87, 118, 129, 169, 178, 198, 216, 251, 286, 291, 303, 357, 358, 367, 371, 402, 442, 443, 448.

The mutagenesis methods were inverse PCR with paired primers followed by DpnI digestion. The treated product was then transformed into *E. coli* strain ER2566.

3. Selection of BsrDI-HF

Selection of BsrDI-HF was achieved using comparison of star activity between the WT BsrDIB mixed with BsrDIA and the mutant BsrDIB mixed with BsrDIA in NEB4 on pBR322 DNA as substrate. Eight mutants are found to have less star activity in NEB4:H137A, D177A, K363A, K408A, R411A, Q215A, Q226A, Q230A.

To further reduce the star activity, we combine the above mutations to make double mutations: K363A/Q230A, K363A/K408A, Q230A/K408A. Then BsrDI with mutations on BsrDIB of Q230A/K363A is designated as BsrDI-HF.

4. Purification of BsrDI-HF

Two liters of cell ER2566(pUC19-BsrDI(Q230A/K363A), pLG-BsrDIM1M2)) were grown in LB with 100 μg/ml Amp and 33 μg/ml Kam at 37° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated by Vivaspin® 15R (Vivascience, now Sartorius Vivascience GmbH, Goettingen, Germany). The concentrated BsrDI-HF was then added same volume of glycerol and stored at −20° C. condition.

5. Comparison of BsrDI-HF and BsrDI-WT

Figure 7:
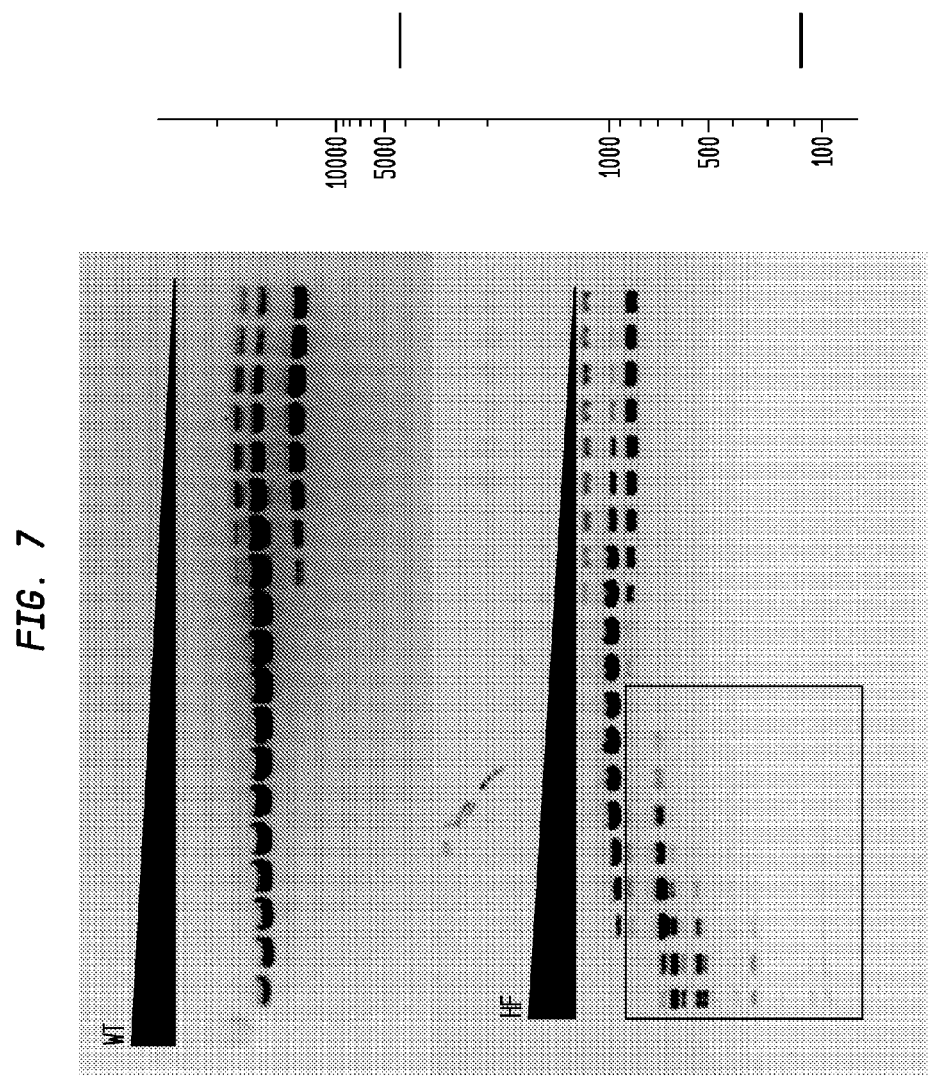
FIG. 7 shows a comparison of BsrDI-HF and BsrDI-WT on pBR322. The BsrDI-HF has an FI of at least 1,000 in NEB4, while the BsrDI-WT has an FI of ½, providing an improvement factor of at least 2,000. The right panel is the theoretical digestion pattern.

The FIs of BsrDI-HF and BsrDI-WT have been determined separately on pBR322 DNA in four NEB buffers with diluent A. The result is shown in FIG. 7 and listed in Table 10 (below).

TABLE 10

Comparison of BsrDI-HF and BsrDI-WT

| Buffer | BsrDI-HF | | BsrDI-WT | | Improvement |
|---|---|---|---|---|---|
| | Activity | FI | Activity | FI | Factor |
| NEB1 | 12.5% | ≥120 | 6% | 1 | ≥120 |
| NEB2 | 100% | ≥500 | 100% | 4 | ≥120 |
| NEB3 | 6% | ≥64 | 12.5% | 4 | ≥16 |
| NEB4 | 100% | ≥1000 | 25% | ½ | ≥2000 |

BsrDI-HF performed best in NEB4, in which the FI was ≥1000; BsrDI-WT performed best in NEB2 and NEB3, in which the FI was 64. So the overall improvement factor was ≥1000/0.5=≥2000.

Example 10: Engineering of HF NsiI

1. Expression of NsiI

NsiI was expressed in *E. coli* transformed with placzz1-NsiIR and pACYC-NsiIM, each contains NsiI endonuclease and methylase gene. The cells were grown at 37° C. overnight in LB with Amp and Cam.

2. Mutagenesis of NsiI-HF

All residues Cys, Asp, Glu, Gly, His, Lys, Asn, Pro, Gln, Arg, Ser, Thr, Phe, Trp, were changed to Ala at positions 8, 9, 10, 11, 12, 13, 18, 21, 22, 23, 24, 26, 27, 32, 34, 35, 42, 44, 45, 46, 47, 49, 50, 52, 53, 54, 55, 57, 58, 60, 61, 69, 70, 73, 74, 79, 80, 84, 85, 87, 90, 91, 92, 93, 95, 96, 97, 98, 99, 100, 102, 103, 105, 106, 108, 109, 110, 113, 114, 115, 117, 118, 119, 120, 121, 122, 123, 124, 126, 134, 135, 137, 138, 139, 140, 142, 144, 145, 146, 149, 151, 153, 154, 155, 156, 159, 160, 161, 162, 163, 166, 167, 170, 173, 174, 175, 178, 179, 180, 181, 182, 183, 184, 186, 188, 189, 190, 191, 192, 195, 197, 198, 199, 200, 201, 202, 203, 206, 207, 209, 210, 211, 213, 215, 216, 217, 219, 221, 222, 225, 230, 231, 232, 234, 235, 236, 237, 239, 242, 243, 244, 245, 246, 249, 250, 251, 256, 257, 259, 260, 261, 263, 264, 268, 269, 271, 272, 273, 276, 277, 278, 279, 281, 282, 283, 285, 287, 288, 290, 292, 294, 295, 297, 298, 299, 302, 303, 306, 307, 308, 309, 310, 312, 315, 316, 319, 320, 323, 325, 327, 329, 333, 334, 336, 337, 338, 340, 341, 344, 347, 349, 350, 352, 353, 354, 355, 358, 359, 360, 362, 363, 365, 366, 367, 371, 372, 373, 375, 376 and 377; while Tyr is changed to Phe at the positions of 30, 40, 62, 65, 71, 76, 83, 86, 141, 226, 233, 255, 289, 311, 326, 335, 351, 357, 378.

The mutagenesis methods were inverse PCR with paired primers followed by DpnI digestion. The treated product was then transformed into *E. coli* strain ER3081.

3. Selection of NsiI-HF

Selection of NsiI-HF was achieved using comparison of activity in NEB3 and NEB4 using pXba DNA as substrate. NsiI-WT has more activity in NEB3, the one with more activity in NEB4 were selected. 148 mutants are found to have more activity in NEB4. F376A has much higher activity than WT in NEB4. Normally the one with highest activity in NEB4 is the one with improved star activity. NsiI (F376A) is designated as NsiI-HF.

4. Purification of NsiI-HF

Two liters of cell ER3081 (placzz1-NsiI(F376A), pACYC-NsiIM) were grown in LB with 100 μg/ml Amp, 33 μg/ml Cam and 0.5 mM IPTG at 37° C. for overnight. The cells were harvested and sonicated in 50 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated by Amicon Ultra 30 KDa (Millipore, U.S.A; now Merck, Germany). The concentrated NsiI-HF was then added same volume of glycerol and stored in the −20° C. condition.

5. Comparison of NsiI-HF and NsiI-WT

The FIs of NsiI-HF and WT NsiI have been determined separately on pXba DNA in four NEB buffers with diluent A. The result is listed in Table 11 (below).

TABLE 11

Comparison of NsiI-HF and NsiI-WT

| Buffer | NsiI-HF | | NsiI-WT | | Improvement |
|---|---|---|---|---|---|
| | Activity | FI | Activity | FI | Factor |
| NEB1 | 3% | ≥250 | 6.3% | 32 | ≥8 |
| NEB2 | 12.5% | ≥1000 | 25% | 32 | ≥30 |
| NEB3 | 6% | ≥500 | 100% | 32 | ≥15 |
| NEB4 | 100% | ≥8000 | 12.5% | 32 | ≥250 |

NsiI-HF performed best in NEB4, in which the FI was ≥8000; WT NsiI performed best in NEB3, in which the FI was 32. So the improvement factor in NEB4 was ≥8000/32=≥250.

Example 11: Engineering of HF DpnII

1. Expression of DpnII

DpnII was expressed in *E. coli* 3081 transformed with pBAD241-DpnII RM. The cells were grown at 30° C. overnight in LB with Amp.

2. Mutagenesis of DpnII

The point mutagenesis of the selected mutations was done by inverse PCR. 189 amino acid mutations were made in DpnII as follows. Cys, Asp, Glu, Phe, His, Lys, Met, Asn, Gln, Arg, Ser, Thr, Trp were mutated to Ala. Try was mutated to Phe. These were: 7, 8, 9, 10, 12, 13, 14, 15, 16, 17, 19, 20, 21, 22, 23, 24, 25, 26, 27, 29, 31, 32, 33, 35, 36, 38, 40, 42, 44, 45, 46, 50, 51, 52, 54, 55, 56, 57, 59, 61, 62, 63, 64, 66, 69, 76, 77, 78, 80, 81, 82, 86, 87, 90, 91, 92, 93, 94, 95, 96, 97, 98, 99, 100, 101, 102, 104, 105, 106, 107, 108, 109, 111, 112, 113, 116, 117, 118, 120, 121, 122, 125, 126, 129, 130, 132, 135, 138, 139, 140, 141, 143, 144, 145, 146, 147, 149, 150, 151, 152, 153, 156, 157, 158, 160, 161, 162, 164, 168, 169, 171, 172, 173, 175, 176, 177, 178, 180, 181, 183, 184, 186, 188, 189, 191, 192, 193, 195, 196, 198, 199, 200, 201, 202, 205, 206, 207, 208, 211, 214, 216, 217, 218, 219, 221, 223, 224, 226, 227, 228, 229, 230, 231, 232, 233, 234, 236, 237, 238, 239, 240, 241, 244, 246, 247, 248, 249, 251, 252, 254, 256, 257, 258, 259, 260, 261, 262, 264, 265, 266, 267, 268, 272, 274, 275, 277, 278, 280, 281 and 282.

The method of primer design and PCR is similar to that described previously. The PCR product was digested with DpnI and transformed into competent E. coli 3081.

3. Selection of DpnII-HF

Four colonies of each mutation were grown up in LB with Amp at 37° C. overnight. The standard screening assays of DpnII were performed using dam⁻ lambda substrate in NEB4 buffer and 5% glycerol.

The mutants R78A, T140A, E152A, R199A, and F217A were picked out from screening assay. After several rounds of comparison in different conditions and substrates, R199A was chose as candidate, retaining high canonical enzyme activity, but displaying substantially reduced star activity. R199A was labeled as DpnII-HF.

4. Purification of DpnII-HF

Two liters of cell E. coli 3081 (pBAD241.DpnII.RM (R199A)) were grown in LB with 100 ug/ml Amp at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated. The concentrated Bmt-HF was then added same volume of glycerol and stored in the −20° C. condition.

5. Comparison of DpnII-HF and DpnII-WT

DpnII-HF was 2-fold serial diluted with B and reacted in four NEB buffers, and DpnII-WT was 2-fold serial diluted and reacted in four NEB buffers. The result is listed in Table 12.

TABLE 12

Comparison of DpnII-HF and DpnII-WT

| Buffer | DpnII-HF | | DpnII-WT | | Improvement |
| | Activity | FI | Activity | FI | Factor |
| --- | --- | --- | --- | --- | --- |
| NEB1 | 50% | 4000 | 25% | 1 | 4000 |
| NEB2 | 25% | 2000 | 25% | 1 | 2000 |
| NEB3 | 0.8% | 64 | 100% | 32 | 2 |
| NEB4 | 100% | 8000 | 25% | 1 | 8000 |

DpnII-HF performed best in NEB4, in which the preferred FI was =8000; DpnII performed best in NEB3, where the FI was 32. The overall FI improvement factor was 8000/32=250.

Example 12: Engineering of High Fidelity BclI

1. Expression of BclI

BclI was expressed in E. coli transformed with pRRS-BclIR and pACYC184-BclIM, each contains BclI endonuclease and methylase gene.

The cells were grown at 37° C. overnight in LB with Amp.

2. Mutagenesis of BclI-HF

All residues Cys, Asp, Glu, Gly, His, Lys, Asn, Pro, Gln, Arg, Ser, Thr were changed to Ala at positions 9, 10, 11, 12, 19, 22, 23, 24, 26, 28, 29, 30, 31, 35, 37, 38, 40, 42, 44, 46, 47, 49, 51, 53, 54, 55, 58, 59, 62, 65, 67, 69, 72, 73, 74, 75, 76, 80, 82, 83, 85, 86, 89, 93, 94, 95, 96, 97, 98, 99, 101, 103, 105, 107, 108, 109, 110, 111, 112, 113, 114, 115, 120, 124, 128, 129, 130, 132, 136, 137, 138, 139, 143, 144, 145, 149, 150, 151, 152, 154, 156, 160, 162, 163, 164, 166, 167, 170, 171, 172, 174, 175, 178, 179, 180, 182, 183, 188, 190, 191, 195, 196, 197, 199, 200, 201, 204, 205, 208, 209, 210, 212, 213, 215, 217, 218, 220, 221, 222, 223, 224, 225, 226, 228, 229, 234, 235, 237, 238, 241, 243, 244, 245, 249, 252, 255, 257, 260, 261, 265, 266, 267, 270, 271, 273, 274, and 277; while Tyr is changed to Phe at the positions of 17, 27, 36, 63, 66, 77, 87, 100, 116, 118, 133, 142, 147, 157, 192, 193, 194, 207, 212, 231, 236, and 246.

The mutagenesis methods were inverse PCR with paired primers followed by DpnI digestion. The treated product was then transformed into E. coli strain ER2984.

3. Selection of BclI-HF

Selection of BclI-HF was achieved using comparison of activity in glycerol and NEB4 using dam− lambda DNA as the substrate. Once lower star activity was suspected, mutants were also compared with normal activity in water and NEB4 on the same substrate. Mutants with similar activity to WT in NEB4 and also with the potential to have lower star activity were selected. 6 mutants are found to have such characteristics: G26A, P105A, T195A, Q210A, Y147F, and Y193F. Several mutants (K114A, T197A, S245A, D252A, and Y027F) showed lower activity in water, but decreased star activity as well; they usually had higher activity cognate activity than WT under high glycerol conditions. One mutant showed higher activity than WT and also lower star activity: Y192F. BclI(Y192F) is designated as BclI-HF.

4. Purification of BclI-HF

Two liters of cell ER2984(pRRS-BclI(Y192F), pACYC184-BclIM)) were grown in LB with 100 µg/ml Amp at 37° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BclI-HF was then added to an equal volume of glycerol and stored at −20° C.

5. Comparison of BclI-HF and BclI-WT

The FIs of BclI-HF and BclI-WT have been determined separately on dam− lambda DNA in four NEB buffers with diluent A. The comparison is shown in FIG. 8, and the result is listed in Table 13 (below).

TABLE 13

Comparison of BclI-HF and BclI-WT

| Buffer | BclI-HF | | BclI-WT | | Improvement |
| | Activity | FI | Activity | FI | Factor |
| --- | --- | --- | --- | --- | --- |
| NEB1 | 12.5% | ≥250 | 50% | 120 | ≥2 |
| NEB2 | 100% | ≥500 | 100% | 32 | ≥16 |
| NEB3 | 25% | ≥32 | 50% | 64 | ≥½ |
| NEB4 | 100% | ≥2000 | 100% | 32 | ≥60 |

BclI-HF performed best in NEB2 and NEB4, in which the best FI was ≥2000; BclI-WT performed best in NEB2 and NEB4, in which the FI was 32. The overall improvement factor is ≥2000/32=≥64.

Example 13: Engineering of HF BglII

1. Expression of BglII

BglII was expressed in *E. coli* transformed with pLacZZ-BglIIR and pACYC-BglIIM, each contains BglII endonuclease and methylase gene. The cells were grown at 37° C. overnight in LB with Amp and Cam.

2. Mutagenesis of BglII-HF

All residues Cys, Asp, Glu, Gly, His, Lys, Asn, Pro, Gin, Arg, Ser, Thr were changed to Ala at positions 2, 4, 6, 7, 9, 10, 12, 13, 16, 18, 20, 21, 22, 24, 25, 26, 29, 30, 33, 35, 37, 38, 39, 41, 42, 45, 48, 49, 53, 54, 55, 58, 59, 60, 64, 65, 66, 67, 68, 69, 74, 75, 76, 77, 78, 81, 82, 84, 85, 87, 88, 89, 90, 93, 95, 96, 97, 98, 101, 104, 105, 106, 108, 109, 110, 112, 113, 114, 115, 116, 117, 118, 120, 121, 122, 124, 125, 131, 132, 134, 135, 136, 139, 140, 141, 142, 146, 147, 149, 150, 151, 153, 154, 157, 159, 161, 162, 166, 172, 173, 174, 175, 176, 177, 179, 182, 183, 184, 187, 188, 189, 191, 192, 193, 195, 196, 197, 198, 199, 201, 203, 206, 207, 208, 209, 211, 212, 213, 214, 215, 216, 217, 219, 222; while Tyr is changed to Phe at the positions of 8, 56, 99, 144, 145, 158, 185, and 190.

The mutagenesis methods were inverse PCR with paired primers followed by DpnI digestion. The treated product was then transformed into *E. coli* strain ER3081.

3. Selection of BglII-HF

Selection of BglII-HF was achieved using comparison of activity in NEB3 and NEB4 using pXba DNA as substrate. BglII-WT has more activity in NEB3, so the mutants with more activity in NEB4 were selected. All mutants with more activity were then compared to WT activity in glycerol to check for star activity. Normally the mutant with the highest activity in NEB4 is the one with improved star activity. The mutants that were most promising (H10A, N208A, K48A, K74A, R75A, Y56F, K58A, M117A) were finally tested with ExoI buffer in water, which can promote star activity in BglI-WT. One mutant, N208A showed decreased star activity in NEB4 and increased overall activity. In small culture, this mutant can appear to have stable partial activity, which we have determined is another indicator that the fidelity has changed. BglII(N208A) is designated as BglII-HF.

4. Purification of BglII-HF

Two liters of cell ER3081(pLacZZ-BglII(N208A), pACYC-BglIIM)) were grown in LB with 100 μg/ml Amp and 33 μg/ml at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BglII-HF was then added an equal volume of glycerol and stored at −20° C.

5. Comparison of BglII-HF and BglII-WT

Figure 9:
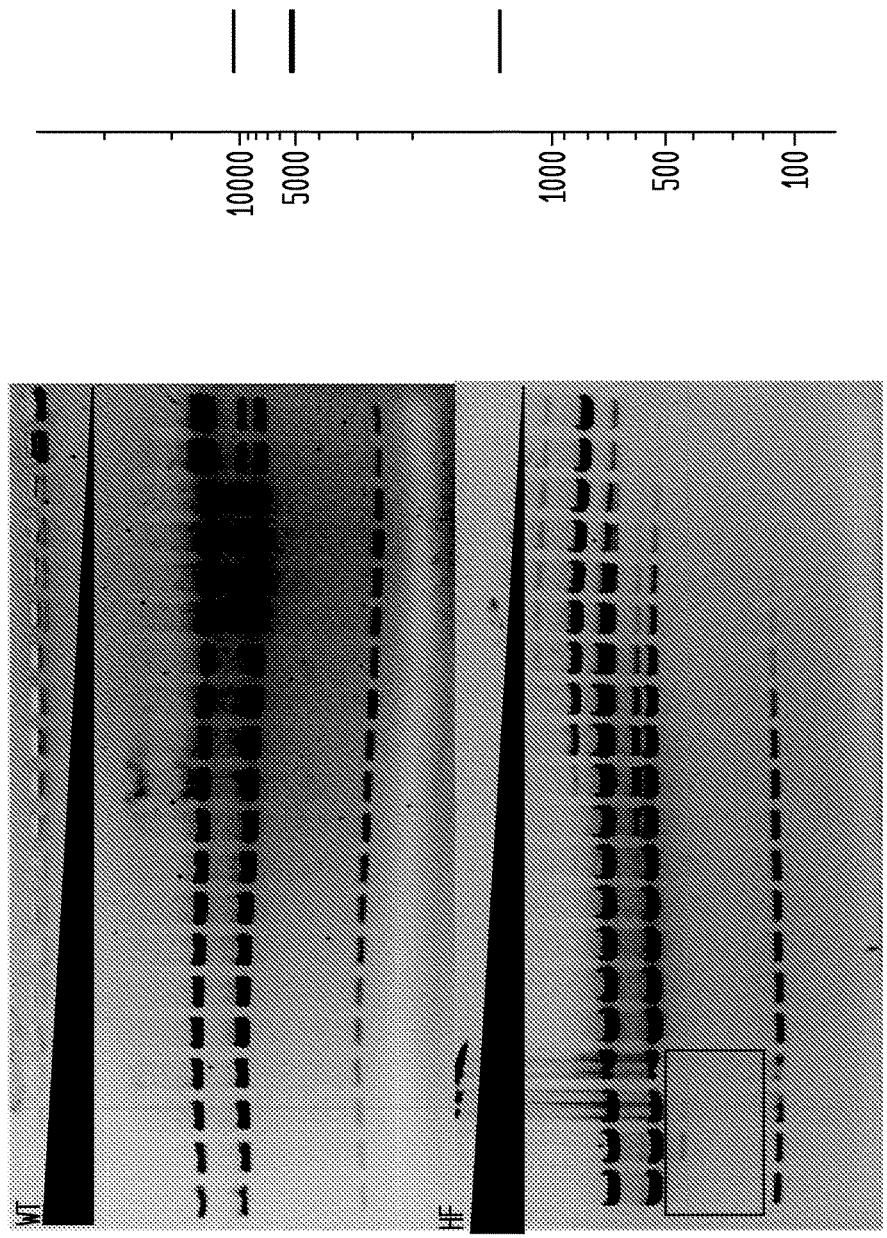
FIG. 9 shows a comparison of BglII-HF and BglII-WT on pXba. The BglII-HF has an FI of at least 32,000, while the BglII-WT has an FI of 16, providing an improvement factor of at least 2,000. The right panel is the theoretical digestion pattern.

The FIs of BglII-HF and BglII-WT have been determined separately on pXba DNA in four NEB buffers with diluent B. The comparison is shown in FIG. 9, and the result is listed in Table 14 (below).

TABLE 14

| | Comparison of BglII-HF and BglII-WT | | | | |
|---|---|---|---|---|---|
| | BglII-HF | | BglII-WT | | Improvement |
| Buffer | Activity | FI | Activity | FI | Factor |
| NEB1 | 12.5% | ≥8000 | 25% | 250 | ≥32 |
| NEB2 | 100% | ≥128000 | 100% | 64 | ≥2000 |
| NEB3 | 50% | ≥2000 | 100% | 120 | ≥16 |
| NEB4 | 25% | ≥32000 | 6.3% | 16 | ≥2000 |

BglII-HF performed best in NEB2, in which the FI was ≥128000; BglII-WT performed best in NEB3, in which the FI was 120. The overall improvement factor was ≥128000/120=≥1000.

Example 14: Engineering of HF BstEII

1. Expression of BstEII

BstEII was expressed in *E. coli* transformed with pUC19-BstEIIR and pACYC-BstEIIM, each contains BstEII endonuclease and methylase gene. The cells were grown at 37° C. overnight in LB with Amp and Cam.

2. Mutagenesis of BstEII-HF

All residues Cys, Asp, Glu, Gly, His, Lys, Asn, Pro, Gin, Arg, Ser, Thr were changed to Ala at positions 7, 9, 10, 14, 17, 20, 21, 22, 25, 26, 29, 30, 32, 36, 37, 40, 41, 44, 47, 48, 49, 50, 51, 52, 54, 57, 58, 60, 61, 62, 63, 64, 65, 67, 68, 69, 72, 75, 76, 79, 80, 81, 82, 83, 85, 88, 89, 90, 91, 92, 94, 95, 98, 99, 101, 102, 103, 105, 106, 111, 112, 113, 116, 117, 118, 119, 120, 121, 122, 123, 130, 132, 133, 134, 135, 136, 137, 138, 140, 142, 143, 147, 150, 151, 152, 154, 155, 157, 160, 161, 162, 163, 165, 166, 167, 171, 172, 175, 176, 178, 179, 180, 182, 184, 189, 190, 191, 192, 193, 194, 195, 199, 202, 204, 205, 206, 207, 208, 209, 211, 212, 213, 214, 215, 216, 217, 218, 219, 220, 221, 222, 224, 225, 227, 228, 232, 233, 234, 236, 238, 243, 244, 245, 246, 247, 251, 252, 255, 256, 258, 261, 262, 264, 265, 266, 272, 274, 277, 278, 279, 281; while Tyr is changed to Phe at the positions of 8, 15, 24, 27, 35, 43, 77, 129, 131, 139, 156, 188, 203, 229, 257, and 263.

The mutagenesis methods were inverse PCR with paired primers followed by DpnI digestion. The treated product was then transformed into *E. coli* strain ER2683.

3. Selection of BstEII-HF

Selection of BstEII-HF was achieved using comparison of activity in NEB3 and NEB4 using lambda DNA as substrate. WT BstEII has more activity in NEB3, so the mutants with more activity in NEB4 were selected. Seven mutants were found to have improved activity in NEB4: K014A, Q069A, E099A, R105A, R117A, G135A, and Y035F. R105A had the most difference in activity compared to WT in NEB4 and water and also showed decreased star activity when with tested in glycerol with ExoI buffer, a condition which shows star activity in WT. BstEII(R105A) is designated as BstEII-HF.

4. Purification of BstEII-HF

Two liters of cell ER2683(pUC19-BstEII(R105A), pACYC-BstEIIM)) were grown in LB with 100 μg/ml Amp and 33 μg/ml at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BstEII-HF was then added an equal volume of glycerol and stored at −20° C.

5. Comparison of BstEII-HF and WT BstEII

Figure 10:
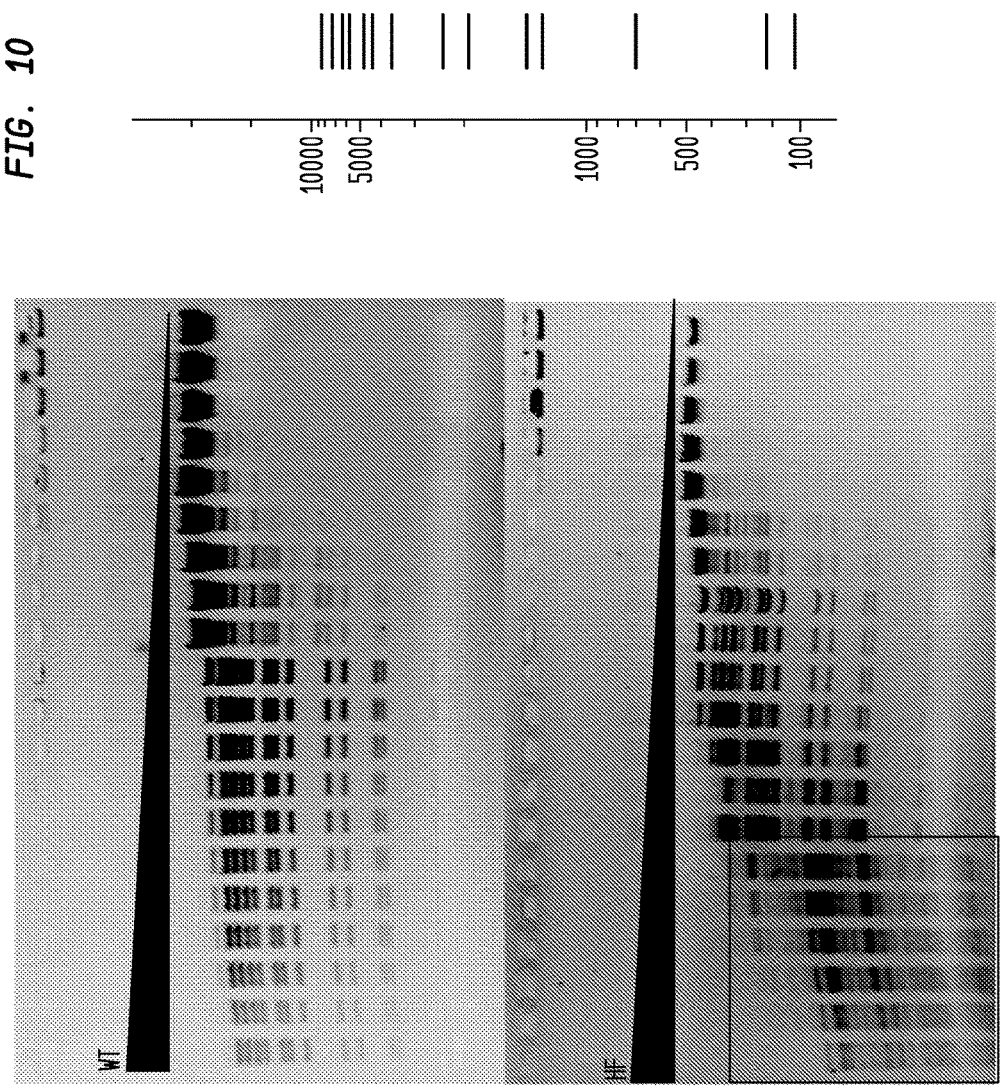
FIG. 10 shows a comparison of BstEII-HF and BstEII-WT on lambda DNA. The BstEII-HF has an FI of at least 2,000, while the BstEII-WT has an FI of 4, providing an improvement factor of at least 500. The right panel is the theoretical digestion pattern.

The FIs of BstEII-HF and WT BstEII have been determined separately on lambda DNA in four NEB buffers with diluent A. The comparison is shown in FIG. 10, and the result is listed in Table 15 (below).

TABLE 15

Comparison of BstEII-HF and BstEII-WT

| Buffer | BstEII-HF | | BstEII-WT | | Improvement |
| | Activity | FI | Activity | FI | Factor |
| --- | --- | --- | --- | --- | --- |
| NEB1 | 3% | ≥64 | 50% | 16 | ≥4 |
| NEB2 | 50% | ≥1000 | 100% | 4 | ≥250 |
| NEB3 | 1.6% | ≥32 | 50% | 16 | ≥2 |
| NEB4 | 100% | ≥2000 | 100% | 4 | ≥500 |

BstEII-HF performed best in NEB4, in which the FI was ≥2000; BstEII-WT performed best in NEB2 and NEB4, in which the FI was 4. The overall improvement factor is ≥2000/4=≥500.

Example 15: Engineering of HF BanII

1. Expression of BanII

BanII was expressed in *E. coli* transformed with pUC19-BanIIR and pACYC1-BanIIM, each contains BanII endonuclease and methylase gene. The cells were grown at 37° C. overnight in LB with Amp and Cam.

2. Mutagenesis of BanII-HF

All residues except Tyr (and those that were already Ala) were changed to Ala at positions 7, 8, 9, 10, 12, 16, 17, 20, 21, 23, 24, 25, 26, 28, 29, 24, 31, 32, 35, 38, 39, 43, 44, 45, 47, 49, 54, 59, 61, 63, 64, 66, 67, 71, 72, 73, 74, 75, 77, 78, 81, 83, 84, 87, 88, 92, 94, 95, 96, 97, 99, 100, 103, 104, 105, 106, 107, 108, 111, 112, 113, 115, 117, 118, 120, 121, 122, 123, 126, 127, 128, 129, 130, 131, 135, 139, 142, 143, 145, 146, 147, 148, 149, 152, 153, 155, 156, 163, 166, 167, 168, 169, 170, 171, 173, 175, 176, 178, 179, 180, 181, 183, 184, 186, 190, 191, 194, 195, 196, 198, 199, 200, 207, 208, 211, 213, 214, 215, 216, 219, 220, 221, 222, 224, 226, 229, 230, 231, 232, 234, 235, 236, 237, 239, 240, 242, 245, 246, 247, 248, 252, 254, 256, 257, 258, 259, 261, 262, 263, 264, 266, 267, 270, 271, 272, 274, 276, 278, 279, 281 284, 285, 286, 287, 289, 291, 292, 293, 294, 295, 296, 300, 302, 303, 305, 309, 311, 312, 314, 317, 318, 319, 322, 326, 327, 328, 330, 331, 334, 338, 339, 341, 342, 344, 346, 347, 348, 349, 351, 352, 355, 356, and 358; Tyr was changed to Phe at the positions of 27, 50, 80, 160, 182, 197, 244, 251, 260, 307, and 313.

The mutagenesis methods were inverse PCR with paired primers followed by DpnI digestion. The treated product was then transformed into *E. coli* strain ER2566.

3. Selection of BanII-HF

Selection of BanII-HF was achieved using by comparing the of activity in NEB4 with water with the star activity in ExoI buffer and glycerol, using lambda DNA as substrate. Mutants which showed similar or improved activity to WT in water and NEB4, while also showing improved star activity were selected for further testing. These mutants include N106A, Q169A, and E314A. R126A was also chosen because it showed a consistent partial pattern, which we have also shown to be an indicator of high fidelity. After purification, R126A showed the best decrease in star activity. BanII(R126A) is designated BanII-HF.

4. Purification of BanII-HF

Two liters of cell ER2566(pUC19-BanII(R126A), pACYC-BanIIM)) were grown in LB with 100 μg/ml Amp and 33 μg/ml at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BanII-HF was then added an equal volume of glycerol and stored at −20° C.

5. Comparison of BanII-HF and BanII-WT

The FIs of BanII-HF and BanII-WT have been determined separately on dam− lambda DNA in four NEB buffers with diluent A. The result is listed in Table 16 (below).

TABLE 16

Comparison of BanII-HF and BanII-WT

| Buffer | BanII-HF | | BanII-WT | | Improvement |
| | Activity | FI | Activity | FI | Factor |
| --- | --- | --- | --- | --- | --- |
| NEB1 | 100% | ≥4000 | 100% | 64 | ≥64 |
| NEB2 | 50% | ≥2000 | 100% | 64 | ≥32 |
| NEB3 | 12.5% | ≥500 | 12.5% | 16 | ≥32 |
| NEB4 | 50% | ≥2000 | 100% | 16 | ≥125 |

BanII-HF performed best in NEB1, in which the FI was ≥4000; BanII-WT performed best in NEB1, NEB2 and NEB4, in which the best FI was 64. So the overall improvement factor in NEB1 is ≥4000/64=≥64.

Example 16: Engineering of HF PspGI

1. Expression of PspGI

PspGI was expressed in *E. coli* transformed with pRRS-PspGIRM which contains PspGI endonuclease and methylase gene. The cells were grown at 30° C. overnight in LB with Amp.

2. Mutagenesis of PspGI-HF

The length of PspGI protein is 272 amino acids. Total 166 AA sites of PspGI protein were initially designed to be mutated into Ala (or Phe). Cys, Asp, Glu, Phe, His, Lys, Met, Asn, Gin, Arg, Ser, Thr, Trp were mutated to Ala. Try was mutated to Phe. These were: 8, 10, 11, 12, 13, 14, 15, 16, 18, 19, 20, 21, 22, 25, 26, 29, 30, 32, 34, 35, 38, 39, 42, 43, 44, 45, 46, 47, 48, 51, 52, 53, 54, 57, 60, 61, 62, 65, 68, 69, 71, 72, 73, 75, 76, 80, 82, 84, 85, 86, 87, 89, 90, 91, 93, 94, 96, 98, 99, 100, 101, 102, 105, 109, 110, 113, 134, 135, 136, 137, 138, 142, 143, 145, 149, 150, 151, 152, 153, 158, 160, 161, 162, 164, and 165. The mutagenesis methods were inverse PCR with paired primers followed by DpnI digestion. The treated product was then transformed into *E. coli* strain 2984.

3. Selection of PspGI-HF

Selection of PspGI-HF was achieved using comparison of mutants and WT's activity in NEB4 using pBC4 DNA as substrate. The selection assays of PspGI were performed using pBC4 as substrate in NEB4 (2 h digestion at 69° C.). 11 mutants are found to have more activity in NEB4 than WT: T20A, P52A, Y67F, K68A, R75A, E86A, Q90A, S91A, Q93A, H121A and G172A. PspGI (R75A) has much higher activity than WT in NEB4. Normally the one with highest activity in NEB4 is the one with improved star activity. After several rounds of comparison in different conditions and substrates, PspGI (R75A) was found to be the preferred mutant, retaining high cleavage high activity, but displaying substantially reduced star activity. PspGI (R75A) is designated as PspGI-HF.

4. Purification of PspGI-HF

Two liters of cell *E. coli* 2984 (pRRS-PspGIRM (R75A)) were grown in LB with 100 µg/ml Amp at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated. The concentrated PspGI-HF was then added same volume of glycerol and stored in the −20° C. condition.

5. Comparison of PspG-HF and PspGI-WT

The FIs of PspG-HF and PspGI-WT have been determined separately on pBC4 DNA in four NEB buffers with diluent A. The result is listed in Table 17 (below).

TABLE 17

Comparison of PspG-HF and PspGI-WT

| Buffer | PspGI-HF Activity | FI | PspGI-WT Activity | FI | Improvement Factor |
|---|---|---|---|---|---|
| NEB1 | 25% | ≥1000 | 12.5% | 1 | ≥1000 |
| NEB2 | 100% | ≥4000 | 100% | 4 | ≥1000 |
| NEB3 | 100% | ≥4000 | 100% | 8 | ≥500 |
| NEB4 | 100% | ≥4000 | 100% | 1 | ≥4000 |

PspGI-HF performed best in at NEB2, NEB3 and NEB4, in which the preferred FI was ≥4000; PspGI-WT performed best in NEB2, NEB3 and NEB4. The preferred FI of PspGI-WT in NEB3 was 8. The overall FI improvement factor was ≥4000/8=≥500.

Example 17: Engineering of HF SpeI

1. Expression of SpeI

SpeI was expressed in *E. coli* transformed with pRRS-SpeI and pASYX20-SpeIM9, each contains SpeI endonuclease and methylase gene. The cells were grown at 30° C. overnight in LB with Amp and Kan.

2. Mutagenesis of SpeI-HF

All residues Cys, Asp, Glu, Gly, His, Lys, Asn, Pro, Gln, Arg, Ser, Thr were changed to Ala at positions 7, 9, 10, 17, 18, 20, 21, 22, 24, 25, 26, 29, 30, 31, 32, 33, 34, 36, 40, 43, 45, 46, 49, 50, 51, 52, 53, 54, 57, 58, 59, 61, 65, 66, 70, 73, 74, 75, 76, 77, 78, 80, 81, 84, 86, 87, 88, 89, 90, 92, 96, 97, 101, 102, 103, 105, 107, 108, 109, 110, 112, 113, 115, 116, 118, 121, 122, 125, 126, 128, 130, 131, 137, 138, 139, 140, 142, 146, 149, 151, 152, 154, 157, 158, 159, 160, 161, 163, 166, 167, 169, 170, 172, 174, 175, 179, 180, and 182; Tyr was changed to Phe at the positions of 13, 19, 28, 55, 104, 120, 129, and 164.

The mutagenesis methods were inverse PCR with paired primers followed by DpnI digestion. The treated product was then transformed into *E. coli* strain ER1038.

3. Selection of SpeI-HF

Selection of SpeI-HF was achieved using by comparing the activity of each mutant in NEB4 with water and pXBA DNA that was previously digested with SacI-HF as substrate, to a glycerol reaction with ExoI and normal pXba. The SacI-HF digested pXBA allowed for greater clarity when testing mutants for activity compared to WT. The glycerol reaction was used to compare star activity results. Several mutants showed high cognate activity with a simultaneous decrease in star activity: E059A, P065A, S108A, N172A, K174A, Q179A, G182A, and Y055F. After comparing purified samples, SpeI(P065A) was designated as SpeI-HF.

4. Purification of SpeI-HF

Two liters of cell ER3081(pRRS-SpeIM7(P065A), pSYX20-SpeIM9)) were grown in LB with 100 µg/ml Amp and 33 µg/ml at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated SpeI-HF was then added an equal volume of glycerol and stored at −20° C.

5. Comparison of SpeI-HF and SpeI-WT

The FIs of SpeI-HF and SpeI-WT have been determined separately on pXba DNA in four NEB buffers with diluent C. and the result is listed in Table 18 (below).

TABLE 18

Comparison of SpeI-HF and SpeI-WT

| Buffer | SpeI-HF Activity | FI | SpeI-WT Activity | FI | Improvement Factor |
|---|---|---|---|---|---|
| NEB1 | 50% | ≥4000 | 100% | 1000 | ≥1000 |
| NEB2 | 12.5% | ≥2000 | 50% | 500 | ≥2 |
| NEB3 | 12.5% | ≥2000 | 12.5% | 2000 | ≥⅛ |
| NEB4 | 100% | ≥8000 | 50% | 500 | ≥2 |

SpeI-HF has most activity in NEB4, where the FI is ≥8000; SpeI-WT has most activity in NEB1, where the FI is 1000. So the overall improvement factor is ≥8.

Example 18: Engineering of HF BsmAI

1. Expression of BsmAI

BsmAI was expressed in *E. coli* transformed with pBAD241-BsmAIR and pACYC-BsmAIM, each contains BsmAI endonuclease and methylase gene. The cells were grown at 37° C. overnight in LB with Amp and Cam and then induced by arabinose for 4 hours.

2. Mutagenesis of BsmAI-HF

Due to the homology among BsaI, BsmBI and BsmAI, amino acids in the region 210-227 of BsmAI were selected to mutate to Ala one at a time because that the high fidelity mutants of BsaI and BsmBI were found in the this similar region.

The mutagenesis methods were inverse PCR with paired primers followed by DpnI digestion. The treated product was then transformed into *E. coli* strain ER3081.

3. Selection of BsmAI-HF

Selection of BsmAI-HF was achieved using comparison of star activity of mutant BsmAI and WT BsmAI in NEB4 on FX174 DNA as substrate. Two mutants had less star activity than the WT BsmAI: N212A and L213A. Mutant BsmAI(N212A) is designated as BsmAI-HF.

4. Purification of BsmAI-HF

Two liters of cell ER2566(pBAD241-BsmAI(N212A), pACYC184-BsmAIM)) were grown in LB with 100 µg/ml Amp and 33 µg/ml Cam at 37° C. for overnight. Then the cells were induced by arabinose with final concentration of 0.2% for 4 hours. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated by Vivaspin® 15R (Vivascience, now Sartorius Vivascience GmbH, Goettingen, Germany). The concentrated BsmAI-HF was then added same volume of glycerol and stored at −20° C.

5. Comparison of BsmAI-HF and BsmAI-WT

The FIs of BsmAI-HF and BsmAI-WT have been determined separately on FX174 DNA in four NEB buffers with diluent B. The result is listed in Table 19 (below).

TABLE 19

Comparison of BsmAI-HF and BsmAI-WT

| Buffer | BsmAI-HF Activity | FI | BsmAI-WT Activity | FI | Improvement Factor |
|---|---|---|---|---|---|
| NEB1 | 100% | ≥4000 | 50% | 120 | ≥32 |
| NEB2 | 50% | ≥2000 | 50% | 500 | ≥4 |
| NEB3 | 12.5% | ≥500 | 50% | 500 | 1 |
| NEB4 | 100% | ≥4000 | 100% | 250 | ≥8 |

BsmAI-HF performed best in NEB1 and NEB4, in which the FI was ≥4000; BsmAI-WT performed best in NEB4, in which the FI was 250. So the overall improvement factor was ≥4000/250=≥16.

Example 19: Engineering of HF BstXI

BstXI recognizes and digests at CCANNNNN/NTGG as described in Example 19 of International Publication No. WO 2009/009797. A mutant BstXI(N65A) was selected as the high fidelity version of the BstXI. A further step to search for better BstXI with less star activity is to mutate N65 to all other amino acid residues. Among those, BstXI(N65T) was found to have less star activity and designated to be BstXI-HF.

The BstXI-HF was expressed in ER2833 (pBAD241-BstXI(N65T), pACYC-BstXIM. The growth and purification methods were performed according to WO/2009/009797.

The following table (Table 20) compares the FIs of BstXI-HF and BstXI WT.

TABLE 20

Comparison of BstXI-HF and BstXI-WT

| Buffer | BstXI-HF Activity | FI | BstXI-WT Activity | FI | Improvement Factor |
|---|---|---|---|---|---|
| NEB1 | 50% | ≥500 | 6% | 4 | ≥125 |
| NEB2 | 100% | ≥1000 | 100% | 32 | ≥32 |
| NEB3 | 100% | ≥1000 | 100% | 2 | ≥500 |
| NEB4 | 100% | ≥1000 | 100% | 32 | ≥32 |

The BstXI-HF had the best activity in NEB2, NEB3 and NEB4, the best FI of BstXI-HF was ≥1000; the WT BstXI had the best activity in NEB2, NEB3 and NEB4. The FI of WT BstXI in NEB2 and NEB4 was 32. So the overall improvement factor was ≥32.

Example 20: Engineering of HF SfiI

1. Expression of SfiI

SfiI was expressed in *E. coli* transformed with pRRS-SfiIR and pSX33-SfiIM, each contains SfiI endonuclease and methylase gene. The cells were grown at 30° C. overnight in LB with Amp and Kan.

2. Mutagenesis of SfiI-HF

All residues Cys, Asp, Glu, Gly, His, Lys, Asn, Pro, Gln, Arg, Ser, Thr were changed to Ala at positions 7, 9, 11, 12, 14, 15, 17, 18, 19, 20, 22, 23, 26, 29, 30, 32, 33, 34, 36, 37, 40, 41, 42, 45, 46, 47, 48, 49, 55, 56, 58, 59, 63, 66, 67, 69, 71, 72, 73, 76, 79, 81, 82, 84, 87, 88, 89, 90, 91, 94, 95, 100, 102, 104, 105, 106, 107, 108, 109, 110, 111, 113, 114, 115, 116, 118, 120, 122, 124, 125, 126, 127, 128, 129, 130, 133, 135, 137, 140, 141, 145, 146, 148, 149, 150, 153, 156, 157, 158, 162, 166, 167, 169, 170, 172, 173, 174, 176, 177, 179, 180, 185, 187, 188, 190, 192, 193, 194, 196, 197, 198, 199, 200, 201, 202, 205, 207, 208, 209, 210, 211, 213, 214, 215, 218, 220, 224, 225, 227, 228, 231, 233, 235, 236, 238, 240, 242, 243, 244, 246, 247, 248, 249, 251, 252, 254, 255, 257, 258, 259, 261, 262, 263; Tyr is changed to Phe at the positions of 31, 60, 68, 80, 164, 165, 175, 182, 195, 222, 239, and 245.

The mutagenesis methods were inverse PCR with paired primers followed by DpnI digestion. The treated product was then transformed into E. coli strain ER2169.

3. Selection of SfiI-HF

Selection of SfiI-HF was achieved using comparison of activity between mutants and WT in water with NEB ExoI buffer and BSA using pXba DNA predigested with EcoRI-HF as substrate. Mutants with similar or greater activity to wild type while also showing a change in star activity in a defined buffer compared to WT were selected. Several mutants are found to have more activity in NEB4: E007A, D011A, E049A, R073A, R0114A, G137A, S210A, and R213A. After purification, P114A proved to have the most significant decrease in star activity. SfiI(R114A) is designated as SfiI-HF.

Also notable were the mutants that increased star activity: N071A, D079A, H162A, R225A, K227A, Y068F, and Y182F. Y068F was previously noted to have different cleavage from WT.

4. Purification of SfiI-HF

Two liters of cell ER2169(pRRS-SfiI(R114A), pSX33-SfiIM)) were grown in LB with 100 µg/ml Amp and 33 µg/ml Kan at 30° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated SfiI-HF was then added an equal volume of glycerol and stored at −20° C.

5. Comparison of SfiI-HF and SfiI-WT

Figure 11:
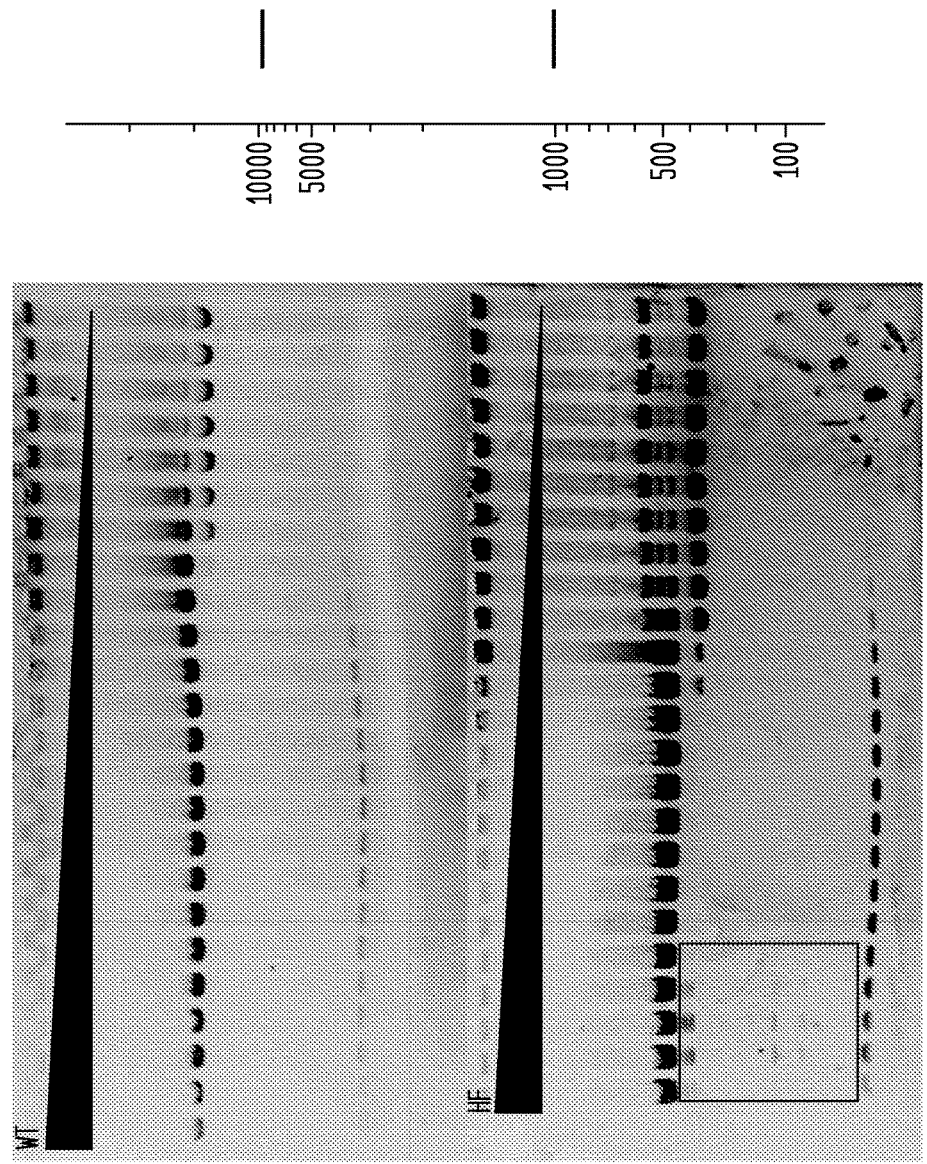
FIG. 11 shows a comparison of SfiI-HF and SfiI-WT on pBC4. The SfiI-HF has an FI of at least 8,000 in NEB4, while the SfiI-WT has an FI of 64, providing an improvement factor of at least 120. The right panel is the theoretical digestion pattern.

The FIs of SfiI-HF and SfiI-WT have been determined separately on pBC4 DNA in four NEB buffers with diluent C. The comparison is shown in FIG. 11, and the result is listed in Table 21 (below).

TABLE 21

Comparison of SfiI-HF and SfiI-HF

| Buffer | SfiI-HF Activity | SfiI-HF FI | SfiI-HF Activity | SfiI-HF FI | Improvement Factor |
|---|---|---|---|---|---|
| NEB1 | 50% | ≥250 | 12.5% | 64 | ≥4 |
| NEB2 | 12.5% | ≥1000 | 100% | 250 | ≥4 |
| NEB3 | 0.4% | ≥32 | 100% | 2000 | ≥1/64 |
| NEB4 | 100% | ≥8000 | 25% | 64 | ≥125 |

SfiI-HF performed best in NEB4, in which the FI was ≥8000; WT SfiI performed best in NEB3, in which the FI was 2000. The overall improvement factor is ≥8000/2000=≥4.

Example 21: Engineering of HF PmeI

1. Expression of PmeI

PmeI was expressed in E. coli transformed with pRRS-PmeIR and pACYC184-EsaS9IM, each contains PmeI endonuclease and methylase gene. The cells were grown at 37° C. overnight in LB with Amp and Cam.

2. Mutagenesis of PmeI-HF

All residues Cys, Asp, Glu, Gly, His, Lys, Asn, Pro, Gln, Arg, Ser, Thr were changed to Ala at positions 7, 8, 10, 13, 14, 17, 20, 21, 22, 25, 28, 29, 30, 32, 33, 35, 37, 39, 41, 42, 43, 46, 47, 49, 50, 51, 54, 55, 60, 62, 63, 64, 66, 67, 68, 69, 71, 72, 73, 77, 79, 80, 81, 82, 83, 86, 87, 91, 94, 95, 96, 97, 98, 100, 104, 106, 107, 108, 109, 110, 112, 113, 114, 115, 116, 117, 118, 121, 123, 124, 127, 130, 131, 132, 133, 134, 135, 137, 138, 145, 147, 148, 149, 151, 152, 153, 154, 155, 157, 160, 162, 165, 166, 167, 169, 170, 171, 172, 177, 180, 181, 182, 183, 185, 186, 188, 190, 191, 192, 193, 194, 199, 200, 201, 202, 204, 207, 208, 209, 210, 211, 212, 215, 218, 219, 221, 222, 223, 225; Tyr is changed to Phe at the positions of 111, 129, 146, and 161.

The mutagenesis methods were inverse PCR with paired primers followed by DpnI digestion. The treated product was then transformed into E. coli strain ER2426.

3. Selection of PmeI-HF

Selection of PmeI-HF was achieved using comparison of activity between WT and mutants in water NEB4 using lambda DNA as substrate with the same mutants in glycerol with NEB Thermopol buffer and pXba as a substrate. The testing of mutants and WT PmeI in water on lambda DNA allowed for a reference of cognate activity, and with similar or more activity than WT in NEB4 were selected. Mutants with acceptable activity were then rejected if they showed no change in star activity when tested under glycerol conditions with Thermopol buffer and pXba. Several mutants were shown to have differences in star activity: P079A, E086A, H096A, and E218A. PmeI(E086A) is designated as PmeI-HF.

4. Purification of PmeI-HF

Two liters of cell ER2426(pRRS-PmeI(P154A), pACYC184-EsaS9IM)) were grown in LB with 100 µg/ml Amp and 33 µg/ml Cam at 37° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated PmeI-HF was then added an equal volume of glycerol and stored at −20° C.

5. Comparison of PmeI-HF and PmeI-WT

The FIs of PmeI-HF and PmeI-WT have been determined separately on pXba DNA in four NEB buffers with diluent A. The result is listed in Table 22 (below).

TABLE 22

Comparison of PmeI-HF and PmeI-WT

| Buffer | PmeI-HF Activity | PmeI-HF FI | PmeI-WT Activity | PmeI-WT FI | Improvement Factor |
|---|---|---|---|---|---|
| NEB1 | 12.5% | ≥2000 | 100% | 250 | ≥64 |
| NEB2 | 6.3% | ≥500 | 100% | 250 | ≥500 |
| NEB3 | 0.4% | ≥32 | 50% | 120 | ≥125 |
| NEB4 | 100% | ≥8000 | 25% | 64 | ≥500 |

PmeI-HF performed best in NEB4, in which the FI was ≥8000; PmeI-WT performed best in NEB1 and NEB2, in which the FI was 250. The overall improvement factor is ≥8000/250=≥16.

Example 22: Engineering of HF SmaI

1. Expression of SmaI

SmaI was expressed in *E. coli* transformed with pRRS-SmaIR and pSYX20-SmaIM, each contains SmaI endonuclease and methylase gene. The cells were grown at 37° C. overnight in LB with Amp and Kan.

2. Mutagenesis of SmaI-HF

All residues Cys, Asp, Glu, Gly, His, Lys, Asn, Pro, Gln, Arg, Ser, Thr were changed to Ala; all Tyr were changed to Phe.

The mutagenesis methods were inverse PCR with paired primers followed by DpnI digestion. The treated product was then transformed into *E. coli* strain ER2428.

3. Selection of SmaI-HF

Selection of SmaI-HF was achieved using comparison of activity in water NEB4 using pXba DNA as substrate with a star-activity producing glycerol condition with NEB Standard Taq buffer. Mutants which showed changes in star activity in the designated buffer while retaining similar or high cognate activity to WT were selected. Several mutants were found: E32R, S081A, G132A and a double-mutant F60L/S61R. SmaI(F60L/S61R) is designated as SmaI-HF.

4. Purification of SmaI-HF

Two liters of cell ER2428(pRRS-SmaI(F60L/S61R), pSYX20-SmaIM)) were grown in LB with 100 µg/ml Amp and 33 µg/ml Kan at 37° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated SmaI-HF was then added an equal volume of glycerol and stored at −20° C.

5. Comparison of SmaI-HF and SmaI-WT

Figure 12:
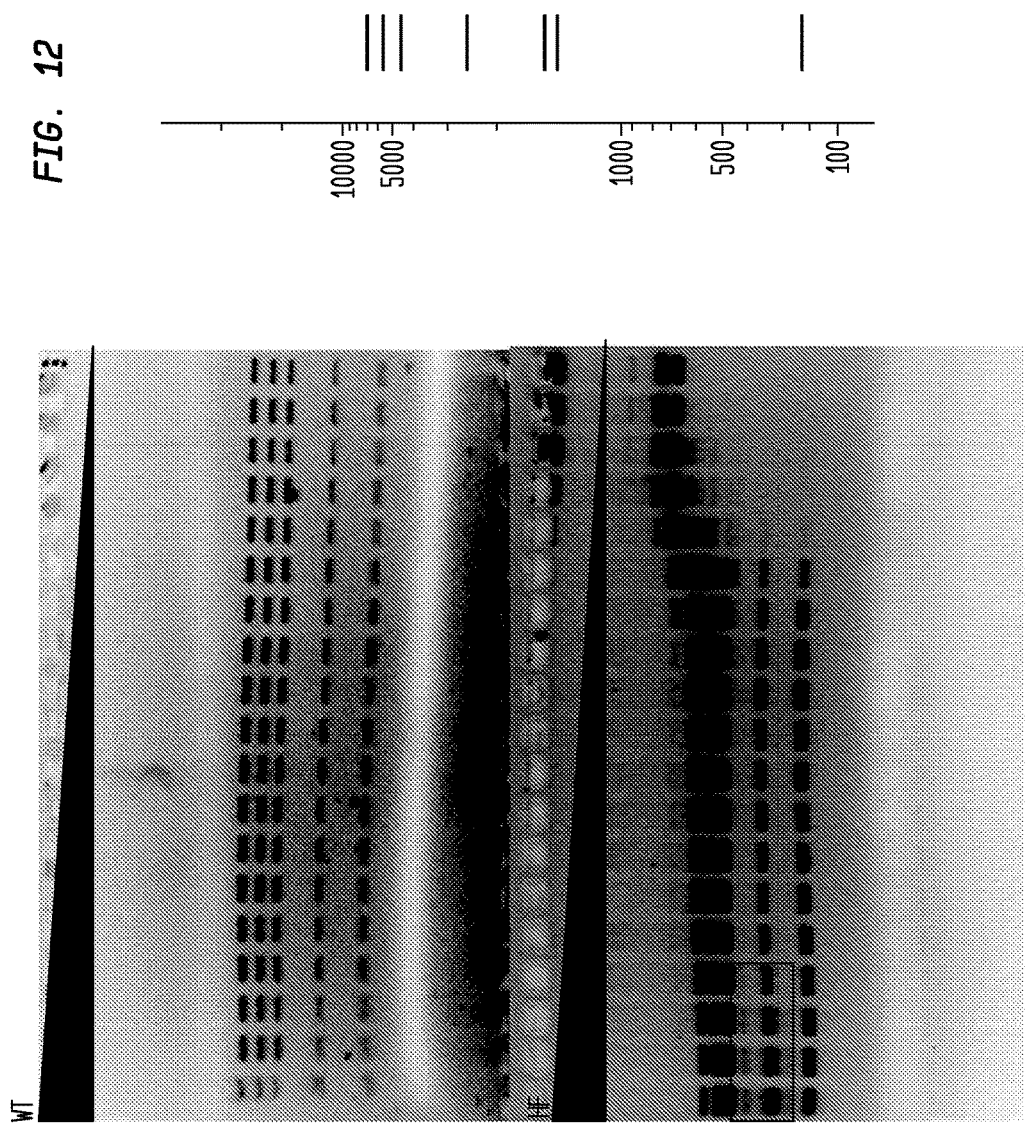
FIG. 12 shows a comparison of SmaI-HF and SmaI-WT on pXba. The SmaI-HF has an FI of at least 256,000, while the SmaI-WT has an FI of 64, providing an improvement factor of at least 4,000. The right panel is the theoretical digestion pattern.

The FIs of SmaI-HF and WT SmaI have been determined separately on pXba DNA in four NEB buffers with diluent A. The comparison is shown in FIG. 12, and the result is listed in Table 23 (below).

TABLE 23

Comparison of SmaI-HF and SmaI-WT

| Buffer | SmaI-HF Activity | SmaI-HF FI | SmaI-WT Activity | SmaI-WT FI | Improvement Factor |
|---|---|---|---|---|---|
| NEB1 | 0.2% | ≥2000 | 3% | ≥16 | ND |
| NEB2 | 3.2% | ≥32000 | 12.5% | ≥64 | ND |
| NEB3 | 0.0032% | ≥32 | 0.8% | ≥8 | ND |
| NEB4 | 100% | ≥256000 | 100% | 64 | ≥4000 |

ND: Not determinable

SmaI-HF performed best in NEB4, in which the FI was ≥256000; SmaI-WT performed best in NEB2 and NEB4, in which the FI was 64. The overall improvement factor is ≥256000/64=≥4000.

Example 23: Engineering of High Fidelity AatII

1. Expression of AatII

AatII was expressed in *E. coli* transformed with pRRS-AatIIR and pACYC184-AatIIM, each contains AatII endonuclease and methylase gene. The cells were grown at 37° C. overnight in LB with Amp and Cam.

2. Mutagenesis of AatII-HF

All residues Cys, Asp, Glu, Gly, His, Lys, Asn, Pro, Gln, Arg, Ser, Thr were changed to Ala at positions 8, 9, 11, 12, 13, 16, 17, 18, 20, 22, 26, 29, 32, 33, 35, 36, 37, 38, 40, 43, 45, 46, 49, 52, 53, 54, 56, 57, 58, 60, 61, 62, 64, 65, 69, 70, 71, 72, 73, 74, 75, 77, 79, 80, 83, 84, 86, 87, 90, 92, 93, 94, 95, 97, 99, 100, 103, 104, 106, 107, 111, 113, 114, 117, 121, 123, 124, 125, 126, 128, 129, 131, 132, 133, 135, 136, 140, 141, 143, 144, 145, 146, 148, 149, 150, 151, 153, 155, 156, 157, 160, 164, 165, 167, 169, 171, 172, 173, 174, 175, 176, 177, 179, 181, 182, 186, 189, 191, 192, 193, 194, 196, 198, 200, 201, 203, 204, 205, 206, 207, 208, 210, 211, 213, 214, 216, 217, 219, 220, 221, 222, 226, 228, 230, 231, 233, 235, 236, 237, 238, 240, 241, 244, 247, 248, 249, 250, 251, 252, 253, 256, 262, 264, 265, 266, 268, 269, 272, 273, 275, 280, 281, 282, 283, 286, 298, 292, 293, 295, 296, 297, 298, 301, 302, 308, 309, 311, 312, 313, 314, 315, 317, 319, 321, 325, 327, 329, 330, 333, 334, 335, 336; Tyr was changed to Phe at the positions of 82, 89, 98, 112, 232, 305, and 306.

The mutagenesis methods were inverse PCR with paired primers followed by DpnI digestion. The treated product was then transformed into *E. coli* strain ER2426.

3. Selection of AatII-HF

Selection of AatII-HF was achieved using comparison of activity in NEB4 in water to NEB ExoI buffer in glycerol using pXba DNA as substrate. Mutants which showed changes in star activity under the glycerol conditions were chosen for further testing as long as they had similar or greater activity than WT under normal conditions in water. Several mutants were chosen for further testing after the initial screen: G013A, G016A, K018A, P052A, R053A, K070A, E071A, D072A, G073A, S84A, E086A, R090A, K094A, R095A, P099A, P103A, K113A, N135A, S151A, P157A, G173A, T204A, S206A, K207A, E233A, N235A, E237A, S238A, D241A, K295A, S301A, and S302A. AatII (N235A) is designated as AatII-HF.

4. Purification of AatII-HF

Two liters of cell ER2426(pRRS-AatII(N235A), pACYC184-AatIIM)) were grown in LB with 100 µg/ml Amp and 33 µg/ml Cam at 37° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™

Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated AatII-HF was then added an equal volume of glycerol and stored at −20° C.

5. Comparison of AatII-HF and AatII-WT

The FIs of AatII-HF and WT AatII have been determined separately on pBR322 DNA in four NEB buffers with diluent A. The result is listed in Table 24 (below).

TABLE 24

Comparison of AatII-HF and AatII-WT

| Buffer | AatII-HF Activity | AatII-HF FI | AatII-WT Activity | AatII-WT FI | Improvement Factor |
|---|---|---|---|---|---|
| NEB1 | NC | NC | 3% | 32 | ND |
| NEB2 | NC | NC | 100% | ¼ | ND |
| NEB3 | NC | NC | NC | NC | ND |
| NEB4 | 100% | ≥1000 | 50% | 16 | ≥64 |

NC: Not completable;
ND: Not determinable

AatII-HF performed best in NEB4, in which the FI was ≥1000; WT AatII performed best in NEB2, in which the FI was ¼. The overall improvement factor is ≥1000/¼=≥4000.

Example 24: Engineering of HF ApoI

1. Expression of ApoI

ApoI was expressed in *E. coli* transformed with pRRS-ApoIR and pACYC184-ApoIM, each contains ApoI endonuclease and methylase gene. The cells were grown at 37° C. overnight in LB with Amp and Cam.

2. Mutagenesis of ApoI-HF

All residues Cys, Asp, Glu, Gly, His, Lys, Asn, Pro, Gln, and Arg, were changed to Ala at positions 8, 9, 10, 11, 13, 14, 17, 18, 19, 20, 21, 22, 23, 24, 26, 28, 29, 33, 35, 36, 37, 39, 41, 43, 47, 48, 49, 50, 51, 56, 57, 60, 62, 63, 64, 66, 67, 69, 71, 72, 73, 75, 76, 77, 80, 81, 82, 83, 84, 87, 92, 93, 94, 95, 96, 97, 102, 103, 105, 106, 107, 108, 109, 110, 111, 113, 115, 116, 117, 119, 120, 121, 124, 125, 128, 129, 131, 132, 133, 136, 137, 143, 144, 145, 148, 153, 155, 157, 159, 160, 161, 162, 163, 166, 167, 169, 170, 175, 176, 178, 179, 181, 184, 185, 186, 187, 188, 189, 192, 193, 194, 195, 199, 201, 202, 204, 206, 207, 209, 210, 214, 216, 217, 218, 221, 226, 227, 229, and 230.

The mutagenesis methods were inverse PCR with paired primers followed by DpnI digestion. The treated product was then transformed into *E. coli* strain ER2426.

3. Selection of ApoI-HF

Selection of ApoI-HF was achieved using comparison of activity in NEB3 and NEB4 using lambda DNA as substrate. Mutants with more activity than WT in NEB4 were selected as increased activity in NEB4 is an indicator of improved fidelity. The following mutants are found to have more activity in NEB4: S64A, S80A, S162A, T77A/T96A and N178A. ApoI(T77A/T96A) is designated as ApoI-HF.

4. Purification of ApoI-HF

Two liters of cell ER2426(pRRS-ApoI(T77A/T96A), pACYC184-ApoIM)) were grown in LB with 100 μg/ml Amp and 33 μg/ml Cam at 37° C. overnight, induced with 0.5 mM ITPG after 8 hours of growth. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated ApoI-HF was then added an equal volume of glycerol and stored at −20° C.

5. Comparison of ApoI-HF and ApoI-WT

The FIs of ApoI-HF and ApoI-WT have been determined separately on pXba DNA in four NEB buffers with diluent A. The result is listed in Table 24 (below).

TABLE 24

Comparison of ApoI-HF and ApoI-WT

| Buffer | ApoI-HF Activity | ApoI-HF FI | ApoI-WT Activity | ApoI-WT FI | Improvement Factor |
|---|---|---|---|---|---|
| NEB1 | 50% | ≥2000 | 25% | 120 | ≥16 |
| NEB2 | 100% | ≥4000 | 100% | 32 | ≥125 |
| NEB3 | 25% | ≥1000 | 100% | 64 | ≥16 |
| NEB4 | 50% | ≥2000 | 50% | 32 | ≥64 |

ApoI-HF performed best in NEB2, in which the FI was ≥4000; WT ApoI performed best in NEB2 and NEB3, in which the best FI was 64. The overall improvement factor is ≥4000/64=≥64.

Example 25: Engineering of High Fidelity BsmBI

Figure 13:
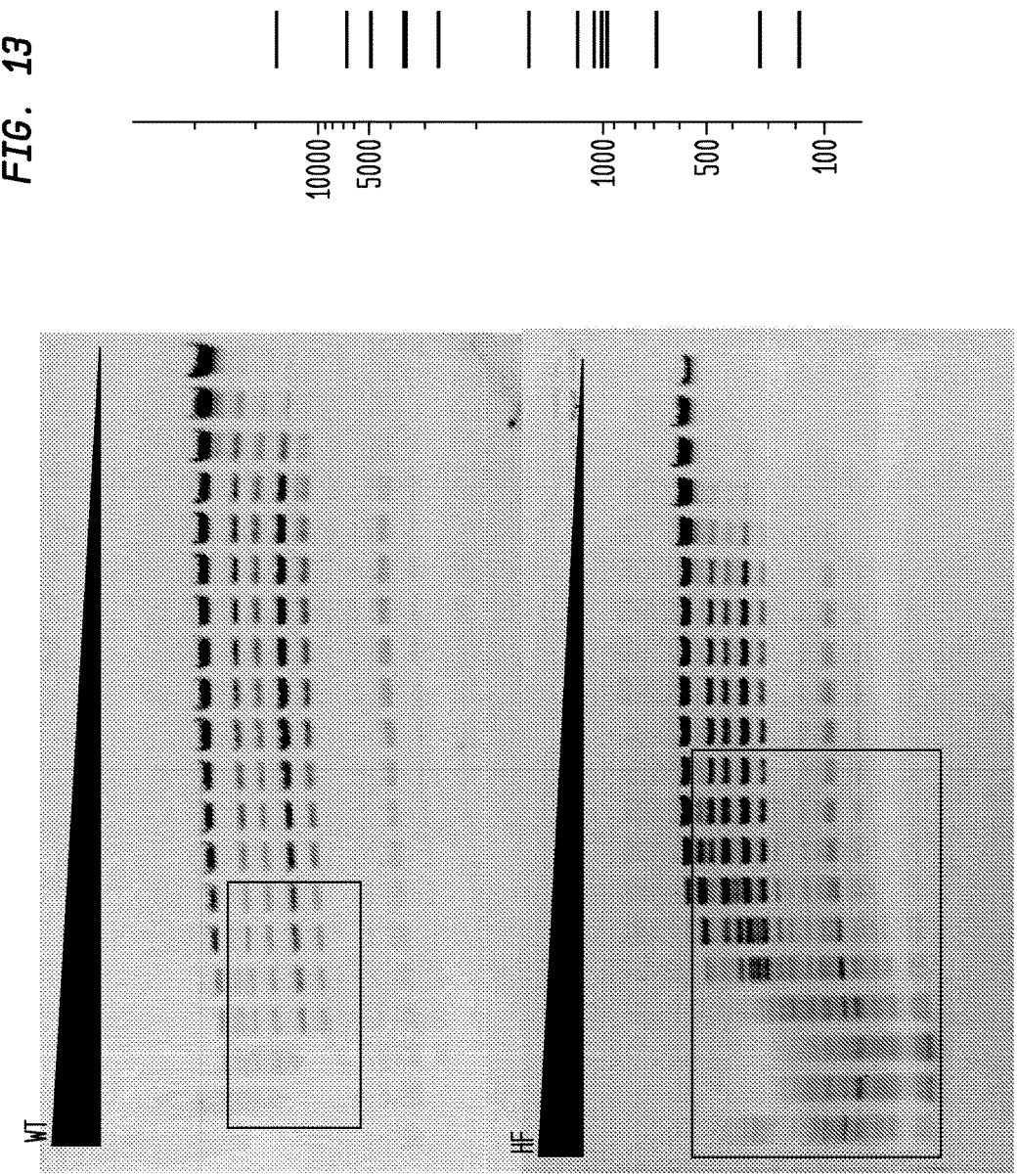
FIG. 13 shows a comparison of BsmBI-HF and BsmBI-WT on lambda DNA. The BsmBI-HF has an FI of 250 in NEB4, while the BsmBI-WT has an FI of 4, providing an improvement factor of at least 64. The right panel is the theoretical digestion pattern.

BsmBI recognizes and digests at CGTCTCN1/N5 as described in Example 23 of International Publication No. WO 2009/009797. A mutant BsmBI(R232A) was selected as the high fidelity version of the BsmBI. Further characterization of this mutant revealed that though the performance of BsmBI(R232A) on one hour scale is excellent, it did not perform well in the overnight digestion. While searching for more mutants, BsmBI(W238A) was found to be excellent in both one hour and overnight reaction, and designated to be BsmBI-HF (FIG. 13).

The BsmBI-HF was expressed in ER3081 (pBAD241-BsmBIR(W238A)/pACYC-BsmAIM). The growth and purification methods were performed according to WO/2009/009797.

The following table (Table 26) compares the FIs of BsmBI-HF and BsmBI-WT.

TABLE 26

Comparison of BsmBI-HF and BsmBI-WT

| Buffer | BsmBI-HF | | BsmBI-WT | | Improvement Factor |
|---|---|---|---|---|---|
| | Activity | FI | Activity | FI | |
| NEB1 | 50% | 32 | 12.5% | 1 | 32 |
| NEB2 | 50% | 120 | 50% | 8 | 25 |
| NEB3 | 12.5% | 250 | 100% | 120 | 2 |
| NEB4 | 100% | 250 | 25% | 4 | 64 |

The BsmBI-HF had the best activity in NEB4, the FI of BsmBI-HF in NEB4 was 250; the BsmBI-WT had the best activity in NEB3. The FI of WT BsmBI in NEB2 was 120. So the overall improvement factor was 2.

Example 26: Engineering of HF BmtI

1. Expression of BmtI
BmtI was expressed in *E. coli* transformed with pACYC-BmtIM and placzz1-BmtIR. pACYC is a low copy compatible plasmid. The cells were grown at 37° C. overnight in LB with Amp and Cam.

2. Mutagenesis of BmtI-HF
The point mutagenesis of the selected mutations was done by inverse PCR. 150 amino acid mutations were made in BmtI as follows. Cys, Asp, Glu, Phe, His, Lys, Met, Asn, Gin, Arg, Ser, Thr, Trp were mutated to Ala. Try was mutated to Phe. These were: 5, 9, 11, 12, 16, 19, 20, 23, 24, 25, 26, 27, 30, 32, 33, 34, 35, 36, 39, 45, 46, 49, 50, 51, 53, 56, 58, 59, 60, 63, 65, 69, 71, 72, 73, 74, 75, 76, 78, 79, 80, 81, 83, 85, 86, 88, 89, 90, 92, 93, 94, 95, 97, 98, 99, 101, 104, 105, 106, 108, 110, 111, 112, 113, 116, 118, 119, 120, 121, 122, 124, 128, 129, 131, 132, 133, 134, 136, 138, 139, 140, 141, 142, 144, 145, 146, 147, 148, 150, 151, 152, 154, 156, 157, 161, 162, 163, 165, 166, 167, 168, 169, 171, 172, 173, 175, 178, 179, 180, 181, 185, 186, 189, 190, 191, 193, 194, 195, 196, 199, 200, 201, 202, 203, 204, 205, 206, 207, 208, 210, 211, 213, 214, 216, 217, 218, 219, 220, 221, 222, 226, 228, 229, 230, 231, 234, 236, 237, 238, 239 and 241. The mutagenesis methods were inverse PCR with paired primers followed by DpnI digestion. The treated product was then transformed into *E. coli* strain 3081.

3. Selection of BmtI-HF
Four colonies of each mutation were grown up in LB with Amp and Cam at 37° C. overnight. The standard cognate and star activity assays of BmtI were performed using pBC4 in ExoI buffer and 10% DMSO.

The mutants S50A, Y81F, N93A and W207A were picked out in screening assays. After several rounds of comparison in different conditions and substrates, S50A was found to be the preferred mutant, retaining high canonical enzyme activity, but displaying substantially reduced star activity. BmtI (S50A) was labeled as BmtI-HF.

4. Purification of BmtI-HF
Two liters of cell *E. coli* 3081 (placzz1-BmtIR(S50A), pACYC-BmtIM) were grown in LB with 100 µg/ml Amp and 30 µg/ml Cam at 37° C. for overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated. The concentrated BmtI-HF was then added same volume of glycerol and stored at −20° C.

5. Comparison of BmtI-HF and BmtI-WT
BmtI-HF was 2-fold serial diluted with A and reacted on pXba. The result is shown in Table 27.

TABLE 27

Comparison of BmtI-HF and BmtI-WT

| Buffer | BmtI-HF | | BmtI-WT | | Improvement Factor |
|---|---|---|---|---|---|
| | Activity | FI | Activity | FI | |
| NEB1 | 25% | ≥256000 | 50% | 32 | ≥8000 |
| NEB2 | 25% | ≥256000 | 100% | 16 | ≥16000 |
| NEB3 | 0.2% | ≥2000 | 6.3% | 32 | ≥64 |
| NEB4 | 100% | ≥1000000 | 100% | 16 | ≥62500 |

BmtI-HF performed best in NEB4, in which the preferred FI was ≥1000000; BmtI-WT performed best in NEB2 and NEB4, where the FI was 16. The overall FI improvement factor was ≥1000000/16=≥62500

Example 27: Engineering of HF BstNI

1. Expression of BstNI
BstNI was expressed in *E. coli* transformed with pBAD241-BstNIR and pACYC184-BstNIM, each contains BstNI endonuclease and methylase gene. The cells were grown at 37° C. overnight in LB with Amp and Cam, diluted to 1/10 with LB and then induced by arabinose for 4 hours.

2. Mutagenesis and Selection of BstNI-HF
During the experiment of creating a series mutations of BstNI, BstNI(G26N) was found to have less star activity than the WT BstNI. To searching for better BstNI mutants with even less star activity, G26 was mutated to all other amino acids. Among all these mutants, BstNI(G26T) has the least star activity and is designated as BstNI-HF.

3. Purification of BstNI-HF
Two liters of cell ER2833(pBAD241-BstNI(G26T), pACYC184-BstNIM) were grown in LB with 100 µg/ml Amp and 33 µg/ml Cam at 37° C. for overnight. Then the cells were diluted 1 to 10 with LB and then induced by arabinose with final concentration of 0.2% for 4 hours. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions are then test for activity. The fractions with highest activity were further concentrated by Vivaspin® 15R (Vivascience, now Sartorius Vivascience GmbH, Goettingen, Germany). The concentrated BstNI-HF was then added same volume of glycerol and stored at −20° C.

Figure 14:
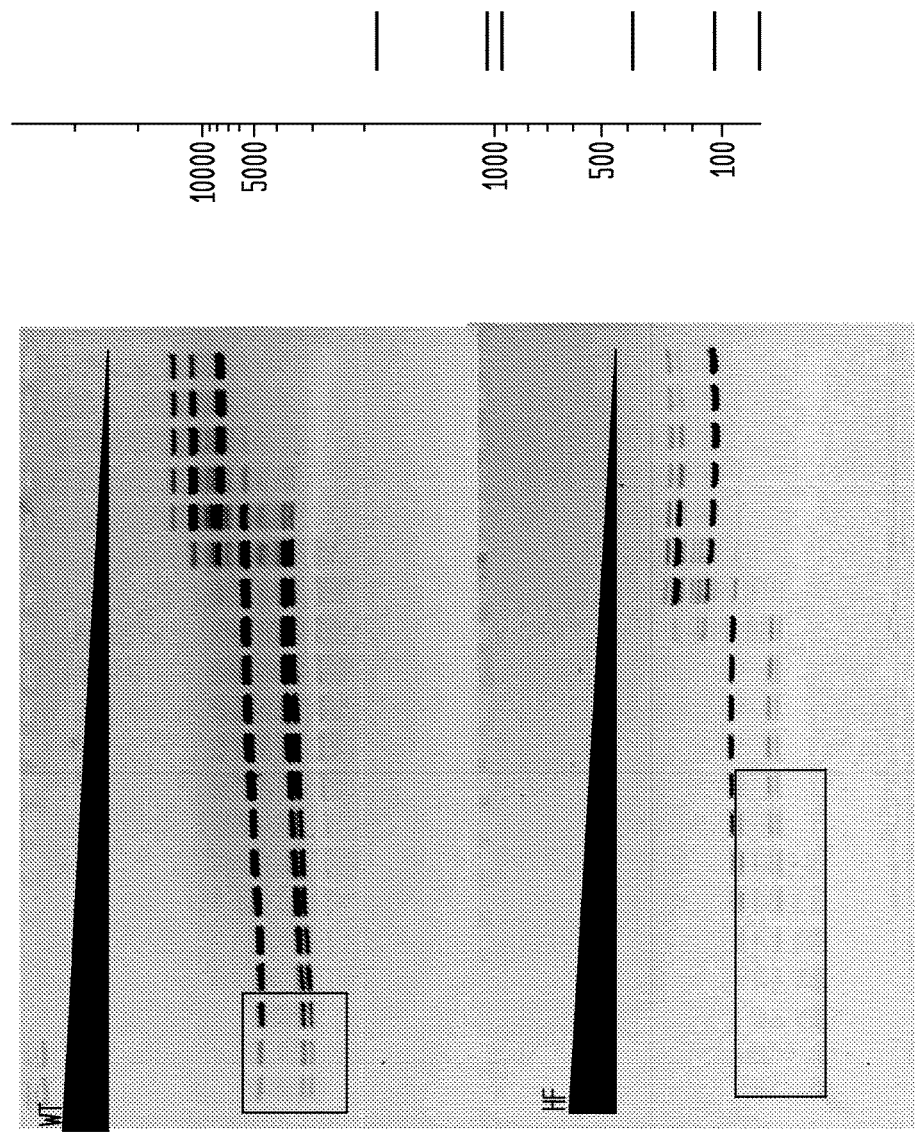
FIG. 14 shows a comparison of BstNI-HF and BstNI-WT on pBR322. The BstNI-HF has an FI of 500 in NEB4, while the BstNI-WT has an FI of 4, providing an improvement factor of at least 120. The right panel is the theoretical digestion pattern.

4. Comparison of BstNI-HF and WT BstNI
The FIs of BstNI-HF and WT BstNI have been determined separately on pBR322 DNA in four NEB buffers with diluent A. The comparison is shown in FIG. 14, and the result is listed in Table 28 (below).

TABLE 28

Comparison of BstNI-HF and BstNI-WT

| Buffer | BstNI-HF Activity | BstNI-HF FI | BstNI-WT Activity | BstNI-WT FI | Improvement Factor |
|---|---|---|---|---|---|
| NEB1 | 50% | ≥120 | 50% | 8 | ≥16 |
| NEB2 | 100% | ≥500 | 100% | 64 | 8 |
| NEB3 | 25% | ≥120 | 100% | 250 | ≥1/8 |
| NEB4 | 100% | 500 | 50% | 4 | ≥32 |

BstNI-HF performed best in NEB2 and NEB4, in which the best FI was ≥500; BstNI-WT performed best in NEB2 and NEB3, in which the best FI was 250. So the overall improvement factor was ≥500/250=≥2.

Example 28: Engineering of HF MluI

1. Expression of MluI

MluI was expressed in *E. coli* transformed with pUC19-MluIR and pACYC184-MluIM, each contains MluI endonuclease and methylase gene. The cells were grown at 30° C. overnight in LB with Amp and Cam.

2. Mutagenesis of MluI-HF

All residues Cys, Asp, Glu, Gly, His, Lys, Asn, Pro, Gin, Arg, Ser, Thr were changed to Ala at positions 7, 8, 10, 11, 13, 16, 21, 23, 24, 26, 27, 30, 31, 33, 34, 35, 36, 37, 39, 42, 44, 48, 50, 51, 54, 57, 59, 60, 61, 67, 68, 71, 72, 74, 75, 78, 79, 81, 83, 84, 85, 86, 89, 90, 93, 94, 95, 97, 99, 101, 102, 104, 106, 108, 111, 112, 114, 116, 117, 119, 120, 121, 123, 125, 128, 130, 131, 132, 134, 136, 137, 139, 140, 141, 142, 144, 145, 146, 148, 152, 154, 155, 156, 157, 159, 161, 163, 165, 166, 170, 172, 173, 174, 176, 177, 179, 180, 181, 182, 183, 184, 186, 189, 192, 195, 196, 197, 200, 206, 207, 208, 210, 211, 214, 216, 218, 219, 220, 221, 223, 227, 228, 230, 232, 233, 234, 236, 237, 238, 240, 243, 244, 247, 249, 255, 256, 257, 258, 261, 263, 264, 265, 266, 269; Tyr was changed to Phe at the positions of 14, 28, 47, 53, 77, 107, 175, 198, 217, 239, and 248.

The mutagenesis methods were inverse PCR with paired primers followed by DpnI digestion. The treated product was then transformed into *E. coli* strain ER1582.

3. Selection of MluI-HF

Selection of MluI-HF was achieved using comparison of activity in NEB3 and NEB4 using lambda DNA as substrate. Mutants with more activity than WT in NEB4 were selected as increased activity in NEB4 is an indicator of improved fidelity. The only mutant found to fit our criteria was E112A/R132A; MluI(E112A/R132A) is designated as MluI-HF.

4. Purification of MluI-HF

Two liters of cell ER1582(pUC19-MluI(E112A/R132A), pACYC184-MluIM)) were grown in LB with 100 µg/ml Amp and 33 µg/ml Cam at 30° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated MluI-HF was then added an equal volume of glycerol and stored at −20° C.

5. Comparison of MluI-HF and MluI-WT

The FIs of MluI-HF and WT MluI have been determined separately on lambda DNA in four NEB buffers with diluent A. The comparison is shown in FIG. 15, and the result is listed in Table 29 (below).

TABLE 29

Comparison of MluI-HF and MluI-WT

| Buffer | MluI-HF Activity | MluI-HF FI | MluI-WT Activity | MluI-WT FI | Improvement Factor |
|---|---|---|---|---|---|
| NEB1 | 50% | ≥16000 | 25% | 500 | ≥32 |
| NEB2 | 100% | ≥32000 | 6.3% | 16 | ≥200 |
| NEB3 | 6.3% | ≥2000 | 100% | 2000 | ≥1 |
| NEB4 | 100% | ≥32000 | 25% | 32 | ≥1000 |

MluI-HF performed best in NEB2 and NEB4, in which the FI was ≥32000; MluI-WT performed best in NEB3, in which the FI was 2000. The overall improvement factor is ≥32000/2000=≥16.

Example 29: Engineering of HF BanI

1. Expression of BanI

BanI was expressed in *E. coli* transformed with pUC19-BanIR and pACYC184-BanIM, each contains BanI endonuclease and methylase gene. The cells were grown at 37° C. overnight in LB with Amp and Cam.

2. Mutagenesis of BanI-HF

All residues Cys, Asp, Glu, Gly, His, Lys, Asn, Pro, Gin, Arg, Ser, Thr were changed to Ala at positions 7, 8, 9, 11, 12, 14, 15, 16, 19, 22, 23, 27, 28, 29, 30, 31, 32, 33, 36, 37, 40, 41, 42, 43, 47, 50, 52, 53, 54, 55, 56, 58, 61, 64, 66, 67, 69, 70, 71, 75, 76, 81, 82, 84, 85, 86, 87, 89, 90, 92, 93, 94, 96, 97, 100, 103, 105, 106, 107, 109, 110, 111, 112, 114, 115, 117, 121, 122, 123, 124, 126, 130, 131, 133, 135, 136, 138, 139, 140, 141, 143, 145, 146, 148, 150, 151, 152, 154, 156, 157, 160, 161, 169, 171, 174, 175, 176, 178, 179, 182, 183, 185, 187, 188, 191, 192, 193, 194, 195, 197, 198, 201, 202, 203, 208, 209, 211, 212, 213, 215, 217, 218, 220, 221, 224, 225, 226, 229, 232, 233, 234, 236, 237, 238, 240, 242, 243, 244, 245, 246, 248, 249, 251, 252, 253, 254, 255, 256, 257, 259, 260, 262, 266, 267, 268, 269, 270, 271, 275, 277, 279, 281, 282, 283, 284, 285, 287, 288, 289, 291, 292, 294, 296, 298, 301, 302, 303, 304, 305, 312, 313, 315, 316, 318, 319, 320, 321, 324, 325, 328, 329, 330, 331, 333, 337, 338, 339, 340, 342, 346; Tyr was changed to Phe at the positions of 104, 125, 127, 156, 159, 204, 239, 297, 306, and 336.

The mutagenesis methods were inverse PCR with paired primers followed by DpnI digestion. The treated product was then transformed into *E. coli* strain ER2683.

3. Selection of BanI-HF

Selection of BanI-HF was achieved using comparison of activity in water and NEB4 versus glycerol and NEB ExoI buffer using lambda DNA as substrate. Mutants with as much or more activity than WT in NEB4 were selected if they also showed a change in star activity when tested under glycerol conditions. Another indicator used in selecting these mutants was the fact that removing star activity creates a slow site in cognate cleavage. Numerous mutants were found to have changes in star activity and the resulting slow site: N016A, S33A, P36A, H76A, P87A, N89A, R90A, T138A, K141A, K143A, Q221A, Q224A, N253A, Q292A, R296A, T152I, G326A, and T324A. BanI(Q292A) is designated as BanI-HF.

4. Purification of BanI-HF

Two liters of cell ER2683(pUC19-BanI(P154A), pACYC184-BanIM)) were grown in LB with 100 µg/ml Amp and 33 µg/ml Cam at 37° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BanI-HF was then added an equal volume of glycerol and stored at −20° C.

5. Comparison of BanI-HF and BanI-WT

The FIs of BanI-HF and WT BanI have been determined separately on lambda DNA in four NEB buffers with diluent A. The result is listed in Table 30 (below).

TABLE 30

Comparison of BanI-HF and BanI-WT

| Buffer | BanI-HF Activity | BanI-HF FI | BanI-WT Activity | BanI-WT FI | Improvement Factor |
|---|---|---|---|---|---|
| NEB1 | 50% | ≥1000 | 25% | 4 | ≥250 |
| NEB2 | 12.5% | ≥250 | 25% | 4 | ≥63 |
| NEB3 | 0.4% | ≥8 | 6.3% | 2 | ≥4 |
| NEB4 | 100% | ≥2000 | 100% | 16 | ≥125 |

BanI-HF performed best in NEB4, in which the FI was ≥2000; WT BanI also performed best in NEB4, but the FI was only 16. The overall improvement factor is ≥2000/16=≥125.

Example 30: Engineering of HF KasI

1. Expression of KasI

KasI was expressed in E. coli transformed with placZZ-KasIR and pACY-SfoIM, each contains KasI endonuclease and methylase gene. The cells were grown at 30° C. overnight in LB with Amp and Cam.

2. Mutagenesis of KasI-HF

All residues Cys, Asp, Glu, Gly, His, Lys, Asn, Pro, Gln, Arg, Ser, Thr were changed to Ala at positions 7, 8, 9, 11, 13, 14, 17, 18, 21, 24, 26, 28, 29, 31, 32, 33, 34, 36, 37, 39, 42, 43, 44, 47, 48, 51, 52, 54, 55, 56, 58, 60, 62, 63, 64, 65, 66, 69, 70, 73, 76, 77, 78, 79, 83, 85, 86, 88, 89, 90, 91, 92, 93, 94, 98, 100, 101, 102, 103, 104, 108, 110, 111, 114, 115, 116, 117, 118, 119, 122, 123, 124, 125, 126, 128, 129, 134, 137, 138, 139, 140, 142, 143, 144, 145, 146, 149, 150, 152, 153, 154, 156, 158, 161, 162, 163, 164, 165, 167, 168, 173, 177, 178, 180, 181, 182, 184, 185, 188, 189, 190, 191, 192, 195, 197, 198, 200, 202, 203, 204, 210, 211, 212, 214, 215, 216, 217, 218, 219, 220, 221, 222, 223, 225, 226, 228, 229, 231, 234, 237, 238, 241, 243, 244, 245, 246, 248, 251, 253, 255, 257, 258, 259, 260, 261, 263, 264, 265, 266, 269, 270, 271, 274, 275, 276, 277, and 278; Tyr was changed to Phe at the positions of 19, 41, 74, 80, 95, 207, and 256.

The mutagenesis methods were inverse PCR with paired primers followed by DpnI digestion. The treated product was then transformed into E. coli strain ER2683.

3. Selection of KasI-HF

Selection of KasI-HF was achieved using comparison of activity in NEB3 and NEB4 using pBR322 DNA as substrate. Mutants with more activity than WT in NEB4 were selected as increased activity in NEB4 is an indicator of improved fidelity. The following mutants were found to have more activity in NEB4: K024A, P214A, E146A, N251A and Y095F. KasI(N251A) is designated as KasI-HF.

4. Purification of KasI-HF

Two liters of cell ER2683(pLacZZ-KasI(M251A), pACYC-SfoIM)) were grown in LB with 100 µg/ml Amp and 33 µg/ml Cam at 30° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated KasI-HF was then added an equal volume of glycerol and stored at −20° C.

5. Comparison of KasI-HF and KasI-WT

The FIs of KasI-HF and KasI-WT have been determined separately on pBR322 DNA in four NEB buffers with diluent B. The result is listed in Table 31 (below).

TABLE 31

Comparison of KasI-HF and KasI-WT

| Buffer | KasI-HF Activity | KasI-HF FI | KasI-WT Activity | KasI-WT FI | Improvement Factor |
|---|---|---|---|---|---|
| NEB1 | 50% | ≥8000 | 100% | 1 | ≥8000 |
| NEB2 | 100% | ≥16000 | 100% | 8 | ≥2000 |
| NEB3 | 12.5% | ≥2000 | 100% | 8 | ≥250 |
| NEB4 | 100% | ≥16000 | 100% | 4 | ≥4000 |

KasI-HF performed best in NEB2 and NEB4, in which the FI is ≥16000; KasI-WT performed same in all buffers, in which the best FI is 8. The overall improvement factor is ≥16000/8=≥2000.

Example 31: Engineering of HF NruI

1. Expression of NruI

NruI was expressed in E. coli transformed with pUC19-NruIR and pACYC-Sbo13IM, each contains NruI endonuclease and methylase gene. The cells were grown at 37° C. overnight in LB with Amp and Cam.

2. Mutagenesis of NruI-HF

All residues Cys, Asp, Glu, Gly, His, Lys, Asn, Pro, Gln, Arg, Ser, Thr were changed to Ala at positions 8, 10, 12, 13, 15, 16, 19, 20, 21, 22, 23, 25, 26, 30, 34, 36, 38, 39, 44, 45, 46, 47, 49, 50, 53, 54, 55, 56, 57, 58, 59, 60, 61, 62, 63, 64, 68, 70, 71, 72, 73, 75, 77, 79, 80, 82, 83, 84, 85, 87, 89, 90, 91, 92, 93, 95, 96, 97, 99, 101, 103, 104, 106, 107, 112, 113, 114, 115, 117, 118, 119, 124, 125, 127, 132, 134, 137, 138, 139, 141, 146, 147, 148, 149, 152, 154, 155, 157, 158, 159, 162, 163, 165, 166, 168, 169, 170, 171, 174, 175, 177, 178, 180, 182, 184, 186, 188, 189, 190, 191, 193, 196, 197, 200, 201, 202, 204, 205, 206, 207, 208, 209, 211, and 213; Tyr was changed to Phe at the positions of 11, 31, 52, 69, 98, 64, and 187.

The mutagenesis methods were inverse PCR with paired primers followed by DpnI digestion. The treated product was then transformed into E. coli strain ER2683.

3. Selection of NruI-HF

Selection of NruI-HF was achieved using comparison of activity in NEB3 and NEB4 using dam– lambda DNA as substrate. Mutants with more activity than WT in NEB4 were selected as increased activity in NEB4 is an indicator of improved fidelity. The following mutants were found to have more activity in NEB4: G075A, Q099A, G155A, and P022A/R90A. P154A NruI(P022A/R90A) is designated as NruI-HF.

4. Purification of NruI-HF

Two liters of cell ER2683(pUC19-NruI(P022AR90A), pACYC184-Sbo13IM) were grown in LB with 100 µg/ml Amp and 33 µg/ml Cam at 37° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated NruI-HF was then added an equal volume of glycerol and stored at –20° C.

5. Comparison of NruI-HF and NruI-WT

The FIs of NruI-HF and NruI-WT have been determined separately on dam– lambda DNA in four NEB buffers with diluent A. The result is listed in Table 32 (below).

TABLE 32

Comparison of NruI-HF and NruI-WT

| Buffer | NruI-HF Activity | NruI-HF FI | NruI-WT Activity | NruI-WT FI | Improvement Factor |
|---|---|---|---|---|---|
| NEB1 | 0.4% | ≥64 | 12.5% | 64 | ≥1 |
| NEB2 | 6.3% | ≥1000 | 50% | 250 | ≥4 |
| NEB3 | 6.3% | ≥1000 | 100% | 500 | ≥2 |
| NEB4 | 100% | ≥16000 | 12.5% | 32 | ≥32 |

NruI-HF performed best in NEB4, in which the FI was ≥16000; NruI-WT performed best in NEB3, in which the FI was 500. The overall improvement factor is ≥16000/500=≥32.

Example 32: Engineering of High Fidelity NspI

1. Expression of NspI

NspI was expressed in E. coli transformed with pUC19-NspIR and pACYC-FatIM, each contains NspI endonuclease and methylase gene. The cells were grown at 37° C. overnight in LB with Amp and Cam.

2. Mutagenesis of NspI-HF

All residues Cys, Asp, Glu, Gly, His, Lys, Asn, Pro, Gln, Arg, Ser, Thr were changed to Ala at positions 9, 10, 12, 13, 14, 16, 17, 18, 19, 20, 21, 23, 26, 29, 30, 31, 32, 34, 36, 37, 39, 40, 41, 42, 44, 45, 46, 47, 50, 51, 52, 53, 55, 56, 58, 59, 60, 61, 62, 63, 64, 65, 66, 70, 71, 72, 73, 74, 77, 78, 80, 81, 82, 83, 85, 86, 87, 89, 90, 91, 93, 94, 96, 97, 99, 100, 102, 104, 107, 108, 111, 114, 116, 117, 120, 121, 122, 123, 124, 125, 126, 127, 128, 132, 133, 134, 136, 138, 139, 141, 143, 144, 145, 146, 147, 149, 150, 152, 153, 154, 155, 157, 158, 159, 161, 164, 165, 166, 167, 168, 169, 170, 171, 172, 175, 176, 177, 178, 180, 181, 184, 185, 186, 187, 188, 189, 191, 193, 195, 199, 200, 201, 202, 203, 205, 206, 208, 209, 210, 211, 212, 213, 215, 216, 217, 220, 222, 225, 227, 230, 231, 234, 235, 236, and 238; Tyr was changed to Phe at the positions of 48, 75, 113, 115, 198, and 224.

The mutagenesis methods were inverse PCR with paired primers followed by DpnI digestion. The treated product was then transformed into E. coli strain ER2566.

3. Selection of NspI-HF

Selection of NspI-HF was achieved using comparison of activity in NEB3 and NEB4 using pBR322 DNA as substrate. Mutants with more activity than WT in NEB4 were selected as increased activity in NEB4 is an indicator of improved fidelity. The following mutants were found to have more activity in NEB4: S097A and E125A. NspI(S097A) is designated as NspI-HF.

4. Purification of NspI-HF

Two liters of cell ER2566(pUC19-NspI(S097A), pACYC-FatIM)) were grown in LB with 100 µg/ml Amp and 33 µg/ml Cam at 37° C. overnight. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) pre-balanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated NspI-HF was then added an equal volume of glycerol and stored at –20° C.

5. Comparison of NspI-HF and NspI-WT

Figure 16:
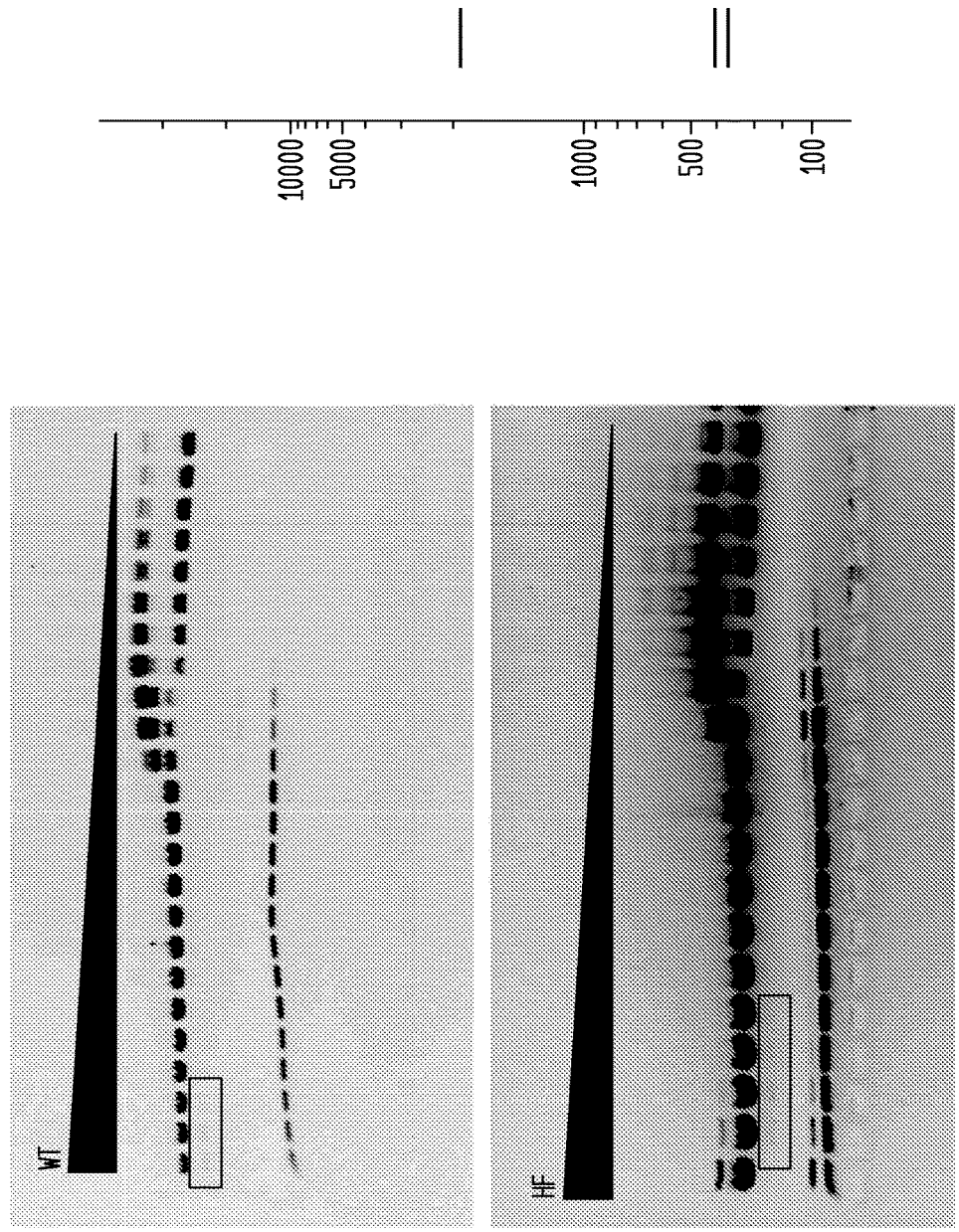
FIG. 16 shows a comparison of NspI-HF and NspI-WT on pUC19. The NspI-HF has an FI of 500 in NEB4, while the NspI-WT has an FI of 32, providing an improvement factor of at least 16. The right panel is the theoretical digestion pattern.

The FIs of NspI-HF and NspI-WT have been determined separately on pUC19 DNA in four NEB buffers with diluent A with BSA. The comparison is shown in FIG. 16, and the result is listed in Table 33 (below).

TABLE 33

Comparison of NspI-HF and NspI-WT

| Buffer | NspI-HF Activity | NspI-HF FI | NspI-WT Activity | NspI-WT FI | Improvement Factor |
|---|---|---|---|---|---|
| NEB1 | 100% | ≥4000 | 100% | 250 | ≥16 |
| NEB2 | 100% | ≥500 | 100% | 16 | ≥32 |
| NEB3 | 12.5% | ≥250 | 25% | 120 | ≥50 |
| NEB4 | 100% | 500 | 50% | 32 | ≥16 |

NspI-HF performed best in NEB1 and NEB4, in which the best FI was ≥4000; WT NspI performed best in NEB1 and NEB2, in which the best FI was 250. The overall improvement factor is ≥4000/250=≥16.

Example 33: Engineering of HF BsrFI

1. Expression of BsrFI

BsrFI was expressed in *E. coli* transformed with pBAD-BsrFIR and pSYX33-HpaIIM, each contains BsrFI endonuclease and methylase gene. The cells were grown at 37° C. overnight in LB with Amp and Kan with arabinose induction.

2. Mutagenesis of BsrFI-HF

All residues Cys, Asp, Glu, Gly, His, Lys, Asn, Pro, Gln, Arg, Ser, Thr were changed to Ala at positions 7, 8, 9, 12, 13, 15, 16, 17, 18, 19, 20, 21, 23, 25, 26, 28, 32, 35, 36, 37, 39, 40, 41, 42, 44, 45, 46, 48, 49, 51, 52, 56, 59, 61, 62, 64, 65, 66, 68, 72, 73, 74, 75, 76, 77, 80, 86, 87, 89, 91, 93, 94, 95, 97, 98, 103, 105, 106, 108, 109, 111, 113, 114, 117, 118, 119, 120, 121, 122, 123, 126, 128, 129, 130, 133, 134, 135, 136, 137, 139, 142, 143, 144, 145, 146, 151, 152, 153, 154, 157, 158, 159, 161, 162, 163, 165, 166, 168, 169, 170, 171, 173, 174, 177, 180, 181, 183, 184, 185, 187, 189, 190, 194, 196, 198, 199, 200, 202, 203, 204, 205, 206, 208, 211, 212, 213, 214, 217, 218, 222, 224, 226, 229, 230, 231, 233, 235, 238, 240, 241, 242, 243, 245, 246, 248, 249, 250, 253, 254, 257, 258, 259, 262, 264, 265, 266, 267, 268, 269, 272, 273, 276, 278, 279, 281, 282, 284, and 285; Tyr is changed to Phe at the positions of 14, 34, 53, 90, 96, 99, 125, 160, 227, 236, 237.

The mutagenesis methods were inverse PCR with paired primers followed by DpnI digestion. The treated product was then transformed into *E. coli* strain ER2566.

3. Selection of BsrFI-HF

Selection of BsrFI-HF was achieved using comparison of activity in NEB3 and NEB4 using pBR322 DNA as substrate. Mutants with more activity than WT in NEB4 were selected as increased activity in NEB4 is an indicator of improved fidelity. The following mutants were found to have more activity in NEB4: K021A/I031R and T120A. BsrFI (K021A/I031R) is designated as BsrFI-HF.

4. Purification of BsrFI-HF

Two liters of cell ER2566(pBAD-BsrFI(K021A/I031R), pSYX33-HpaIIM) were grown in LB with 100 μg/ml Amp and 33 μg/ml Kan at 37° C. overnight with 0.2% arabinose induction after 8 hours. The cells were harvested and sonicated in 20 ml 10 mM Tris-HCl, pH 7.5, 50 mM NaCl. After a centrifugation at 15,000 rpm for 30 minutes, the supernatant was loaded on the 5 ml HiTrap™ Heparin HP column (GE Healthcare, now Pfizer, Inc., Piscataway, N.J.) prebalanced by the same buffer by syringe injection. The column was then loaded on the system by the following procedure: 48 ml 10 mM Tris-HCl, pH 7.5, 50 mM NaCl, 100 ml 10 mM Tris-HCl, pH 7.5, 50 mM-1M NaCl linear gradient and followed by a 10 ml 10 mM Tris-HCl, pH 7.5, 1M NaCl step. The eluted fractions were then tested for activity. The fractions with highest activity were further concentrated by Vivaspin® 15R (Vivascience, now Sartorius Vivascience GmbH, Goettingen, Germany). The concentrated BsrFI-HF was then added an equal volume of glycerol and stored at −20° C.

5. Comparison of BsrFI-HF and WT BsrFI

Figure 17:
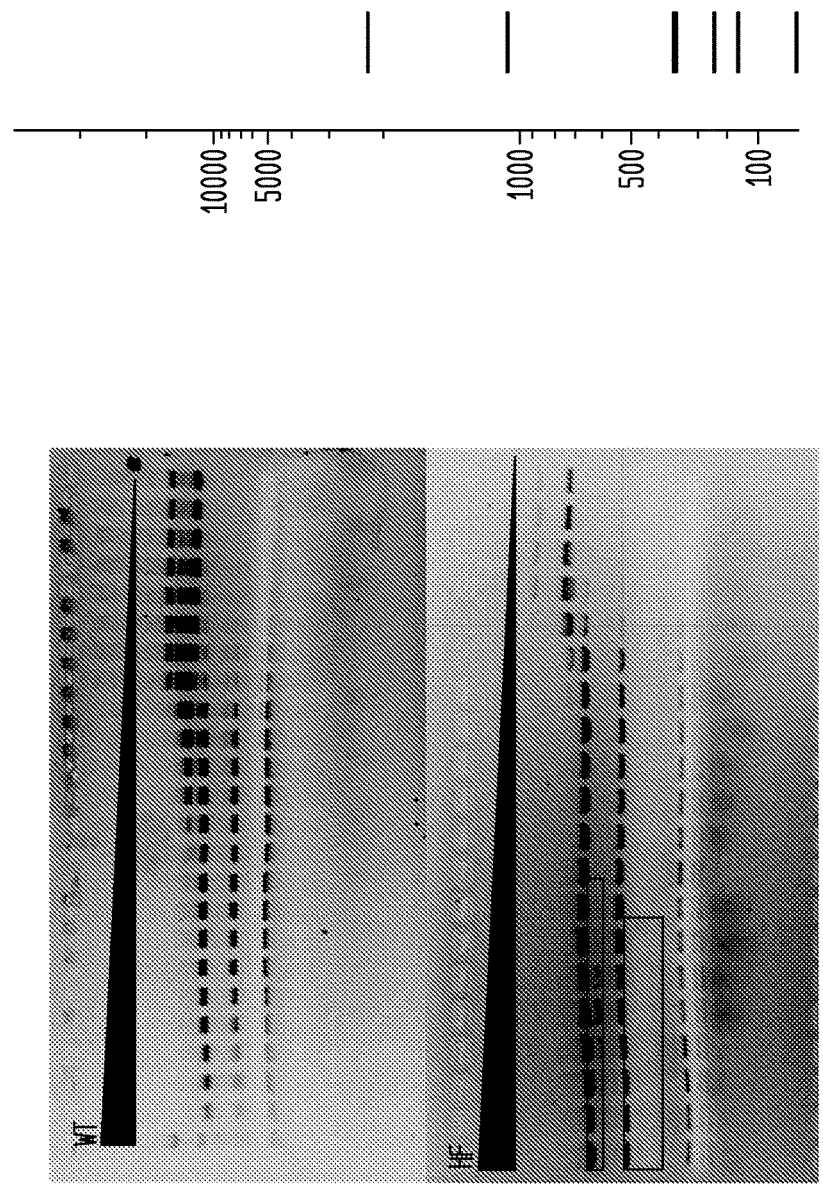
FIG. 17 shows a comparison of BsrFI-HF and BsrFI-WT on pBR322. The BsrFI-HF has an FI of at least 500 in NEB4, while the BsrFI-WT has an FI of 16, providing an improvement factor of at least 32. The right panel is the theoretical digestion pattern.

The FIs of BsrFI-HF and BsrFI-WT have been determined separately on pBR322 DNA in four NEB buffers with diluent A. The comparison is shown in FIG. 17, and the result is listed in Table 35 (below).

TABLE 35

Comparison of BsrFI-HF and BsrFI-WT

| Buffer | BsrFI-HF | | BsrFI-WT | | Improvement Factor |
| --- | --- | --- | --- | --- | --- |
| | Activity | FI | Activity | FI | |
| NEB1 | 100% | ≥500 | 25% | 16 | ≥32 |
| NEB2 | 12.5% | ≥64 | 100% | 4 | ≥500 |
| NEB3 | NC | NC | 3.1% | 8 | ≥−8 |
| NEB4 | 100% | ≥500 | 50% | 16 | ≥32 |

BsrFI-HF performed best in NEB1 and NEB4, in which the FI was ≥500; BsrFI-WT performed best in NEB2, in which the FI was 4. The overall improvement factor is ≥500/4=≥120.

Example 34: Engineering of HF BspEI

1. Expression of BspEI (SEQ ID No. 34)

BspEI was expressed in *E. coli* transformed with pLazz1-BspEIR and pACYC184-BspEIM, each contains BspEI endonuclease and methylase gene. The cells were grown at 37° C. overnight in LB with Amp and Cam.

2. Mutagenesis of BspEI-HF

All residues Cys, Asp, Glu, Gly, His, Lys, Asn, Pro, Gln, Arg, Ser, Thr were changed to Ala at positions 7, 8, 10, 11, 12, 13, 14, 17, 19, 20, 21, 22, 23, 27, 30, 31, 33, 34, 35, 36, 37, 39, 42, 43, 44, 45, 46, 48, 49, 51, 52, 53, 54, 55, 56, 58, 59, 60, 62, 63, 64, 66, 67, 68, 71, 72, 73, 74, 75, 78, 79, 81, 82, 84, 85, 88, 89, 91, 92, 93, 94, 95, 96, 98, 101, 102, 103, 106, 107, 108, 110, 111, 113, 114, 115, 117, 121, 122, 124, 126, 127, 128, 129, 132, 133, 135, 136, 137, 138, 140, 141, 148, 149, 151, 153, 155, 156, 157, 160, 162, 164, 166, 167, 168, 169, 172, 174, 175, 176, 177, 178, 182, 183, 184, 185, 186, 187, 189, 192, 193, 195, 196, 197, 198, 199, 200, 201, 203, 204, 208, 209, 212, 213, 214, 216, 217, 218, 219, 221, 222, 228, 229, 231, 232, 233, 234, 235, 236, 237, 238, 239, 240, 242, 244, 245, 246, 250, 251, 253, 254, 255, 256, 258, 260, 261, 263, 264, 266, 267, 269, 270, 271, 272, 273, 275, 276, 277, 281, 282, 283, 285, 286, 288, 289, 293, 294.

The mutagenesis methods were inverse PCR with paired primers followed by DpnI digestion. The treated product was then transformed into *E. coli* strain ER3081.

3. Selection of BspEI-HF

Selection of BspEI-HF was achieved using comparison of activity in NEB3 and NEB4 using unmethylated lambda (λ⁻) DNA as substrate. WT BspEI has more activity in NEB3, the one with more activity in NEB4 were selected. 6 mutants are found to have more activity in NEB4: K7A, T10A, N11A, N14A, Q232A and T199A. T199A has much higher activity than WT in NEB4. BspEI(T199A) is designated as BspEI-HF.

Example 35: Engineering of High Fidelity BamHI (Additional Mutants)

BamHI (SEQ ID No. 35) recognizes and digests at G/GATCC as described in Example 1 of International Publication No. WO 2009/009797. A mutant BamHI(E163A/E167T) was selected as the high fidelity version of the BamHI.

A complete coverage of mutation was done on BamHI. Aside from the residues reported in the previous patents and applications, the rest of the residues were also mutated to Ala at position of 3, 7, 8, 15, 16, 21, 22, 23, 24, 27, 29, 31, 33, 34, 35, 37, 38, 39, 45, 47, 48, 49, 53, 54, 55, 56, 57, 58, 59, 60, 63, 64, 67, 68, 73, 74, 79, 80, 82, 83, 85, 90, 91, 92, 93, 95, 99, 100, 102, 105, 108, 109, 110, 112, 115, 116, 117, 124, 125, 127, 128, 129, 130, 131, 134, 136, 138, 140, 141, 142, 143, 144, 145, 147, 148, 151, 152, 156, 158, 159, 162, 164, 166, 168, 171, 172, 173, 174, 175, 176, 177, 178, 179, 180, 185, 187, 188, 189, 190, 191, 192, 194, 197, 198, 203, 206, 210 and 212.

Among these mutants, P92A, P144A, G197A and M198A have higher fidelity than the wild type BamHI. P92A can be an alternative high fidelity BamHI.

What is claimed:

1. A composition comprising a variant SpeI restriction endonuclease having reduced star activity, wherein the variant SpeI restriction endonuclease comprises an amino acid sequence that differs from the amino acid sequence of the parent SpeI restriction endonuclease by an amino acid substitution at the position corresponding to position 65, in SEQ ID NO:17.

2. The composition according to claim 1, wherein the amino acid substitution is P65A.

3. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 59 in SEQ ID NO:17.

4. The composition according to claim 3, wherein the substitution is E59A.

5. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 108 in SEQ ID NO:17.

6. The composition according to claim 5, wherein the substitution is S108A.

7. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 172 in SEQ ID NO:17.

8. The composition according to claim 7, wherein the substitution is N172A.

9. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 174 in SEQ ID NO:17.

10. The composition according to claim 9, wherein the substitution is K174A.

11. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 179 in SEQ ID NO:17.

12. The composition according to claim 11, wherein the substitution is Q179A.

13. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 182 in SEQ ID NO:17.

14. The composition according to claim 13, wherein the substitution is G182A.

15. A composition comprising a variant SpeI restriction endonuclease having reduced star activity, wherein the variant SpeI restriction endonuclease comprises an amino acid sequence that differs from the amino acid sequence of the parent SpeI restriction endonuclease by a substitution at the amino acid position corresponding to position 55 in SEQ ID NO:17.

16. The composition according to claim 15, wherein the substitution is Y55F.

* * * * *